(12) United States Patent
Gulley et al.

(10) Patent No.: US 12,161,798 B2
(45) Date of Patent: Dec. 10, 2024

(54) PATIENT ATTACHMENT DETECTION IN RESPIRATORY FLOW THERAPY SYSTEMS

(71) Applicant: Fisher & Paykel Healthcare Limited, Auckland (NZ)

(72) Inventors: Anton Kim Gulley, Auckland (NZ); Bryn Alan Edwards, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 669 days.

(21) Appl. No.: 17/310,727

(22) PCT Filed: Mar. 4, 2020

(86) PCT No.: PCT/IB2020/051816
§ 371 (c)(1),
(2) Date: Aug. 19, 2021

(87) PCT Pub. No.: WO2020/178746
PCT Pub. Date: Sep. 10, 2020

(65) Prior Publication Data
US 2022/0134028 A1 May 5, 2022

Related U.S. Application Data

(60) Provisional application No. 62/893,122, filed on Aug. 28, 2019, provisional application No. 62/813,981, filed on Mar. 5, 2019.

(51) Int. Cl.
*A61M 16/00* (2006.01)
*A61B 5/00* (2006.01)
(Continued)

(52) U.S. Cl.
CPC ....... *A61M 16/0003* (2014.02); *A61B 5/4833* (2013.01); *A61M 16/0051* (2013.01);
(Continued)

(58) Field of Classification Search
CPC ...... A61M 2205/13; A61M 2205/3334; A61M 2205/3355; A61M 2205/3365; A61M 16/0666; A61M 16/024
See application file for complete search history.

(56) References Cited

U.S. PATENT DOCUMENTS 10,575,758 B2    3/2020  Ramanan
10,751,490 B2 *  8/2020  Martin .............. A61M 16/0051
(Continued)

FOREIGN PATENT DOCUMENTS

CN  102302817 A   1/2012
CN  107261280 A  10/2017
(Continued)

OTHER PUBLICATIONS

International Search Report in corresponding International Patent Application No. PCT/IB2020/051816, dated Jun. 22, 2020, in 8 pages.
(Continued)

*Primary Examiner* — Samchuan C Yao
*Assistant Examiner* — Sara K Toich
(74) *Attorney, Agent, or Firm* — Knobbe, Martens, Olson & Bear, LLP

(57) ABSTRACT

Systems and methods can determine whether a patient is attached to a respiratory device (such as to via a patient interface) by analyzing a flow parameter signal in the time domain. Additionally, the processes can classify the patient attachment status into one of the four categories: detached, attaching, attached, or detaching. The system can include a non-sealed patient interface, such as a nasal cannula in a nasal high flow therapy, or any other patient interfaces. Data of the patient's use of the respiratory system can provide therapy compliance and long-term trend of use information
(Continued)

and/or progress in the patient's respiratory functions and/or other physiological functions.

20 Claims, 30 Drawing Sheets

(51) Int. Cl.
*A61M 16/10* (2006.01)
*A61M 16/16* (2006.01)
*G16H 20/40* (2018.01)
*G16H 40/63* (2018.01)
*A61M 16/04* (2006.01)

(52) U.S. Cl.
CPC ...... *A61M 16/0069* (2014.02); *A61M 16/024* (2017.08); *A61M 16/1005* (2014.02); *A61M 16/161* (2014.02); *G16H 20/40* (2018.01); *G16H 40/63* (2018.01); *A61M 2016/0018* (2013.01); *A61M 2016/0027* (2013.01); *A61M 2016/003* (2013.01); *A61M 16/0465* (2013.01); *A61M 2202/0208* (2013.01); *A61M 2205/13* (2013.01); *A61M 2205/18* (2013.01); *A61M 2205/3334* (2013.01); *A61M 2205/502* (2013.01); *A61M 2230/432* (2013.01)

(56) References Cited

U.S. PATENT DOCUMENTS

| | | | | |
|---|---|---|---|---|
| 2003/0111079 A1* | 6/2003 | Matthews | ........... | A61M 16/026 128/204.18 |
| 2007/0157930 A1* | 7/2007 | Soliman | ............ | A61M 16/0051 128/204.23 |
| 2012/0247470 A1* | 10/2012 | Ho | .................... | A61M 16/0066 128/204.21 |
| 2016/0243325 A1* | 8/2016 | Bowman | ........... | A61M 16/0069 |

FOREIGN PATENT DOCUMENTS

| | | |
|---|---|---|
| WO | WO 1998/12965 A1 | 4/1998 |
| WO | WO 2014/128668 A1 | 8/2014 |
| WO | WO 2015/123113 A1 | 8/2015 |
| WO | WO 2017/027906 A1 | 2/2017 |
| WO | WO 2018/042376 A1 | 3/2018 |
| WO | WO 2018/089837 A1 | 5/2018 |
| WO | WO 2019/102384 A1 | 5/2019 |
| WO | WO 2020/178746 A1 | 9/2020 |

OTHER PUBLICATIONS

Written Opinion in corresponding International Patent Application No. PCT/IB2020/051816, dated Jun. 22, 2020, in 10 pages.

International Preliminary Report on Patentability in corresponding International Patent Application No. PCT/IB2020/051816, dated Aug. 25, 2021, in 11 pages.

* cited by examiner

PATIENT ATTACHMENT DETECTION IN RESPIRATORY FLOW THERAPY SYSTEMS

CROSS-REFERENCE TO RELATED APPLICATIONS

This application is a national phase of International Application No. PCT/IB2020/051816, filed Mar. 4, 2020, which claims priority from U.S. Provisional Application No. 62/813,981, filed Mar. 5, 2019 and U.S. Provisional Application No. 62/893,122, filed Aug. 28, 2019.

FIELD OF THE DISCLOSURE

The present disclosure relates to methods and systems for providing a respiratory flow therapy to a patient. In particular, the present disclosure relates to detecting whether a patient is attached to a respiratory flow system.

BACKGROUND

Breathing assistance apparatuses are used in various environments such as hospital, medical facility, residential care, or home environments to deliver a flow of gases to users or patients. A breathing assistance or respiratory therapy apparatus (collectively, "respiratory apparatus" or "respiratory devices") may be used to deliver supplementary oxygen or other gases with a flow of gases, and/or a humidification apparatus to deliver heated and humidified gases. A respiratory apparatus may allow adjustment and control over characteristics of the gases flow, including flow rate, temperature, gases concentration, humidity, pressure, etc. Sensors, such as flow sensors and/or pressure sensors are used to measure characteristics of the gases flow.

SUMMARY

Respiratory devices can monitor and determine various parameters related to a patient's use of the device. The parameter data can inform clinicians about a patient's health, use of the respiratory devices and/or progress in the patient's respiratory functions. The data can also be used to improve the functionality of the respiratory device itself.

Inspiration and expiration by a patient using a respiratory device can affect the gases flow in the device. This is because when the patient inhales through a patient interface, such as a mask or nasal cannula, the resistance to the gases flow in the patient interface decreases; when the patient exhales, the resistance to the gases flow in the patient interface increases. Some parameters, such as respiratory rate, are determined by monitoring variations due to the inspiration and expiration in a flow parameter signal.

In a sealed system, this inhalation and exhalation is relatively easy to measure. However, in an unsealed system, such as a nasal high flow system, patient inhalation and exhalation is more difficult to determine because of the open nature of the system. It can be easy to mistake an irregularity in a signal, in particular, a time domain signal, as a respiratory triggering event. The parameter determined from such analyses can be misleading when the respiratory device may detect a breath in the signal when there is no breath (for example, due to the patient being detached, not breathing through the nose, and/or other reasons).

The present disclosure provides processes of performing a time-domain analysis of a gases flow parameter to detect attachment and detachment of the patient to the respiratory system by determining a correlation value of the data of a flow parameter and comparing the correlation value with one or more threshold values. Additionally, the processes described herein can classify the patient attachment status into one of the four categories: detached, attaching, attached, or detaching.

The determination of patient attachment status can be fed into other control functions of the respiratory device, and/or other patient monitoring devices, such as for example, to synchronize delivery of gases when the patient is attached, interrupt an oxygen delivery control and/or control of the flow rate and/or power to heating element(s) in the device when the patient has taken off the patient interface, improve accuracy in determination of other parameters, such as respiratory rate, and/or provide therapy compliance and long-term trend of use information and/or progress in the patient's respiratory functions. The processes disclosed herein can be used when the patient interface is a non-sealed device, such as a nasal cannula in a nasal high flow therapy, or any other patient interfaces, such as a face mask, a nasal mask, a nasal pillow mask, an endotracheal tube, a tracheostomy interface, or others (such as in a Continuous Positive Airway Pressure (CPAP) therapy, and/or a Bi-level Positive Airway Pressure therapy).

In a configuration, a respiratory system configured to deliver a respiratory therapy to a patient and to provide information related to the patient's breathing can comprise a respiratory device comprising a controller, wherein the controller can be configured to receive data of a first parameter of a flow of gases or representative of performance of a component of the device, the first parameter indicative of the patient's respiration, determine a correlation value of the data of the first parameter by analyzing a trend in the data, and use the correlation value to determine that the patient is attached to a patient interface of the device.

In a configuration, the controller can be configured to evaluate the correlation value for a subset of the data of the first parameter.

In a configuration, the size of the subset can be chosen such that a frequency within a typical breathing frequency range results in higher correlation than another frequency above the typical breathing frequency range.

In a configuration, the size of the subset can be chosen such that the subset comprises data from a predetermined timespan.

In a configuration, the correlation value can be determined by analyzing a correlation between the data of the first parameter and one or more feature vectors.

In a configuration, the controller can be configured to filter the correlation value over time to give a filtered correlation value.

In a configuration, the controller can be configured to determine that the patient is attached to the patient interface if the filtered correlation value is above a first threshold.

In a configuration, the controller can be configured to determine that the patient is attached to the patient interface if the filtered correlation value is above a second threshold for a set amount of time.

In a configuration, the first threshold can be above the second threshold.

In a configuration, once determined to be attached, the patient can be determined to be detached if the filtered feature value is below a third threshold.

In a configuration, once determined to be attached, the patient can be determined to be detached if the filtered feature value is below a fourth threshold for a set amount of time.

In a configuration, the third threshold can be below the fourth threshold.

In a configuration, the fourth threshold can be equal to the second threshold. In a configuration, the fourth threshold can be below the second threshold.

In a configuration, the controller can be configured to determine that the patient is attaching if the filtered correlation value is between the first and second threshold for less than the set amount of time, provided that the patient was not already assumed to be attached.

In a configuration, once determined to be attaching, the patient can be determined to be detached if the correlation value falls below the second threshold.

In a configuration, the controller can be configured to determine that the patient is detaching if the filtered correlation value is between the third and fourth threshold for less than the set amount of time, provided that the patient was not already assumed to be detached.

In a configuration, once determined to be detaching, the patient can be determined to be attached if the correlation value rises above the fourth threshold.

In a configuration, the controller can use the determination of whether the patient is attached to determine whether or not to display certain parameters.

In a configuration, the controller can receive an estimate of the patient's respiratory rate and display the respiratory rate estimation if the patient is determined to be attached.

In a configuration, the device can be configured to synchronize the delivery of gases with the patient's breathing if the patient is determined to be attached.

In a configuration, the controller can log the time in each patient attachment status.

In a configuration, the device can generate an alarm when the patient becomes detached.

In a configuration, the device is configured to generate the alarm immediately after the patient becomes detached. In one example the device is configured to generate the alarm in real time as the patient is detected as detached.

In a configuration, the device is configured to generate the alarm following a preset time (i.e. predetermined time) after the patient becomes detached.

In a configuration, the preset time can be between about 10 seconds and about 10 minutes. In one example the device is configured to generate an alarm if the device detects the patient as being detached for the preset time. In one example the preset time is at least 1 min.

In one example, the preset time can be between about 30 seconds and about 5 minutes.

In one example, the preset time can be between about 1 minute and about 2 minutes. In one example the preset time between 2 mins and 3 mins. The device is configured to wait for a predetermined time (i.e. a preset time) in order to allow a patient or medical professional to correct a detached nasal cannula in case the cannula is accidently dislodged. The device is configured to alarm if the cannula is detected as dislodged for a preset time in order to warn a patient and/or a medical professional that the patient is not receiving flow of gases. The alarm provides a warning in case the patient is not receiving therapy thereby improving safety of the system and reducing the chances of a patient not receiving therapy due to detachment.

In a configuration, the alarm can be outputted through a nurse call port.

In a configuration, the alarm can be accompanied by the device providing an option to the user to confirm whether the patient is still attached. The option may be presented on a graphical user interface. The option may be presented as a button or a window that may be selected via the user interface.

In a configuration, the option to confirm whether the patient is still attached can be used to override the determination that the patient has become detached.

In a configuration, the device can suspend recording of certain patient parameters only when the patient is detached.

In a configuration, the patient parameters can include oxygen efficiency.

In a configuration, the oxygen efficiency can be based on SpO2 and FdO2.

In a configuration, the device can comprise a supplementary gases inlet and a valve, wherein the valve can be adjusted by the controller to regulate the flow of supplementary gases through the supplementary gases inlet. In one example the supplementary gases may be oxygen or may be nitrogen.

In a configuration, the controller can close the valve when the patient is detached. This reduces the waste of supplementary gases if the patient is not attached i.e. the patient is detached. The controller may be configured to close the valve and the controller may be configured to reopen the valve once the patient is detected as attached.

In a configuration, the controller can control a flow generator to achieve a flow rate, wherein the controller can adjust the flow rate when the patient is detached. The flow generator may be a blower.

In a configuration, the adjusting of the flow rate can comprise decreasing the flow rate.

In a configuration, the adjusting of the flow rate can comprise increasing the flow rate. The controller may be configured to increase the flow rate in order to overcome a partial detachment e.g. if the nasal cannula is partially dislodged. The increased flow rate helps to continue to provide respiratory gases to the patient, such that the patient can receive respiratory therapy. Respiratory therapy, in one example may be high flow therapy. The increased flow rate may deliver an adequate amount of gases flow to the patient even if the patient interface is partially dislodged and detected as detached.

In a configuration, the increasing of the flow rate can last for an initial period of time.

In a configuration, the initial time can be between about 10 seconds and about 10 minutes.

In a configuration, the initial time can be between about 30 seconds and about 5 minutes.

In a configuration, the initial time can be between about 1 minute and about 2 minutes.

In a configuration, the controller can decrease the flow rate when the patient is still determined to be detached after the initial period. The decrease in flow rate after the initial period of time helps to protect the flow generator (e.g. blower) from over work. This can be useful if the respiratory therapy device is being operated using a battery. The blower being switched off of the flow rate being decreased can help to conserve battery power.

In a configuration, the data of the first parameter can comprise an absolute value of the first parameter. In a configuration, the data of the first parameter can comprise a variation of the first parameter.

In a configuration, the variation can be determined by subtracting a target value of the first parameter from the measured value of the first parameter. In a configuration, the variation can be determined by subtracting an estimated effect of a second parameter from the measured value of the first parameter.

In a configuration, the first parameter can be flow rate. In a configuration, the first parameter can be pressure.

In a configuration, the second parameter can be motor speed. In a configuration, the second parameter can be pressure.

In a configuration, the system can be a non-sealed system.

In a configuration, the patient interface can comprise a nasal cannula or a tracheostomy interface.

In a configuration, the system can be configured to deliver a nasal high flow therapy.

In a configuration, the system can be a sealed system.

In a configuration, the system can comprise the patient interface, the patient interface being a face mask, a nasal mask, an endotracheal tube, or a tracheostomy interface.

In a configuration, the system can comprise a humidifier configured to humidify the gases flow to a patient.

In a configuration, the controller is configured to reduce power to the humidifier when the patient is detached.

In a configuration, the controller is configured to switch off power to the humidifier when the patient is detached. In one configuration the humidifier comprises a heater plate and a humidification chamber. The chamber is positioned on the heater plate when in an operative configuration. The controller is configured to switch off power to the heater plate if the patient is detected as being detached. This conserves battery power if the device is operated using a battery. Switching off the power also reduces the chamber from overheating or becoming damaged due to prolonged heating. Further this also helps to conserve the condition of the heater plate and chamber. Further switching off the power to the heater plate reduces the chances of increasing the enthalpy of gases delivered to the patient since the heating is reduced, thereby reducing the amount of heat in the humidification chamber.

In a configuration, the system can comprise a patient breathing conduit having a heating element configured to heat the gases flow to a patient. The heating element may be a heater wire. The heater wire may be embedded within the wall of the conduit and may be spirally wound. Alternatively, the heater wire may positioned within the lumen of the conduit.

In a configuration, the controller is configured to reduce power to the heating element of the patient breathing conduit when the patient is detached. This is advantageous because it reduces the chances of the breathing conduit being overheated or damage to the conduit from the heating. Reducing the power or switching off the power to the conduit heating element (e.g. a heater wire within the conduit) can also reduce or prevent excessive enthalpy of the gases.

In a configuration, the controller is configured to switch off power to the heating element of the patient breathing conduit when the patient is detached. Switching off the power has similar advantages as above.

In a configuration, the system can comprise a display configured to receive from the one or more processors and display information related to whether the patient is attached to the system.

In a configuration, a method of determining a patient detachment and/or attachment from a respiratory system configured to deliver a respiratory therapy to a patient and also configured to provide information related to the patient's breathing can comprise using a controller of a respiratory device: receiving data of a first parameter of a flow of gases or representative of performance of a component of the device, the first parameter indicative of the patient's respiration; determining a correlation value of the data of the first parameter by analyzing a trend in the data; and using the correlation value to determine the patient is connected to a patient interface of the system.

In a configuration, determining can comprise evaluating the correlation value for a recent subset of the data of the first parameter.

In a configuration, the method can comprise choosing a size of the subset such that a frequency within a typical breathing frequency range results in higher correlation than another frequency above the typical breathing frequency range.

In a configuration, the size of the subset can be chosen such that the subset comprises data from a predetermined timespan.

In a configuration, determining the correlation value can comprise analyzing a correlation between the data of the first parameter and one or more feature vectors.

In a configuration, the method can further comprise filtering the correlation value over time to give a filtered correlation value.

In a configuration, the patient can be determined to be attached to the patient interface if the filtered correlation value is above a first threshold.

In a configuration, the patient can be determined to be attached to the patient interface if the filtered correlation value is above a second threshold for a set amount of time.

In a configuration, the first threshold can be above the second threshold.

In a configuration, once determined to be attached, the patient can be determined to be detached if the filtered feature value is below a third threshold.

In a configuration, once determined to be attached, the patient can be determined to be detached if the filtered feature value is below a fourth threshold for a set amount of time.

In a configuration, the third threshold can be below the fourth threshold.

In a configuration, the fourth threshold can be equal to the second threshold. In a configuration, the fourth threshold can be below the second threshold.

In a configuration, the patient can be determined to be attaching if the filtered correlation value is between the first and second threshold for less than the set amount of time, provided that the patient was not already assumed to be attached.

In a configuration, once determined to be attaching, the patient can be determined to be detached if the correlation value falls below the second threshold.

In a configuration, the patient can be determined to be detaching if the filtered correlation value is between the third and fourth threshold for less than the set amount of time, provided that the patient was not already assumed to be detached.

In a configuration, once determined to be detaching, the patient can be determined to be attached if the correlation value rises above the fourth threshold.

In a configuration, the method can further comprise using the determination of whether the patient is attached to determine whether or not to display certain parameters.

In a configuration, the method can further comprise receiving an estimate of the patient's respiratory rate and displaying the respiratory rate estimation if the patient is determined to be attached.

In a configuration, the method can further comprise synchronizing the delivery of gases by the device with the patient's breathing if the patient is determined to be attached.

In a configuration, the method can further comprise logging the time in each patient attachment status.

In a configuration, the method can further comprise generating an alarm when the patient becomes detached.

In a configuration, the method can further comprise generating the alarm immediately after the patient becomes detached.

In a configuration, the method can further comprise generating the alarm following a preset time after the patient becomes detached.

In a configuration, the preset time can be between about 10 seconds and about 10 minutes.

In a configuration, the preset time can be between about 30 seconds and about 5 minutes.

In a configuration, the preset time can be between about 1 minute and about 2 minutes.

In a configuration, the method can further comprise outputting the alarm through a nurse call port.

In a configuration, the method can further comprise accompanying the alarm with providing an option to the user to confirm whether the patient is still attached.

In a configuration, the option to confirm whether the patient is still attached can be used to override the determination that the patient has become detached.

In a configuration, the method can further comprise suspending recording of certain patient parameters only when the patient is detached.

In a configuration, the patient parameters can include oxygen efficiency.

In a configuration, the oxygen efficiency can be based on SpO2 and FdO2.

In a configuration, the device can comprise a supplementary gases inlet and a valve, wherein the method can further comprise the valve being adjusted by the controller to regulate the flow of supplementary gases through the supplementary gases inlet.

In a configuration, the method can further comprise the controller closing the valve when the patient is detached.

In a configuration, the method can further comprise the controller controlling a flow generator to achieve a flow rate, wherein the controller adjusts the flow rate when the patient is detached.

In a configuration, the adjusting of the flow rate can comprise decreasing the flow rate.

In a configuration, the adjusting of the flow rate can comprise increasing the flow rate.

In a configuration, the increasing of the flow rate can last for an initial period of time.

In a configuration, the initial time can be between about 10 seconds and about 10 minutes.

In a configuration, the initial time can be between about 30 seconds and about 5 minutes.

In a configuration, the initial time can be between about 1 minute and about 2 minutes.

In a configuration, the method can further comprise the controller decreasing the flow rate when the patient is still determined to be detached after the initial period.

In a configuration, the data of the first parameter can comprise an absolute value of the first parameter. In a configuration, the data of the first parameter can comprise a variation of the first parameter.

In a configuration, the method can further comprise determining the variation by subtracting a target value of the first parameter from the measured value of the first parameter.

In a configuration, the method can further comprise determining the variation by subtracting an estimated effect of a second parameter from the measured value of the first parameter.

In a configuration, the first parameter can be flow rate. In a configuration, the first parameter can be pressure.

In a configuration, the second parameter can be motor speed. In a configuration, the second parameter can be pressure.

In a configuration, the system can be a non-sealed system.

In a configuration, the system can be configured to deliver a nasal high flow therapy.

In a configuration, the system can comprise the patient interface, the patient interface being a nasal cannula or a tracheostomy interface.

In a configuration, the system can be a sealed system.

In a configuration, the system can comprise the patient interface, the patient interface being a face mask, a nasal mask, an endotracheal tube, or a tracheostomy interface.

In a configuration, the system can comprise a humidifier configured to humidify the gases flow to a patient.

In a configuration, the method can further comprise the controller reducing power to the humidifier when the patient is detached.

In a configuration, the method can further comprise the controller switching off power to the humidifier when the patient is detached.

In a configuration, the system can comprise a patient breathing conduit having a heating element configured to heat the gases flow to a patient.

In a configuration, the method can further comprise the controller reducing power to the heating element of the patient breathing conduit when the patient is detached.

In a configuration, the method can further comprise the controller switching off power to the heating element of the patient breathing conduit when the patient is detached.

In a configuration, the system can comprise a display configured to receive from the one or more processors and display information related to whether the patient is attached to the system.

In a configuration, a respiratory system that can be configured to deliver a respiratory therapy to a patient, the system can also be configured to provide information related to a patient's breathing, the system can include a respiratory device having a controller, wherein the controller can be configured to receive data of a first parameter of a flow of gases or representative of performance of a component of the respiratory device, the first parameter indicative of the patient's respiration, generate flow parameter variation data based on the data of the first parameter; select a portion of the flow parameter variation data; and generate a measure of instantaneous patient ventilation based on the portion of the flow parameter variation data.

In a configuration, the controller can be configured to fit one or more functions to the selected portion of the flow parameter variation data or apply one or more functions to the selected portion of the flow parameter variation data, and generating the measure of instantaneous patient ventilation can comprise determining an area under a curve generated by the one or more functions. In a configuration, the controller can be configured to apply one or more functions to the selected portion of the flow parameter variation data, and wherein generating the measure of instantaneous patient ventilation comprises determining an area under a curve generated by the one or more functions. The one or more functions may be a straight line(s) or nonlinear line(s) or a combination thereof. The curve generated by the one or more functions may be a straight line, non-linear line, or a combination thereof. In a configuration, one or more functions may be applied to the flow parameter variation data to output a particular value, such as instantaneous patient ventilation or other similar value.

In a configuration, the first parameter can be indicative of flow rate. In a configuration, flow rate is total flow rate.

In a configuration, the flow parameter variation data can be generated by subtracting a target value of the first parameter from a measured value of the first parameter.

In a configuration, the controller can be further configured to receive data of a second parameter of the flow of gases or representative of performance of a second component of the device, and wherein the flow parameter variation data can be generated by subtracting an estimated effect of the second parameter from a measured value of the first parameter.

In a configuration, the second parameter can be indicative of or is motor speed.

In a configuration, the second parameter can be indicative of or is pressure.

In a configuration, the flow parameter variation data can be generated by subtracting a first average value of the first parameter from a second average value of the first parameter.

In a configuration, the second average value can be based on measured values of the first parameter.

In a configuration, the first average value of the first parameter can be determined by applying an ongoing filter to the first parameter.

In a configuration, the portion of the flow parameter variation data comprises data relating to a time period within a predefined time period.

In a configuration, the portion of the flow parameter variation data can represent a length of time.

In a configuration, the length of time can be such that signal noise can be filtered out of the measure of instantaneous patient ventilation.

In a configuration, the length of time can be such that expected breathing frequencies result in an increased measure of instantaneous patient ventilation.

In a configuration, the length of 0.5-2 seconds.

In a configuration, the controller can be configured to perform a least squares fit to fit the one or more functions to the selected portion of the flow parameter variation data.

In a configuration, the curve generated by the one or more functions can be a straight line.

In a configuration, the curve generated by the one or more functions can be a horizontal line.

In a configuration, the one or more functions can be algebraic.

In a configuration, the one or more functions can be transcendental.

In a configuration, the one or more functions can generate a line of best fit.

In a configuration, the measure of instantaneous patient ventilation can be generated based on the area under an absolute value of the curve generated by the one or more functions.

In a configuration, the area under the curve can be determined by finding an integral of the absolute value of the curve generated by the one or more functions.

In a configuration, a method of generating a measure of instantaneous patient ventilation with a respiratory system that can be configured to deliver a respiratory therapy to a patient, the method can comprise using a controller of a respiratory device: receiving data of a first parameter of a flow of gases or representative of performance of a component of the device, the first parameter can be indicative of the patient's respiration; generating flow parameter variation data based on the data of the first parameter; selecting a portion of the flow parameter variation data; and generating a measure of instantaneous patient ventilation based on the portion of the flow parameter variation data.

In a configuration, the method can further comprise fitting one or more functions to the selected portion of the flow parameter variation data, and wherein generating a measure of instantaneous patient ventilation can comprises determining an area under a curve generated by the one or more functions. In a configuration, the method can further comprise applying one or more functions to the selected portion of the flow parameter variation data, and wherein generating the measure of instantaneous patient ventilation comprises determining an area under a curve generated by the one or more functions.

In a configuration, the first parameter can be indicative of or is flow rate. In a configuration, flow rate is total flow rate.

In a configuration, the method can further comprise generating the flow parameter variation data which can comprise subtracting a target value of the first parameter from a measured value of the first parameter.

In a configuration, the method can further comprise using the controller of the respiratory device to receive data of a second parameter of the flow of gases or representative of performance of a second component of the device, and wherein generating the flow parameter variation data can comprise subtracting an estimated effect of the second parameter from a measured value of the first parameter.

In a configuration, the second parameter can be indicative of or is motor speed.

In a configuration, the second parameter can be indicative of or is pressure.

In a configuration, generating the flow parameter variation data can comprise subtracting a first average value of the first parameter from a second average value of the first parameter.

In a configuration, the second average value can be based on measured values of the first parameter.

In a configuration, the first average value of the first parameter can be determined by applying an ongoing filter to the first parameter.

In a configuration, the portion of the flow parameter variation data can comprise data relating to a time period within a predefined time period.

In a configuration, the portion of the flow parameter variation data can represent a length of time.

In a configuration, the length of time can be such that signal noise is filtered out of the measure of instantaneous patient ventilation.

In a configuration, the length of time can be such that expected breathing frequencies result in an increased measure of instantaneous patient ventilation.

In a configuration, the length of time can be 0.5-2 seconds.

In a configuration, the controller can perform a least squares fit to fit the one or more functions to the selected portion of the flow parameter variation data.

In a configuration, the curve generated by the one or more functions can be a straight line.

In a configuration, the curve generated by the one or more functions can be a horizontal line.

In a configuration, the one or more functions can be algebraic.

In a configuration, the one or more functions can be transcendental.

In a configuration, the one or more functions can generate a line of best fit.

In a configuration, the measure of instantaneous patient ventilation can be generated based on the area under an absolute value of the curve generated by the one or more functions.

In a configuration, the area under the curve can be determined by finding an integral of the absolute value of the curve generated by the one or more functions.

In a configuration, a respiratory system can be configured to deliver a respiratory therapy to a patient, the system also configured to provide information related to a patient's breathing, the system can comprise a respiratory device that can comprise a controller, wherein the controller can be configured to receive data of a first parameter of a flow of gases or representative of performance of a component of the device, the first parameter can be indicative of the patient's respiration, generate flow parameter variation data based on the data of the first parameter; generate a measure of patient ventilation based on the flow parameter variation data; generate a measure of total signal fluctuation based on the flow parameter variation data; and determine a patient attachment based on a comparison between the measure of patient ventilation and the measure of total signal fluctuation.

In a configuration, the first parameter can be indicative of or is flow rate.

In a configuration, the flow parameter variation data can be generated by subtracting a target value of the first parameter from a measured value of the first parameter.

In a configuration, the controller can be further configured to receive data of a second parameter of the flow of gases or representative of performance of a second component of the device, and wherein the flow parameter variation data can be generated by subtracting an estimated effect of the second parameter from a measured value of the first parameter.

In a configuration, the second parameter can be indicative of or is motor speed.

In a configuration, the second parameter can be indicative of or is pressure.

In a configuration, the flow parameter variation data can be generated by subtracting a first average value of the first parameter from a second average value of the first parameter.

In a configuration, the second average value can be based on measured values of the first parameter.

In a configuration, the first average value of the first parameter can be determined by applying an ongoing filter to the first parameter.

In a configuration, the controller can be further configured to generate a measure of instantaneous patient ventilation from the flow parameter variation data, and wherein the measure of patient ventilation can be generated by filtering the measure of instantaneous patient ventilation.

In a configuration, the controller can be further configured to select a portion of the flow parameter variation data.

In a configuration, the portion of the flow parameter variation data can represent 0.5-2 seconds.

In a configuration, the measure of instantaneous patient ventilation can be generated by fitting one or more functions to the selected portion of the flow parameter variation data and determining an area under an absolute value of a curve generated by the one or more functions. The one or more functions may be a straight line(s) or nonlinear line(s) or a combination thereof. The curve generated by the one or more functions may be a straight line, non-linear line, or a combination thereof. In a configuration, one or more functions may be applied to the flow parameter variation data to output a particular value, such as instantaneous patient ventilation or other similar value.

In a configuration, the controller can be configured to perform a least squares fit to fit the one or more functions to the selected portion of the flow parameter variation data.

In a configuration, the curve generated by the one or more functions can be a straight line.

In a configuration, the curve generated by the one or more functions can be a horizontal line.

In a configuration, determining the area under the absolute value of the curve can comprise finding an integral of the absolute value of the curve generated by the one or more functions.

In a configuration, the controller can be further configured to generate a measure of instantaneous total signal fluctuation from the flow parameter variation data, and wherein the measure of total signal fluctuation can be generated by filtering the measure of instantaneous total signal fluctuation.

In a configuration, the measure of instantaneous total signal fluctuation can be determined by taking the absolute value of the flow parameter variation data.

In a configuration, the measure of instantaneous total signal fluctuation can be determined by taking the square of the flow parameter variation data.

In a configuration, comparing the measure of patient ventilation and the measure of total signal fluctuation can comprise taking the ratio between the measure of patient ventilation and the measure of total signal fluctuation.

In a configuration, once determined to be attached, the controller can be configured to determine that the patient is detached if the ratio falls below an attachment threshold. In a configuration, once determined to be attached, the controller is configured to determine that the patient is attached if the ratio does not fall below an attachment threshold.

In a configuration, once determined to be detached, the controller can be configured to determine that the patient is attached if the ratio exceeds an attachment threshold.

In a configuration, once determined to be detached, the controller can be configured to determine that the patient is detached if the ratio does not exceed an attachment threshold.

In a configuration, the controller can be configured to determine that the patient is attached if the ratio is above a first threshold.

In a configuration, the controller can be configured to determine that the patient is attached if the ratio is above a second threshold for a set amount of time.

In a configuration, the first threshold can be above the second threshold.

In a configuration, once determined to be attached, the patient can be determined to be detached if the ratio is below a third threshold.

In a configuration, once determined to be attached, the patient can determined to be detached if the ratio is below a fourth threshold for a set amount of time.

In a configuration, the third threshold can be below the fourth threshold.

In a configuration, the fourth threshold can be equal to the second threshold.

In a configuration, the fourth threshold can be below second threshold.

In a configuration, the controller can be configured to determine that the patient is attaching if the ratio is between the first and second threshold for less than the set amount of time, provided that the patient was not already assumed to be attached.

In a configuration, once determined to be attaching, the patient can be determined to be detached if the ratio falls below the second threshold.

In a configuration, the controller can be configured to determine that the patient is detaching if the ratio is between the third and fourth threshold for less than the set amount of time, provided that the patient was not already assumed to be detached.

In a configuration, once determined to be detaching, the patient can be determined to be attached if the ratio rises above the fourth threshold.

In a configuration, the controller can be configured to use the determination of whether the patient is attached to determine whether or not to display certain parameters.

In a configuration, the controller can be configured to receive an estimate of the patient's respiratory rate and displays the respiratory rate estimation if the patient is determined to be attached.

In a configuration, the respiratory device can be configured to synchronize a delivery of gases with a patient's breathing if the patient is determined to be attached.

In a configuration, the controller can be configured to log the time in each patient attachment status.

In a configuration, the respiratory device can generate an alarm when the patient becomes detached.

In a configuration, the device can generate the alarm immediately after the patient becomes detached.

In a configuration, the device can generate the alarm following a preset time after the patient becomes detached.

In a configuration, the preset time can be between about 10 seconds and about 10 minutes.

In a configuration, the preset time can be between about 30 seconds and about 5 minutes.

In a configuration, the preset time can be between about 1 minute and about 2 minutes.

In a configuration, the alarm can be outputted through a nurse call port.

In a configuration, the alarm can be accompanied by the device providing an option to the user to confirm whether the patient is still attached.

In a configuration, the option to confirm whether the patient is still attached can be used to override the determination that the patient has become detached.

In a configuration, the respiratory device can suspend recording of certain patient parameters only when the patient is detached.

In a configuration, the patient parameters can include oxygen efficiency.

In a configuration, the oxygen efficiency can be based on SpO2 and FdO2.

In a configuration, the device can comprise a supplementary gases inlet and a valve, wherein the valve can be adjusted by the controller to regulate the flow of supplementary gases through the supplementary gases inlet.

In a configuration, the controller can close the valve when the patient is detached.

In a configuration, the controller can control a flow generator to achieve a flow rate, wherein the controller can adjust the flow rate when the patient is detached.

In a configuration, the adjusting of the flow rate can comprise decreasing the flow rate.

In a configuration, the adjusting of the flow rate can comprise increasing the flow rate.

In a configuration, the increasing of the flow rate can last for an initial period of time.

In a configuration, the initial time can be between about 10 seconds and about 10 minutes.

In a configuration, the initial time can be between about 30 seconds and about 5 minutes.

In a configuration, the initial time can be between about 1 minute and about 2 minutes.

In a configuration, the controller can decrease the flow rate when the patient is still determined to be detached after the initial period.

In a configuration, a method of determining a patient detachment and/or attachment from a respiratory system can be configured to deliver a respiratory therapy to a patient, the system can also be configured to provide information related to the patient's breathing, the method can comprise using a controller of a respiratory device: receiving data of a first parameter of a flow of gases or representative of performance of a component of the device, the first parameter indicative of the patient's respiration, generating flow parameter variation data based on the data of the first parameter; generating a measure of patient ventilation based on the flow parameter variation data; generating a measure of total signal fluctuation based on the flow parameter variation data; and determining a patient attachment based on a comparison between the measure of patient ventilation and the measure of total signal fluctuation.

In a configuration, the first parameter can be indicative of or is flow rate.

In a configuration, generating the flow parameter variation data can comprise subtracting a target value of the first parameter from a measured value of the first parameter.

In a configuration, the method can further comprise using a controller of a respiratory device to receive data of a second parameter of the flow of gases or representative of performance of a second component of the device; and wherein generating the flow parameter variation data can comprise subtracting an estimated effect of the second parameter from a measured value of the first parameter.

In a configuration, the second parameter can be indicative of or is motor speed.

In a configuration, the second parameter can be indicative of or is pressure.

In a configuration, generating the flow parameter variation data can comprise subtracting a first average value of the first parameter from a second average value of the first parameter.

In a configuration, the second average value can be based on measured values of the first parameter.

In a configuration, the first average value of the first parameter can be determined by applying an ongoing filter to the first parameter.

In a configuration, the method can further comprise using a controller of a respiratory device to generate a measure of instantaneous patient ventilation from the flow parameter variation data, and wherein generating the measure of patient ventilation can comprise filtering the measure of instantaneous patient ventilation.

In a configuration, the method can further comprise using a controller of a respiratory device to select a portion of the flow parameter variation data.

In a configuration, the portion of the flow parameter variation data can represent 0.5-2 seconds.

In a configuration, generating the measure of instantaneous patient ventilation can comprise fitting one or more functions to the selected portion of the flow parameter variation data and determining an area under an absolute value of a curve generated by the one or more functions.

In a configuration, determining the area under the absolute value of the curve generated by the one or more functions can comprise the controller performing a least squares fit to fit the one or more functions to the selected portion of the flow parameter variation data.

In a configuration, the curve generated by the one or more functions can be a straight line.

In a configuration, the curve generated by the one or more functions can be a horizontal line.

In a configuration, the area under the absolute value of the curve can be determined by finding an integral of the absolute value of the curve generated by the one or more functions.

In a configuration, the method can further comprise using a controller of a respiratory device to generate a measure of instantaneous total signal fluctuation from the flow parameter variation data, and wherein generating the measure of total signal fluctuation can comprise filtering the measure of instantaneous total signal fluctuation.

In a configuration, generating the measure of instantaneous total signal fluctuation can comprise taking the absolute value of the flow parameter variation data.

In a configuration, generating the measure of instantaneous total signal fluctuation can comprise taking the square of the flow parameter variation data.

In a configuration, comparing the measure of patient ventilation and the measure of total signal fluctuation can comprise taking the ratio between the measure of patient ventilation and the measure of total signal fluctuation.

In a configuration, once determined to be attached, the patient can be determined to be detached if the ratio falls below an attachment threshold.

In a configuration, once determined to be attached, the patient can be determined to be attached if the ratio does not fall below an attachment threshold.

In a configuration, once determined to be detached, the patient can be determined to be attached if the ratio exceeds an attachment threshold.

In a configuration, once determined to be detached, the patient can be determined to be detached if the ratio does not exceed an attachment threshold.

In a configuration, wherein the patient can be determined to be attached if the ratio is above a first threshold.

In a configuration, the patient can be determined to be attached if the ratio is above a second threshold for a set amount of time.

In a configuration, the first threshold can be above the second threshold.

In a configuration, once determined to be attached, the patient can be determined to be detached if the ratio is below a third threshold.

In a configuration, once determined to be attached, the patient can be determined to be detached if the ratio is below a fourth threshold for a set amount of time.

In a configuration, the third threshold can be below the fourth threshold.

In a configuration, the fourth threshold can be equal to the second threshold.

In a configuration, the fourth threshold can be below the second threshold.

In a configuration, the patient can be determined to be attaching if the ratio is between the first and second threshold for less than the set amount of time, provided that the patient was not already assumed to be attached.

In a configuration, once determined to be attaching, the patient can be determined to be detached if the ratio falls below the second threshold.

In a configuration, the patient can be determined to be detaching if the ratio is between the third and fourth threshold for less than the set amount of time, provided that the patient was not already assumed to be detached.

In a configuration, once determined to be detaching, the patient can be determined to be attached if the ratio rises above the fourth threshold.

In a configuration, the method can further comprise using a controller of a respiratory device to determine whether or not to display certain parameters based on whether the patient is attached.

In a configuration, the method can further comprise using a controller of a respiratory device to receive an estimate of the patient's respiratory rate and display the respiratory rate estimation if the patient is determined to be attached.

In a configuration, the method can further comprise using a controller of a respiratory device to synchronize a delivery of gases with a patient's breathing if the patient is determined to be attached.

In a configuration, the method can further comprise using a controller of the respiratory device to log a time in each patient attachment status.

In a configuration, the method can further comprise using a controller of the respiratory device to generate an alarm when the patient becomes detached.

In a configuration, the method can further comprise generating the alarm immediately after the patient becomes detached.

In a configuration, the method can further comprise generating the alarm following a preset time after the patient becomes detached.

In a configuration, the preset time can be between about 10 seconds and about 10 minutes.

In a configuration, the preset time can be between about 30 seconds and about 5 minutes.

In a configuration, the preset time can be between about 1 minute and about 2 minutes.

In a configuration, the method can further comprise outputting the alarm through a nurse call port.

In a configuration, the method can further comprise accompanying the alarm with providing an option to the user to confirm whether the patient is still attached.

In a configuration, the option to confirm whether the patient is still attached can be used to override the determination that the patient has become detached.

In a configuration, the method can further comprise using a controller of the respiratory device to suspend recording of certain patient parameters only when the patient is detached.

In a configuration, the patient parameters can include oxygen efficiency.

In a configuration, the oxygen efficiency can be based on SpO2 and FdO2.

In a configuration, the device can comprise a supplementary gases inlet and a valve, wherein the method can further comprise the valve being adjusted by the controller to regulate the flow of supplementary gases through the supplementary gases inlet.

In a configuration, the method can further comprise the controller closing the valve when the patient is detached.

In a configuration, the method can further comprise the controller controlling a flow generator to achieve a flow rate, wherein the controller is configured to adjust the flow rate when the patient is detached.

In a configuration, the adjusting of the flow rate can comprise decreasing the flow rate.

In a configuration, the adjusting of the flow rate can comprise increasing the flow rate.

In a configuration, the increasing of the flow rate can last for an initial period of time.

In a configuration, the initial time can be between about 10 seconds and about 10 minutes.

In a configuration, the initial time can be between about 30 seconds and about 5 minutes.

In a configuration, the initial time can be between about 1 minute and about 2 minutes.

In a configuration, the method can further comprise the controller decreasing the flow rate when the patient is still determined to be detached after the initial period.

In a further configuration the respiratory device comprises a controller that is configured to determine usage of the respiratory device based on the amount of time the patient is detected as attached. The controller is configured to keep a track of the amount of time the patient is detected as being attached. The controller may further determine and count the number of times the patient is detected as detached within a predefined period of time. The predefined period of time may be, for example, a therapy session. The controller may be configured to transmit the amount of time the patient is detected as attached to a remote computing device e.g. a server. In a further configuration the server may determine the amount of time the patient has used the respiratory device based on the amount of time or amount of times the patient is detected as attached. The controller or server may determine a patient as being compliant to therapy (e.g. high flow therapy) if the patient is detected as attached for a predetermined period of time. The patient detection method is used to determine compliance to therapy i.e. adherence to therapy. The patient being detected as attached can be used to determine usage of the respiratory device by the patient. This usage information or compliance information can be shared with or accessed by medical professionals via either the respiratory device or via the server.

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

DETAILED DESCRIPTION

Although certain examples are described below, those of skill in the art will appreciate that the disclosure extends beyond the specifically disclosed examples and/or uses and obvious modifications and equivalents thereof. Thus, it is intended that the scope of the disclosure herein disclosed should not be limited by any particular examples described below.

Overview of Example Respiratory System

Figure 1:
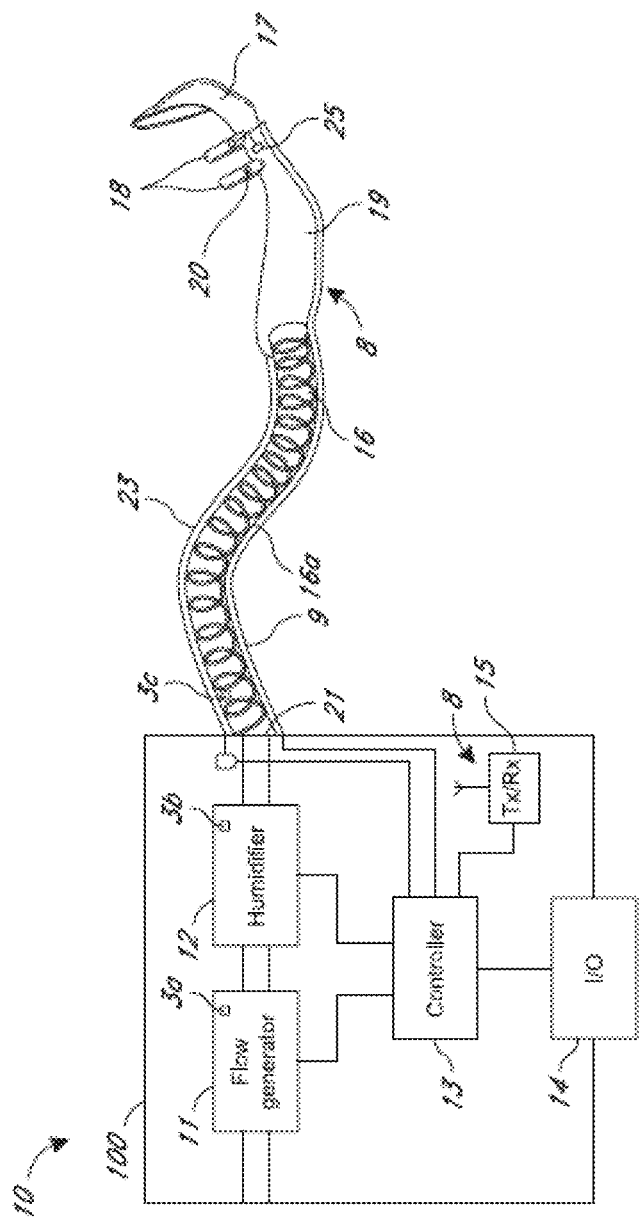
FIG. 1 shows schematically a respiratory system configured to provide a respiratory therapy to a patient.
Figure 2:
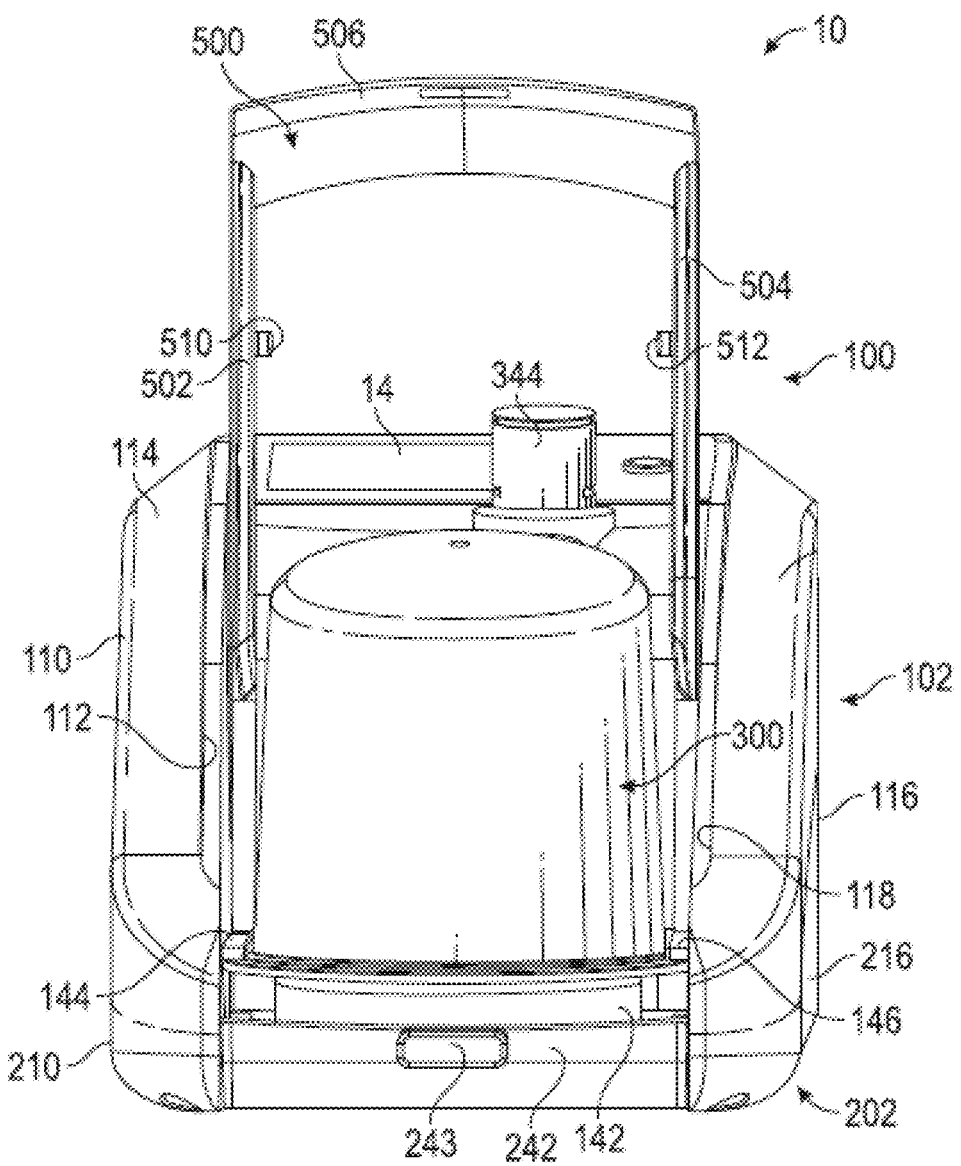
FIG. 2 is a front view of an example respiratory device with a humidification chamber in position and a raised handle/lever.
Figure 3:
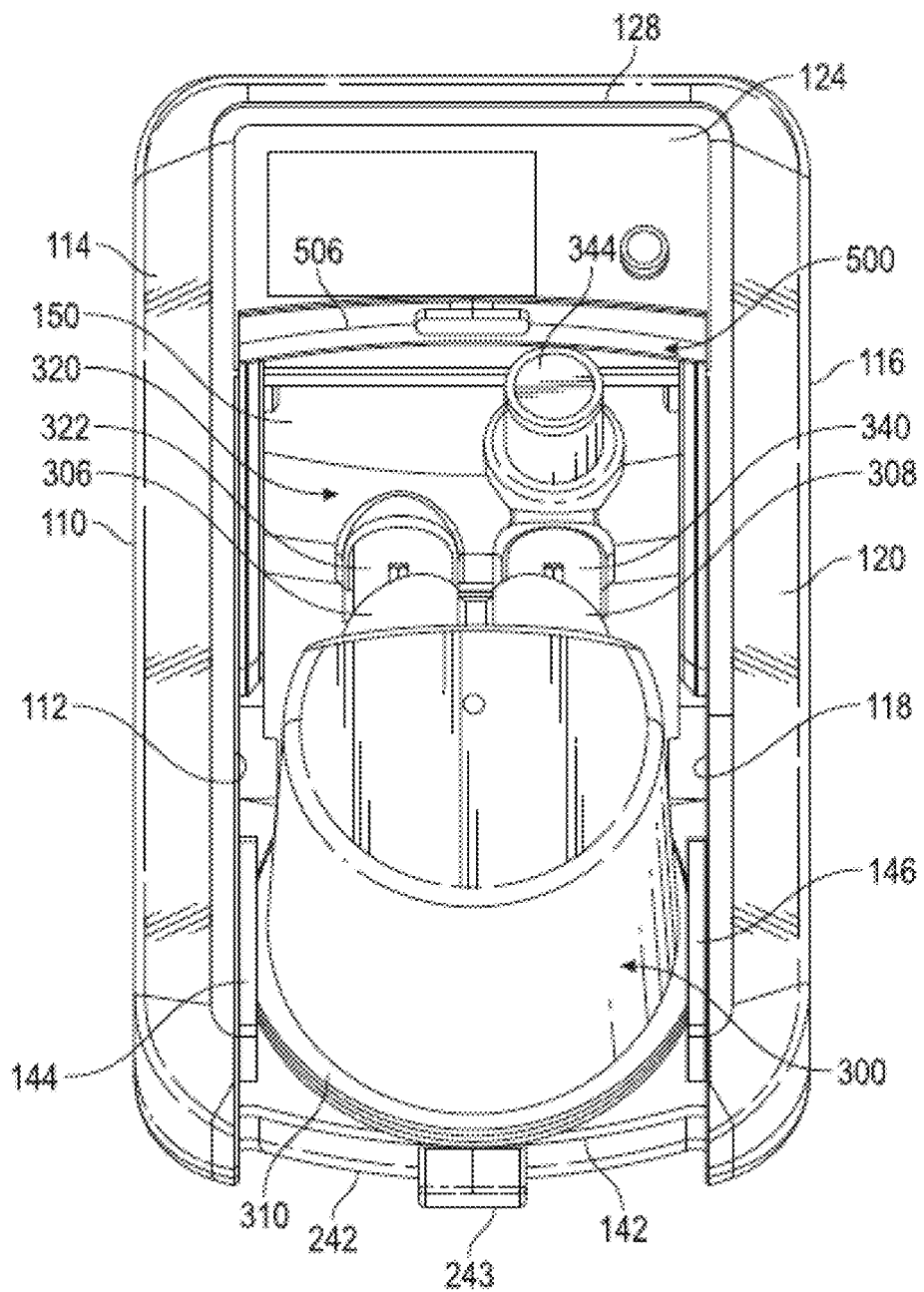
FIG. 3 is a top view corresponding to FIG. 2.
Figure 4:
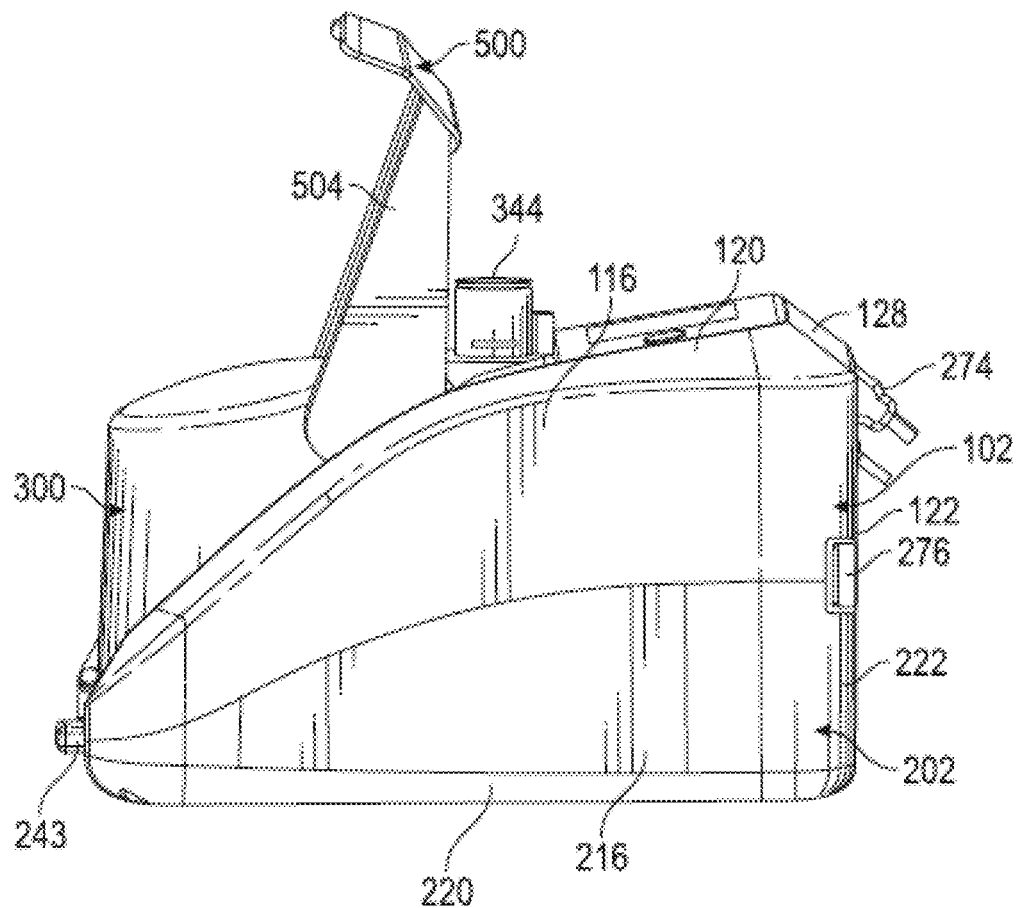
FIG. 4 is a right side view corresponding to FIG. 2.
Figure 5:
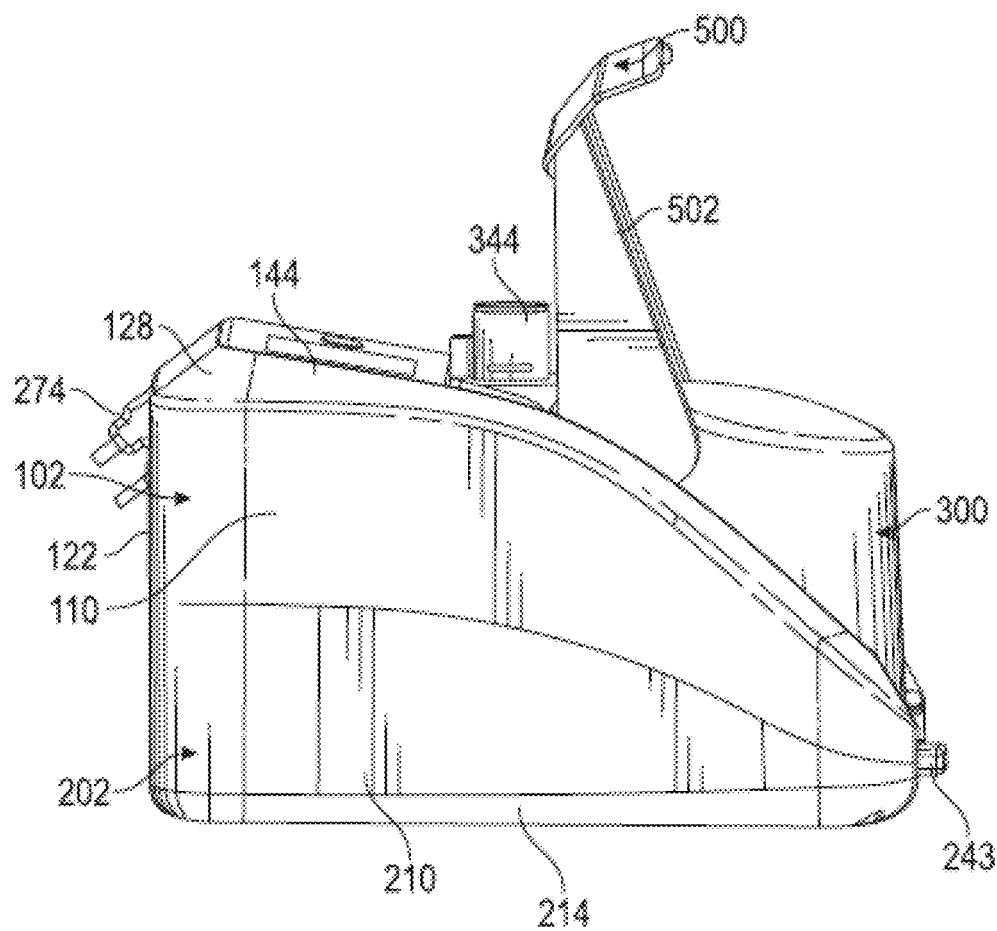
FIG. 5 is a left side view corresponding to FIG. 2.
Figure 6:
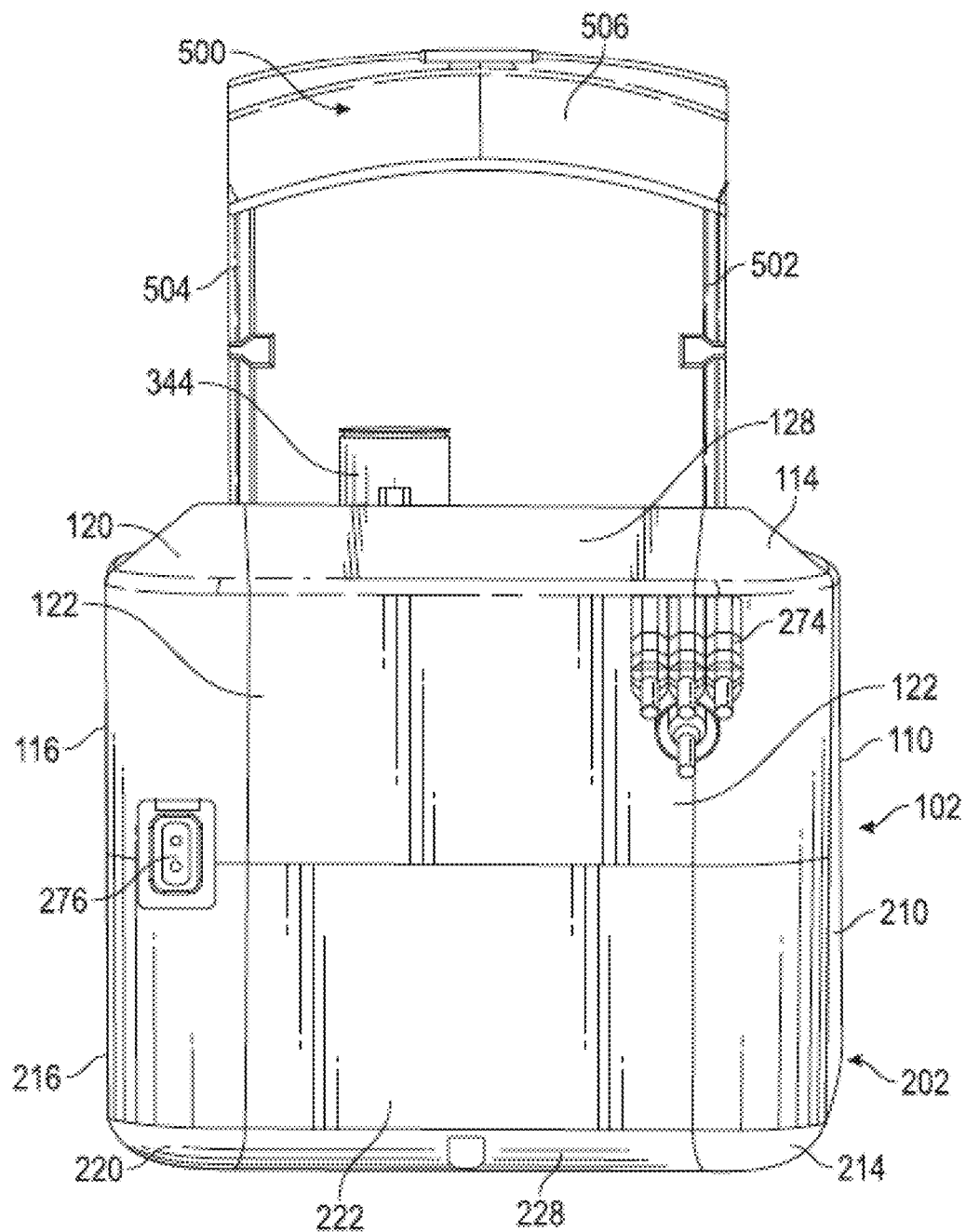
FIG. 6 is a rear view corresponding to FIG. 2.
Figure 7:
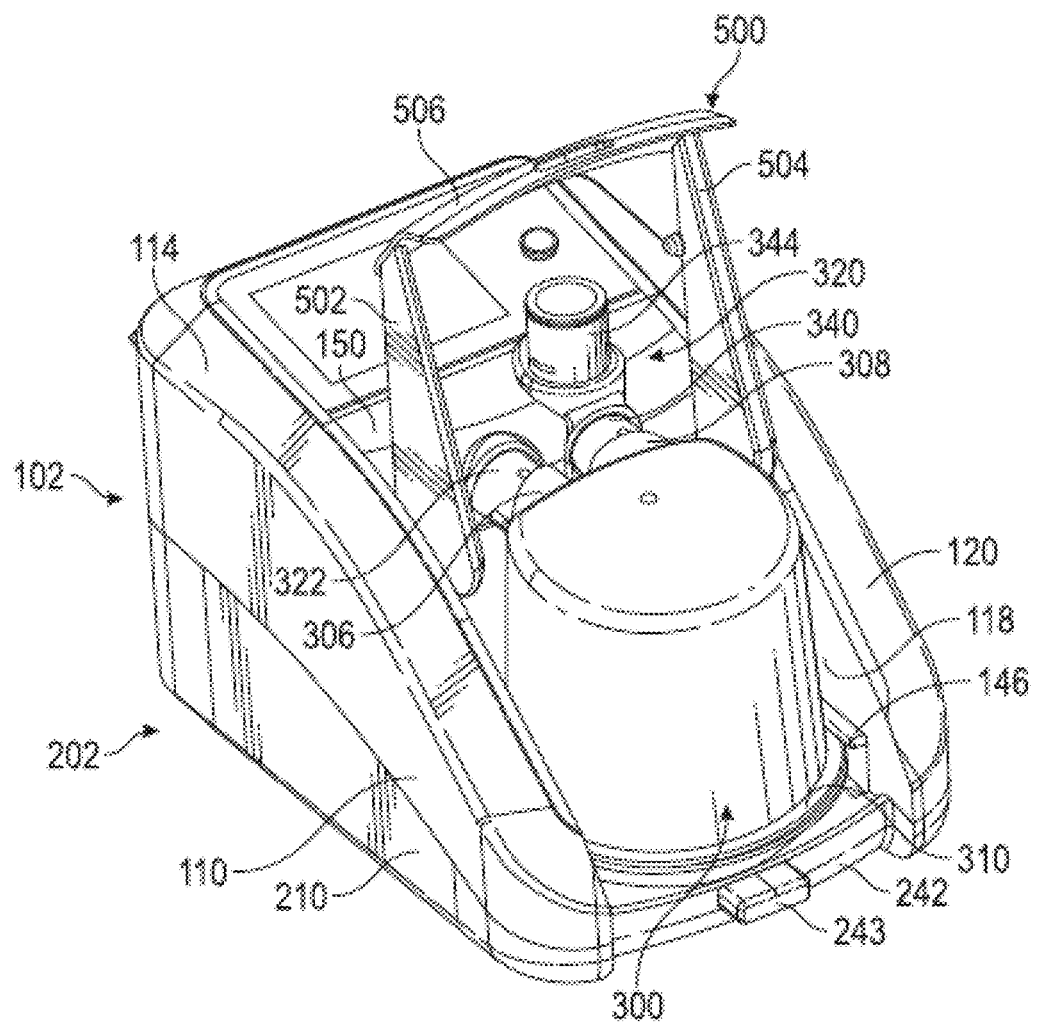
FIG. 7 is a front left perspective view corresponding to FIG. 2.

A schematic representation of a respiratory system 10 is provided in FIG. 1. The respiratory system 10 can include a main device housing 100. The main device housing 100 can contain a flow generator 11 that can be in the form of a motor/impeller arrangement, an optional humidifier or humidification chamber 12, a controller 13, and a user interface 14. The user interface 14 can include a display and input device(s) such as button(s), a touch screen, a combination of a touch screen and button(s), or the like. The controller 13 can include one or more hardware and/or software processors and can be configured or programmed to control the components of the system, including but not limited to operating the flow generator 11 to create a flow of gases for delivery to a patient, operating the humidifier or humidification chamber 12 (if present) to humidify and/or heat the gases flow, receiving user input from the user interface 14 for reconfiguration and/or user-defined operation of the respiratory system 10, and outputting information (for example on the display) to the user. The user can be a patient, healthcare professional, or others.

With continued reference to FIG. 1, a patient breathing conduit 16 can be coupled to a gases flow outlet 21 in the main device housing 100 of the respiratory system 10, and be coupled to a patient interface 17, such as a non-sealing interface like a nasal cannula with a manifold 19 and nasal prongs 18. The patient breathing conduit 16 can also be coupled to a face mask, a nasal mask, a nasal pillow mask, an endotracheal tube, a tracheostomy interface, or others.

The gases flow can be generated by the flow generator 11, and may be humidified, before being delivered to the patient via the patient breathing conduit 16 through the patient interface 17. The controller 13 can control the flow generator 11 to generate a gases flow of a desired flow rate, and/or one or more valves to control mixing of air and oxygen or other breathable gas. The controller 13 can control a heating element in the humidification chamber 12, if present, to heat the gases to a desired temperature that achieves a desired level of temperature and/or humidity for delivery to the patient. The patient breathing conduit 16 can have a heating element 16a, such as a heater wire, to heat gases flow passing through to the patient. The heating element 16a can also be under the control of the controller 13.

The system 10 can use ultrasonic transducer(s), flow sensor(s) such as a thermistor flow sensor, pressure sensor (s), temperature sensor(s), humidity sensor(s), or other sensors, in communication with the controller 13, to monitor characteristics of the gases flow and/or operate the system 10 in a manner that provides suitable therapy. The gases flow characteristics can include gases concentration, flow rate, pressure, temperature, humidity, or others. The sensors 3a, 3b, 3c, 20, 25, such as pressure, temperature, humidity, and/or flow sensors, can be placed in various locations in the main device housing 100, the patient conduit 16, and/or the patient interface 17. The controller 13 can receive output from the sensors to assist it in operating the respiratory system 10 in a manner that provides suitable therapy, such as to determine a suitable target temperature, flow rate, and/or pressure of the gases flow. Providing suitable therapy can include meeting a patient's inspiratory demand.

The system 10 can include a wireless data transmitter and/or receiver, or a transceiver 15 to enable the controller 13 to receive data signals 8 in a wireless manner from the operation sensors and/or to control the various components of the system 10. Additionally, or alternatively, the data transmitter and/or receiver 15 can deliver data to a remote server or enable remote control of the system 10. The system 10 can include a wired connection, for example, using cables or wires, to enable the controller 13 to receive data signals 8 from the operation sensors and/or to control the various components of the system 10.

The respiratory system 10 may comprise a high flow therapy apparatus. High flow therapy as discussed herein is intended to be given its typical ordinary meaning, as understood by a person of skill in the art, which generally refers to a respiratory system delivering a targeted flow of humidified respiratory gases via an intentionally unsealed patient interface with flow rates generally intended to meet or exceed inspiratory flow of a user. Typical patient interfaces include, but are not limited to, a nasal or tracheal patient interface. Typical flow rates for adults often range from, but are not limited to, about fifteen liters per minute to about sixty liters per minute or greater. Typical flow rates for pediatric users (such as neonates, infants and children) often range from, but are not limited to, about one liter per minute per kilogram of user weight to about three liters per minute per kilogram of user weight or greater. High flow therapy can also optionally include gas mixture compositions including supplemental oxygen and/or administration of therapeutic medicaments. High flow therapy is often referred to as nasal high flow (NHF), humidified high flow nasal cannula (HHFNC), high flow nasal oxygen (HFNO), high flow therapy (HFT), or tracheal high flow (THF), among other common names. For example, in some configurations, for an adult patient 'high flow therapy' may refer to the delivery of gases to a patient at a flow rate of greater than or equal to about 10 litres per minute (10 LPM), such as between about 10 LPM and about 100 LPM, or between about 15 LPM and about 95 LPM, or between about 20 LPM and about 90 LPM, or between about 25 LPM and about 85 LPM, or between about 30 LPM and about 80 LPM, or between about 35 LPM and about 75 LPM, or between about 40 LPM and about 70 LPM, or between about 45 LPM and about 65 LPM, or between about 50 LPM and about 60 LPM. In some configurations, for a neonatal, infant, or child patient 'high flow therapy' may refer to the delivery of gases to a patient at a flow rate of greater than 1 LPM, such as between about 1 LPM and about 25 LPM, or between about 2 LPM and about 25 LPM, or between about 2 LPM and about 5 LPM, or between about 5 LPM and about 25 LPM, or between about 5 LPM and about 10 LPM, or between about 10 LPM and about 25 LPM, or between about 10 LPM and about 20 LPM, or between about 10 LPM and 15 LPM, or between about 20 LPM and 25 LPM. A high flow therapy apparatus with an adult patient, a neonatal, infant, or child patient, may deliver gases to the patient at a flow rate of between about 1 LPM and about 100 LPM, or at a flow rate in any of the sub-ranges outlined above.

High flow therapy can be effective in meeting or exceeding the patient's inspiratory demand, increasing oxygenation of the patient and/or reducing the work of breathing. Additionally, high flow therapy may generate a flushing effect in the nasopharynx such that the anatomical dead space of the upper airways is flushed by the high incoming gases flow. The flushing effect can create a reservoir of fresh gas available of each and every breath, while minimizing re-breathing of carbon dioxide, nitrogen, etc.

The patient interface for use in a high flow therapy can be a non-sealing interface to prevent barotrauma, which can include tissue damage to the lungs or other organs of the patient's respiratory system due to difference in pressure relative to the atmosphere. The patient interface can be a nasal cannula with a manifold and nasal prongs, and/or a face mask, and/or a nasal pillows mask, and/or a nasal mask, and/or a tracheostomy interface, or any other suitable type of patient interface.

Figure 15:
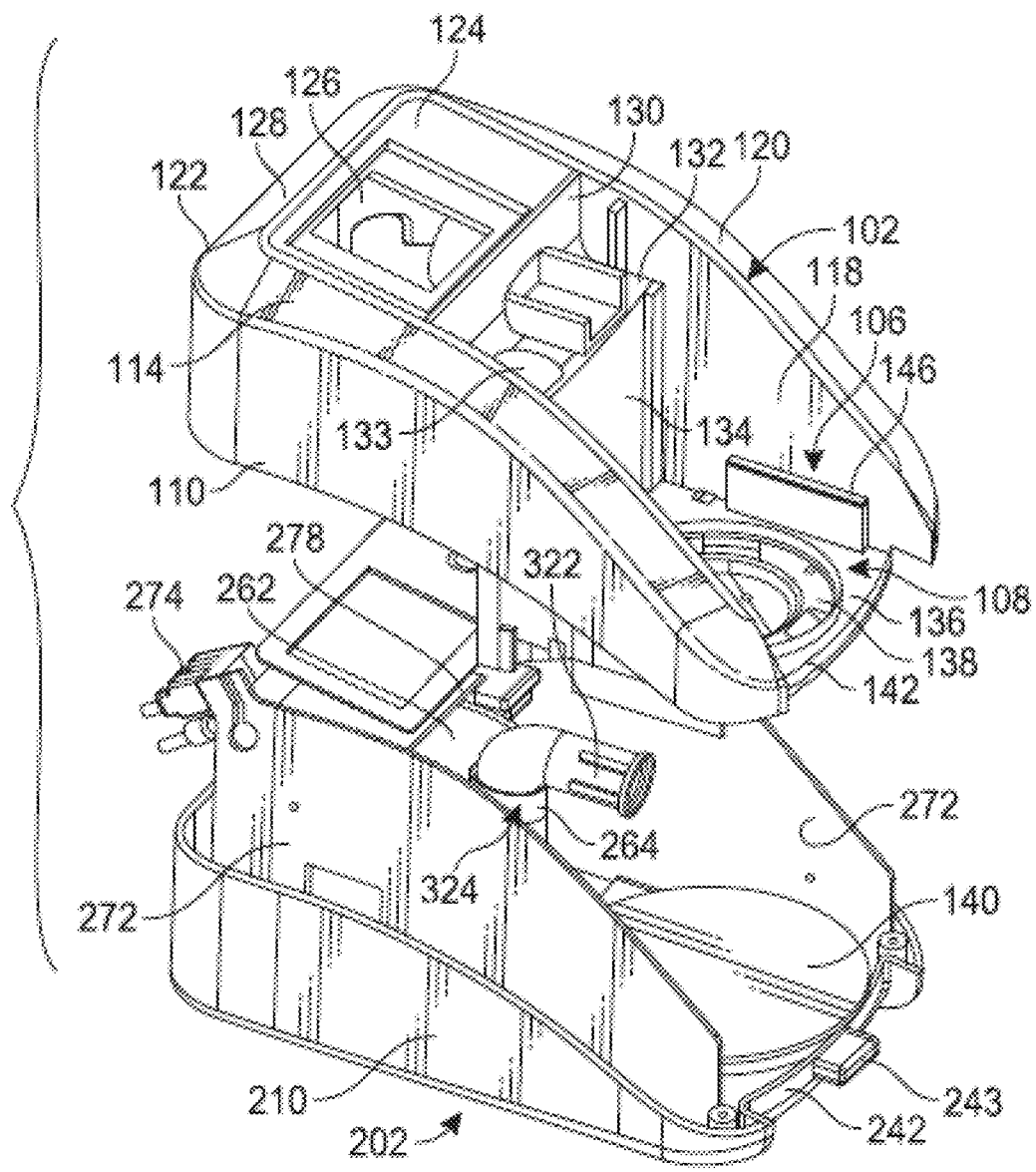
FIG. 15 is an exploded view of upper and lower chassis components of a main housing of the respiratory device.
Figure 16:
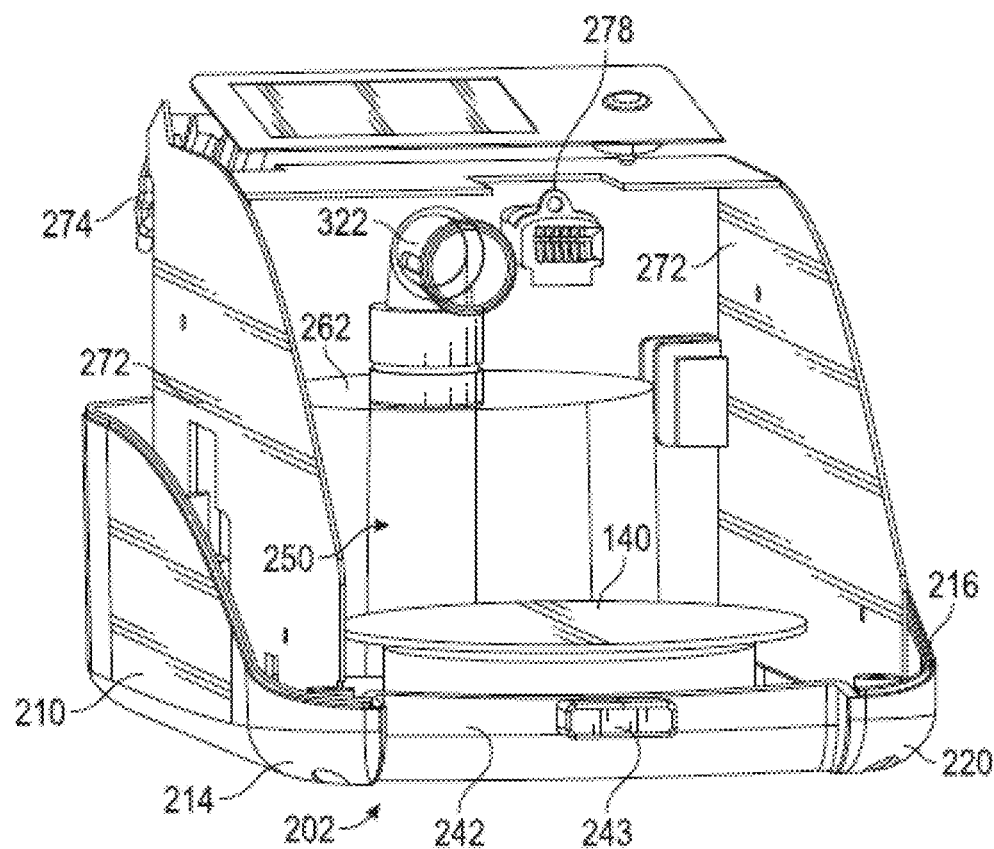
FIG. 16 is a front left side perspective view of the lower chassis of the main housing showing a housing for receipt of a motor/sensor module sub-assembly.

FIGS. 2 to 17B show an example respiratory device of the respiratory system 10 having a main housing 100. The main housing 100 has a main housing upper chassis 102 and a main housing lower chassis 202. The main housing upper chassis 102 has a peripheral wall arrangement 106 (see FIG. 15). The peripheral wall arrangement defines a humidifier or humidification chamber bay 108 for receipt of a removable humidification chamber 300. The removable humidification chamber 300 contains a suitable liquid such as water for humidifying gases that can be delivered to a patient.

In the form shown, the peripheral wall arrangement 106 of the main housing upper chassis 102 can include a substantially vertical left side outer wall 110 that is oriented in a front-to-rear direction of the main housing 100, a substantially vertical left side inner wall 112 that is oriented in a front-to-rear direction of the main housing 100, and an interconnecting wall 114 that extends between and interconnects the upper ends of the left side inner and outer walls 110, 112. The main housing upper chassis 102 can further include a substantially vertical right side outer wall 116 that is oriented in a front-to-rear direction of the main housing 100, a substantially vertical right side inner wall 118 that is oriented in a front-to-rear direction of the main housing 100, and an interconnecting wall 120 that extends between and interconnects the upper ends of the right side inner and outer walls 116, 118. The interconnecting walls 114, 120 are angled towards respective outer edges of the main housing 100, but can alternatively be substantially horizontal or inwardly angled.

The main housing upper chassis 102 can further include a substantially vertical rear outer wall 122. An upper part of the main housing upper chassis 102 can include a forwardly angled surface 124. The surface 124 can have a recess 126 for receipt of a display and user interface module 14. The display can be configured to display characteristics of sensed gas(es) in real time. The system can display the patient detection status of the patient interface. If the patient is not detected, the controller may not output or can stop outputting the respiratory rate value(s) and/or other parameters for display. The controller can also optionally output a message for display that no patient is detected at block 2708. An example of the message can be a "--" icon. An interconnecting wall 128 can extend between and interconnect the upper end of the rear outer wall 122 and the rear edge of the surface 124.

A substantially vertical wall portion 130 can extend downwardly from a front end of the surface 124. A substantially horizontal wall portion 132 can extend forwardly from a lower end of the wall portion 130 to form a ledge. A substantially vertical wall portion 134 can extend downwardly from a front end of the wall portion 132 and terminate at a substantially horizontal floor portion 136 of the humidification chamber bay 108. The left side inner wall 112, right side inner wall 118, wall portion 134, and floor portion 136 together can define the humidification chamber bay 108. The floor portion 136 of the humidification chamber bay 108 can have a recess 138 to receive a heater arrangement such as a heater plate 140 or other suitable heating element(s) for heating liquid in the humidification chamber 300 for use during a humidification process.

The main housing lower chassis 202 can be attachable to the upper chassis 102, either by suitable fasteners or integrated attachment features such as clips for example. The main housing lower chassis 202 can include a substantially vertical left side outer wall 210 that is oriented in a front-to-rear direction of the main housing 100 and is contiguous with the left side outer wall 110 of the upper chassis 102, and a substantially vertical right side outer wall 216 that is oriented in a front-to-rear direction of the main housing 100 and is contiguous with the right side outer wall 116 of the upper chassis 102. The main housing lower chassis 202 can further include a substantially vertical rear outer wall 222 that is contiguous with the rear outer wall 122 of the upper chassis 102.

The lower housing chassis 202 can have a lip 242 that is contiguous with the lip 142 of the upper housing chassis 102, and also forms part of the recess for receiving the handle portion 506 of the lever 500. The lower lip 242 can include a forwardly directed protrusion 243 that acts as a retainer for the handle portion 506 of the lever 500. Instead of the lever 500, the system can have a spring-loaded guard to retain the humidification chamber 300 in the humidification chamber bay 108.

An underside of the lower housing chassis 202 can include a bottom wall 230. Respective interconnecting walls 214, 220, 228 can extend between and interconnect the substantially vertical walls 210, 216, 222 and the bottom wall 230. The bottom wall 230 can include a grill 232 comprising a plurality of apertures to enable drainage of liquid in case of leakage from the humidification chamber 300 (e.g. from spills). The bottom wall 230 additionally can include elongated forward-rearward oriented slots 234. The slots 234 can additionally enable drainage of liquid in case of leakage from the humidification chamber 300, without the liquid entering the electronics housing. In the illustrated configuration, the slots 234 can be wide and elongate relative to the apertures of the grill 232 to maximize the drainage of liquid.

Figure 17:
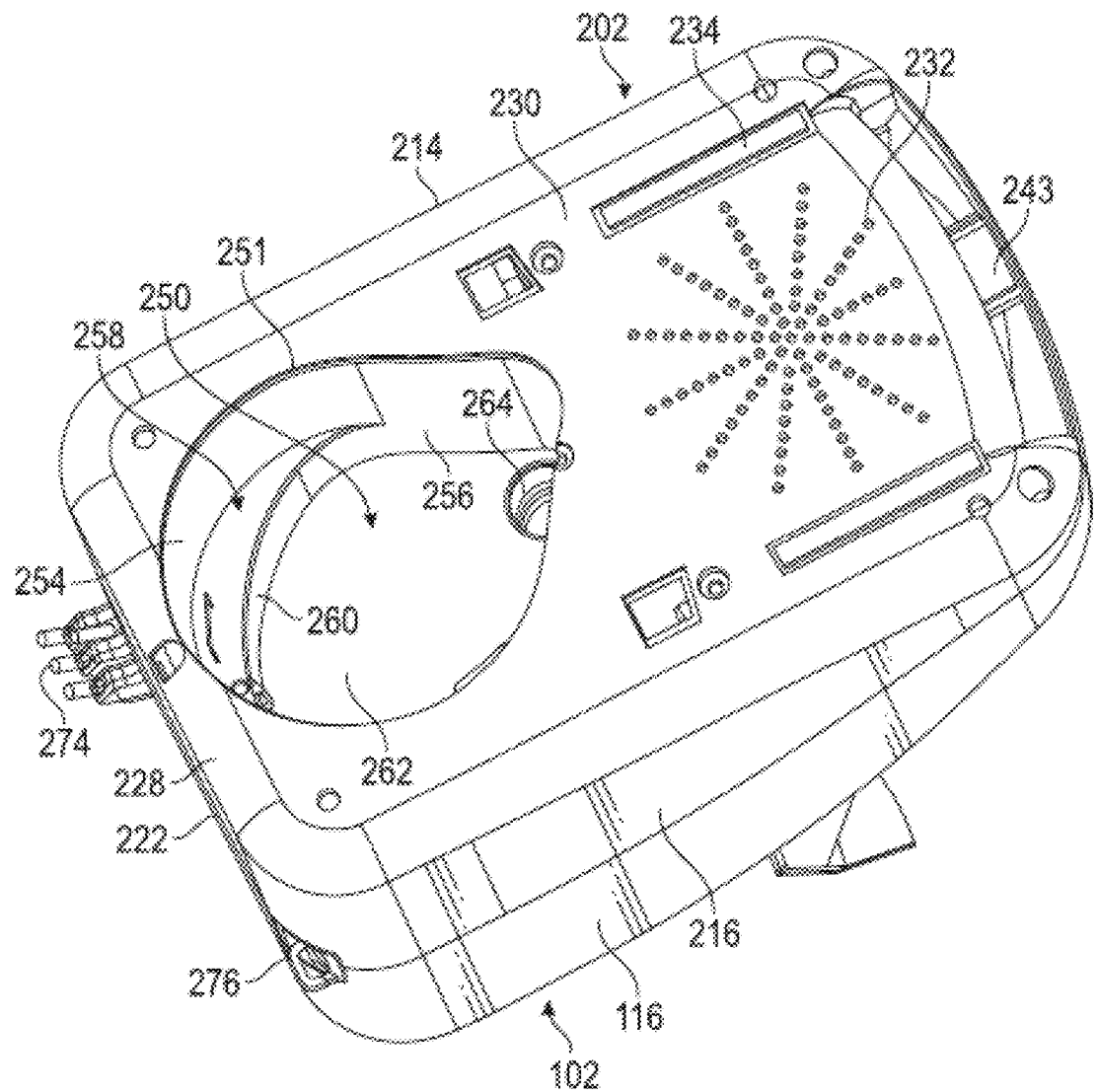
FIG. 17 is a first underside perspective view of the main housing of the respiratory device showing a recess inside the housing for the motor/sensor module sub-assembly.
Figure 18:
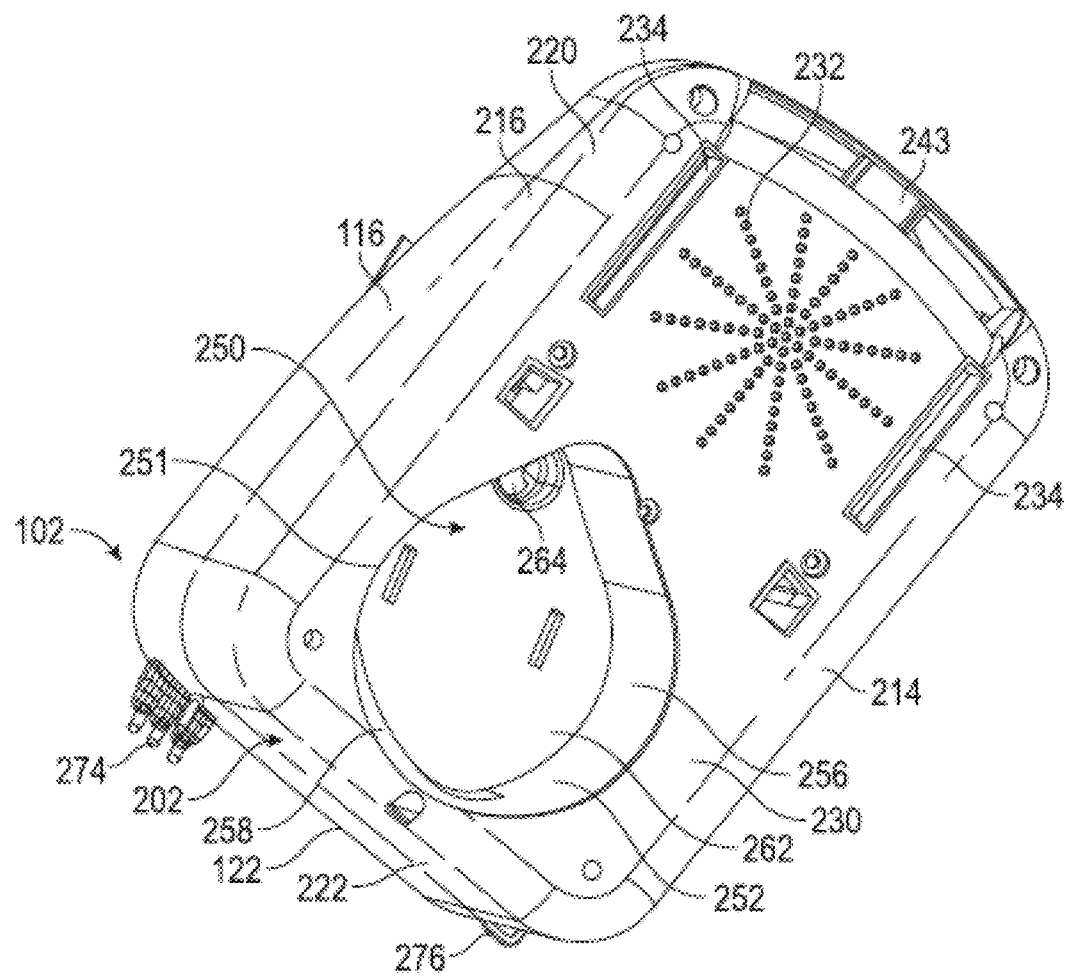
FIG. 18 is a second underside perspective view of the main housing of the respiratory device showing the recess for the motor/sensor module sub-assembly.

As shown in FIGS. 17 to 18, the lower chassis 202 can have a motor recess 250 for receipt of a motor and sensor module. The motor and sensor module may be non-removable from the main housing 100. The motor and sensor module can be removable from the main housing 100, as illustrated in FIGS. 17-18. A recess opening 251 can be provided in the bottom wall 230 adjacent a rear edge thereof, for receipt of a motor/sensor module. A continuous, gas impermeable, unbroken peripheral wall 252 can be integrally formed with the bottom wall 230 of the lower chassis 202 and extend upwardly from the periphery of the opening 251. A rearward portion 254 of the peripheral wall 252 has a first height, and a forward portion 256 of the peripheral wall 252 has a second height that is greater than the first height. The rearward portion 254 of the peripheral wall 252 terminates at a substantially horizontal step 258, which in turn terminates at an upper auxiliary rearward portion 260 of the peripheral wall 252. The forward portion 256 and upper auxiliary rearward portion 260 of the peripheral wall 252 terminate at a ceiling 262. All of the walls and the ceiling 262 can be continuous, gas impermeable, and unbroken other than the gases flow passage. Therefore, the entire motor recess 250 can be gas impermeable and unbroken, other than the gases flow passage.

The motor and sensor module can be insertable into the recess 250 and attachable to the lower chassis 202. Upon insertion of the motor and sensor module into the lower chassis 202, the gases flow passage tube 264 can extend through the downward extension tube 133 and be sealed by the soft seal.

The humidification chamber 300 can be fluidly coupled to the apparatus 10 in a linear slide-on motion in a rearward direction of the humidification chamber 300 into the chamber bay 108, from a position at the front of the housing 100 in a direction toward the rear of the housing 100. A gases outlet port 322 can be in fluid communication with the motor.

Figure 8:
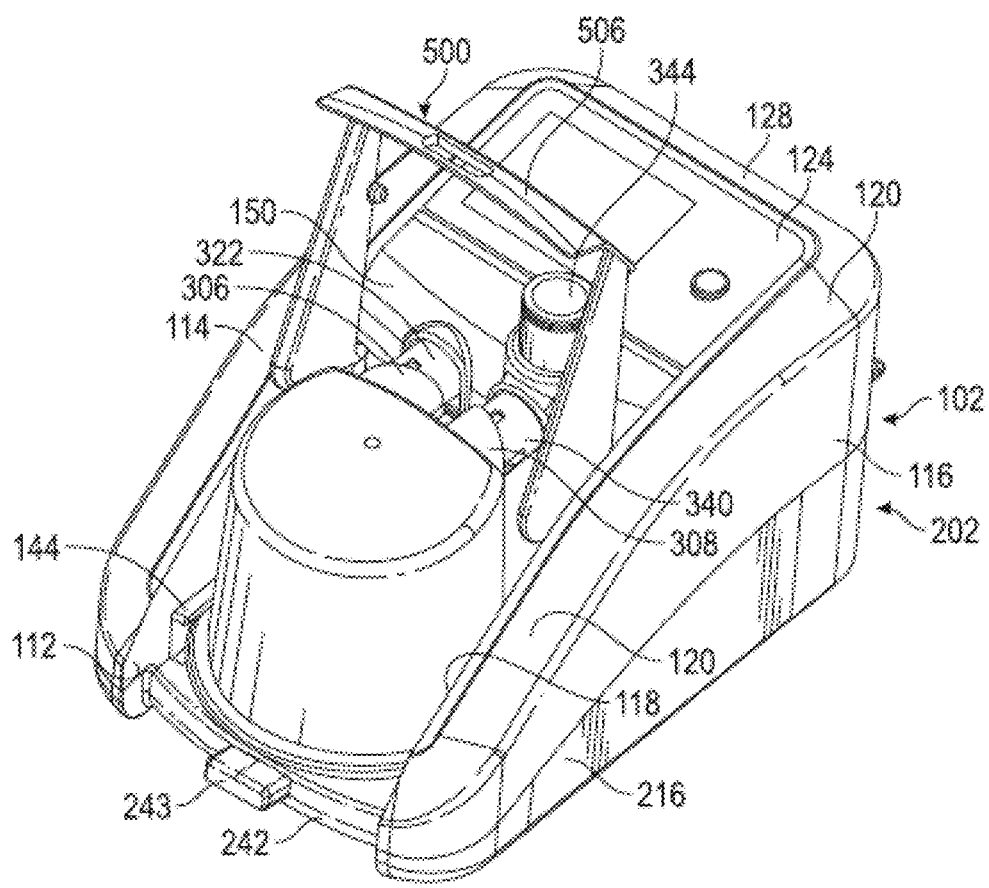
FIG. 8 is a front right perspective view corresponding to FIG. 2.
Figure 9:
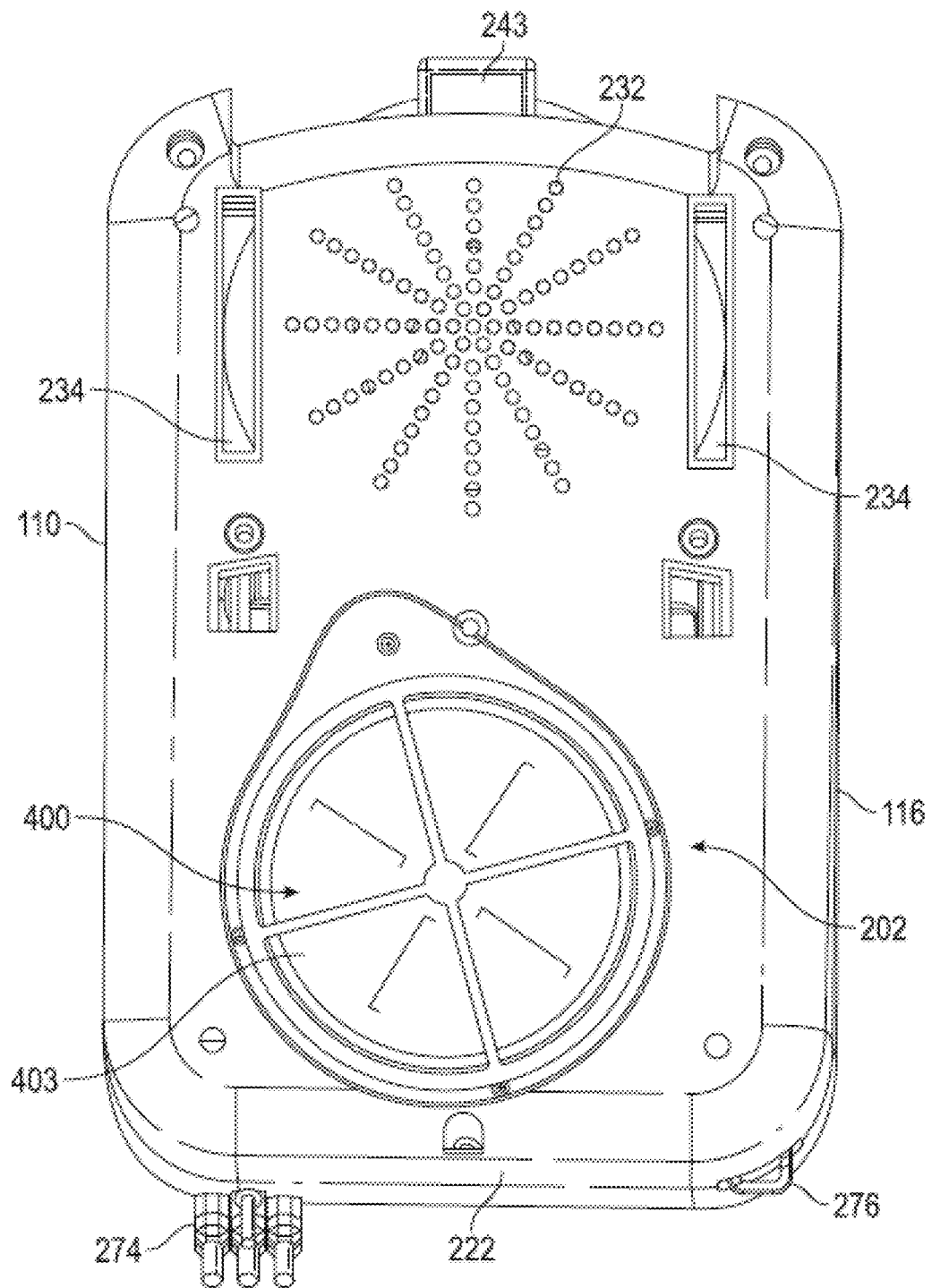
FIG. 9 is a bottom view corresponding to FIG. 2.

A gases inlet port 340 (humidified gases return) as shown in FIG. 8 can include a removable L-shaped elbow. The removable elbow can further include a patient outlet port 344 for coupling to the patient conduit 16 to deliver gases to the patient interface. The gases outlet port 322, gases inlet port 340, and patient outlet port 344 each can have soft seals such as O-ring seals or T-seals to provide a sealed gases passageway between the apparatus 10, the humidification chamber 300, and the patient conduit 16.

The humidification chamber gases inlet port 306 can be complementary with the gases outlet port 322, and the humidification chamber gases outlet port 308 can be complementary with the gases inlet port 340. The axes of those ports can be parallel to each other to enable the humidification chamber 300 to be inserted into the chamber bay 108 in a linear movement.

Figure 10:
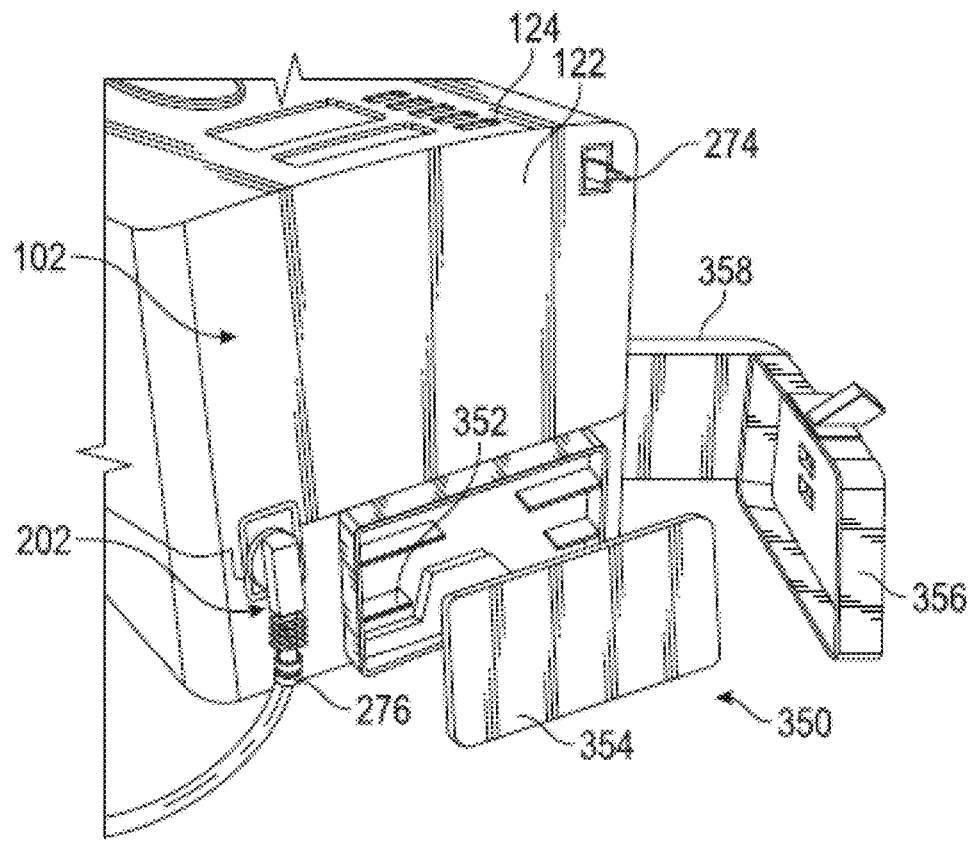
FIG. 10 shows an example configuration of an air and oxygen inlet arrangement of a respiratory device.
Figure 11:
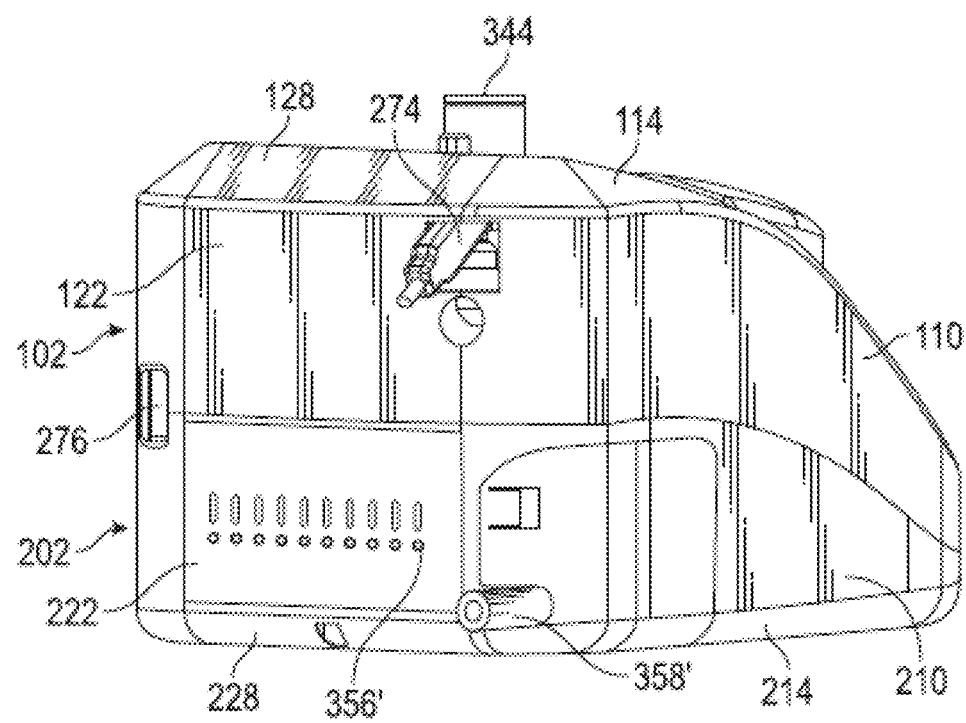
FIG. 11 shows another example configuration of an air and oxygen inlet arrangement of the respiratory device.
Figure 12:
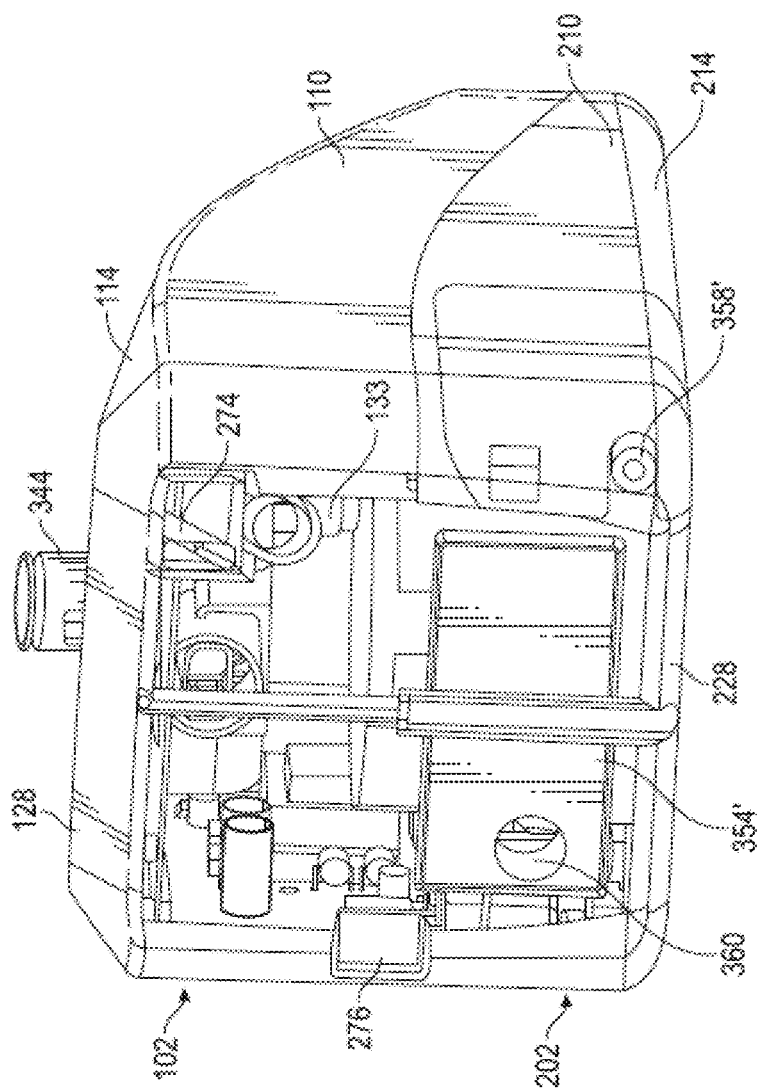
FIG. 12 is a transverse sectional view showing further detail of the air and oxygen inlet arrangement of FIG. 11.
Figure 13:
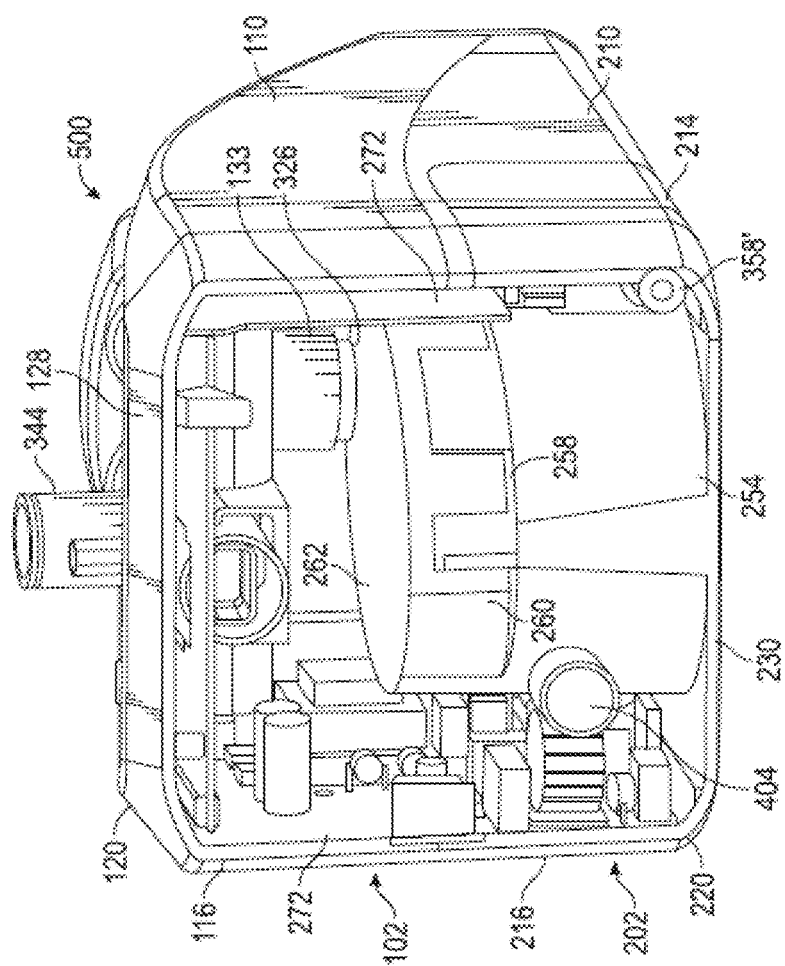
FIG. 13 is another transverse sectional view showing further detail of the air and oxygen inlet arrangement of FIG. 11.
Figure 14:
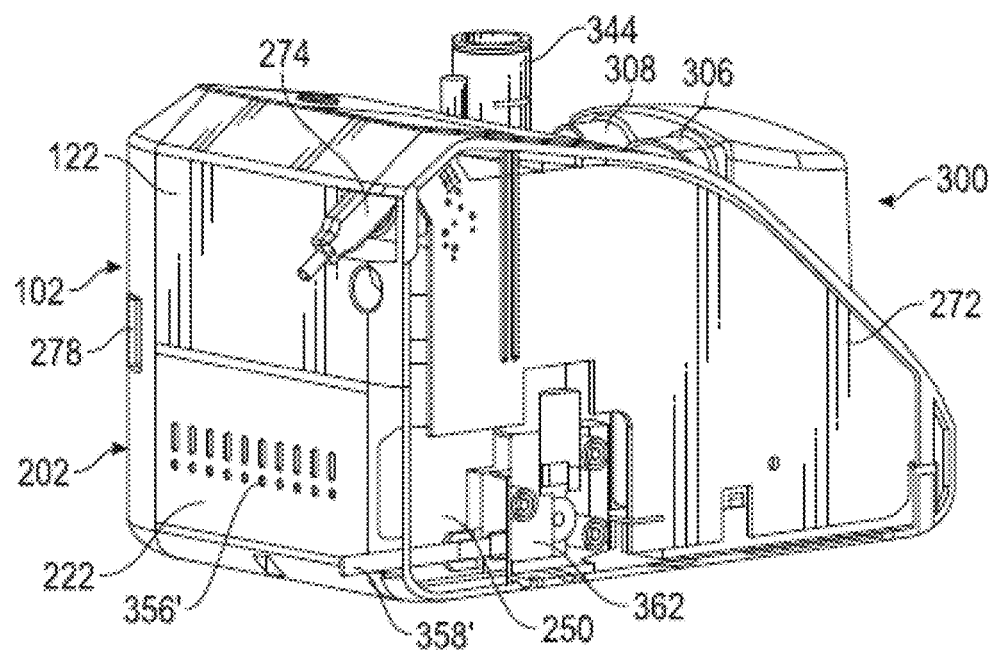
FIG. 14 is a longitudinal sectional view showing further detail of the air and oxygen inlet arrangement of FIG. 11.

The respiratory device can have air and oxygen (or alternative auxiliary gas) inlets in fluid communication with the motor to enable the motor to deliver air, oxygen (or alternative auxiliary gas), or a mixture thereof to the humidification chamber 300 and thereby to the patient. As shown in FIG. 10, the device can have a combined air/oxygen (or alternative auxiliary gas) inlet arrangement 350. This arrangement can include a combined air/oxygen port 352 into the housing 100, a filter 354, and a cover 356 with a hinge 358. A gases tube can also optionally extend laterally or in another appropriate direction and be in fluid communication with an oxygen (or alternative auxiliary gas) source. The port 352 can be fluidly coupled with the motor 402. For example, the port 352 may be coupled with the motor/sensor module 400 via a gases flow passage between the port 352 and an inlet aperture or port in the motor and sensor module 400, which in turn would lead to the motor.

The device can have the arrangement shown in FIGS. 11 to 14 to enable the motor to deliver air, oxygen (or alternative auxiliary gas), or a suitable mixture thereof to the humidification chamber 300 and thereby to the patient. This arrangement can include an air inlet 356' in the rear wall 222 of the lower chassis 202 of the housing 100. The air inlet 356' comprises a rigid plate with a suitable grill arrangement of apertures and/or slots. Sound dampening foam may be provided adjacent the plate on the interior side of the plate. An air filter box 354' can be positioned adjacent the air inlet 356' internally in the main housing 100, and include an air outlet port 360 to deliver filtered air to the motor via an air inlet port 404 in the motor/sensor module 400. The air filter box 354' may include a filter configured to remove particulates (e.g. dust) and/or pathogens (e.g. viruses or bacteria) from the gases flow. A soft seal such as an O-ring seal can be provided between the air outlet port 360 and air inlet port 404 to seal between the components. The device can include a separate oxygen inlet port 358' positioned adjacent one side of the housing 100 at a rear end thereof, the oxygen port 358' for receipt of oxygen from an oxygen source such as a tank or source of piped oxygen. The oxygen inlet port 358' is in fluid communication with a valve 362. The valve 362 can suitably be a solenoid valve that enables the control of the amount of oxygen that is added to the gases flow that is delivered to the humidification chamber 300. The oxygen port 358' and valve 362 may be used with other auxiliary gases to control the addition of other auxiliary gases to the gases flow. The other auxiliary gases can include any one or more of a number of gases useful for gas therapy, including but not limited to heliox and nitric oxide.

As shown in FIGS. 13 to 16, the lower housing chassis 202 can include suitable electronics boards, such as sensing circuit boards. The electronics boards can be positioned adjacent respective outer side walls 210, 216 of the lower housing chassis 202. The electronics boards can contain, or can be in electrical communication with, suitable electrical or electronics components, such as but not limited to microprocessors, capacitors, resistors, diodes, operational amplifiers, comparators, and switches. Sensors can be used with the electronic boards. Components of the electronics boards (such as but not limited to one or more microprocessors) can act as the controller 13 of the apparatus.

One or both of the electronics boards can be in electrical communication with the electrical components of the apparatus 10, including the display unit and user interface 14, motor, valve 362, and the heater plate 140 to operate the motor to provide the desired flow rate of gases, operate the humidification chamber 300 to humidify and heat the gases flow to an appropriate level, and supply appropriate quantities of oxygen (or quantities of an alternative auxiliary gas) to the gases flow.

The electronics boards can be in electrical communication with a connector arrangement 274 projecting from the rear wall 122 of the upper housing chassis 102. The connector arrangement 274 may be coupled to an alarm, pulse oximetry port, and/or other suitable accessories. The electronics boards can also be in electrical communication with an electrical connector 276 that can also be provided in the rear wall 122 of the upper housing chassis 102 to provide mains or battery power to the components of the device.

As mentioned above, operation sensors, such as flow, temperature, humidity, and/or pressure sensors can be placed in various locations in the respiratory device, the patient breathing conduit 16, and/or cannula 17 such as shown in FIG. 1. The electronics boards can be in electrical communication with those sensors. Output from the sensors can be received by the controller 13, to assist the controller 13 to operate the respiratory system 10 in a manner that provides optimal therapy, including meeting inspiratory demand.

As outlined above, the electronics boards and other electrical and electronic components can be pneumatically isolated from the gases flow path to improve safety. The sealing also prevents water ingress.

Control System

Figure 19A:
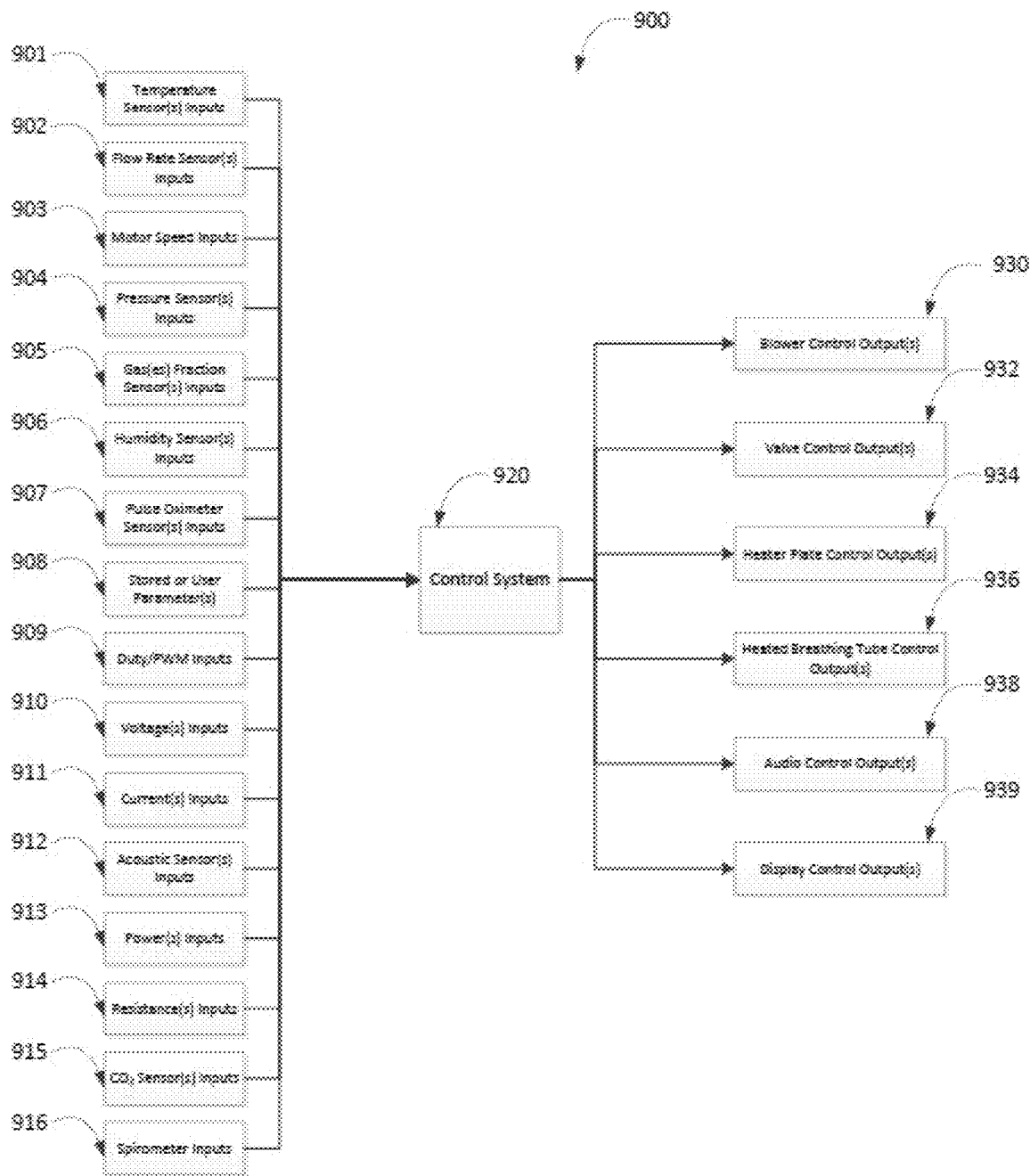
FIG. 19A illustrates a block diagram of a control system interacting with and/or providing control and direction to components of a respiratory system.

FIG. 19A illustrates a block diagram 900 of an example control system 920 (which can be the controller 13 in FIG. 1) that can detect patient conditions and control operation of the respiratory system including the gases source. The control system 920 can manage a flow rate of the gases flowing through the respiratory system as is the gases are delivered to a patient. For example, the control system 920 can increase or decrease the flow rate by controlling an output of a motor speed of the blower (hereinafter also referred to as a "blower motor") 930 or an output of a valve 932 in a blender. The control system 920 can automatically determine a set value or a personalized value of the flow rate for a particular patient as discussed below. The flow rate can be optimized by the control system 920 to improve patient comfort and therapy.

The control system 920 can also generate audio and/or display/visual outputs 938, 939. For example, the flow therapy apparatus can include a display and/or a speaker. The display can indicate to the physicians any warnings or alarms generated by the control system 920. The display can also indicate control parameters that can be adjusted by the physicians. For example, the control system 920 can automatically recommend a flow rate for a particular patient. The control system 920 can also determine a respiratory state of the patient, including but not limited to generating a respiratory rate of the patient, and send it to the display, which will be described in greater detail below.

The control system 920 can change heater control outputs to control one or more of the heating elements (for example, to maintain a temperature set point of the gases delivered to the patient). The control system 920 can also change the operation or duty cycle of the heating elements. The heater control outputs can include heater plate control output(s) 934 and heated breathing tube control output(s) 936.

The control system 920 can determine the outputs 930-939 based on one or more received inputs 901-916. The inputs 901-916 can correspond to sensor measurements received automatically by the controller 600 (shown in FIG. 19B). The control system 920 can receive sensor inputs including but not limited to temperature sensor(s) inputs 901, flow rate sensor(s) inputs 902, motor speed inputs 903, pressure sensor(s) inputs 904, gas(s) fraction sensor(s) inputs 905, humidity sensor(s) inputs 906, pulse oximeter (for example, SpO$_2$) sensor(s) inputs 907, stored or user parameter(s) 908, duty cycle or pulse width modulation (PWM) inputs 909, voltage(s) inputs 910, current(s) inputs 911, acoustic sensor(s) inputs 912, power(s) inputs 913, resistance(s) inputs 914, CO$_2$ sensor(s) inputs 915, and/or spirometer inputs 916. The control system 920 can receive inputs from the user or stored parameter values in a memory 624 (shown in FIG. 19B). The control system 920 can dynamically adjust flow rate for a patient over the time of their therapy. The control system 920 can continuously detect system parameters and patient parameters. A person of ordinary skill in the art will appreciate based on the disclosure herein that any other suitable inputs and/or outputs can be used with the control system 920.

Controller

Figure 19B:
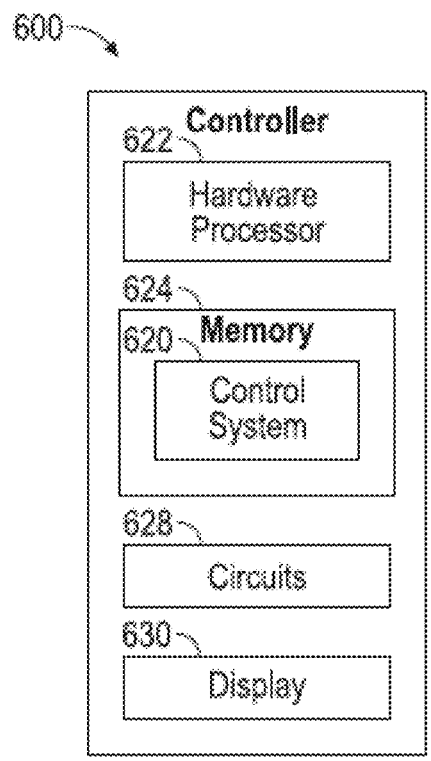
FIG. 19B illustrates a block diagram of an example controller.

FIG. 19B illustrates a block diagram of an embodiment of a controller 600 (which can be the controller 13 in FIG. 1). The controller 600 can include programming instructions for detection of input conditions and control of output conditions. The programming instructions can be stored in the memory 624 of the controller 600. The programming instructions can correspond to the methods, processes and functions described herein. The programming instructions can be executed by one or more hardware processors 622 of the controller 600. The programming instructions can be implemented in C, C++, JAVA, or any other suitable programming languages. Some or all of the portions of the programming instructions can be implemented in application specific circuitry 628 such as ASICs and FPGAs.

The controller 600 can also include circuits 628 for receiving sensor signals. The controller 600 can further include a display 630 for transmitting status of the patient and the respiratory assistance system. The display 630 can also show warnings and/or other alerts. The display 630 can be configured to display characteristics of sensed gas(es) in real time or otherwise. The controller 600 can also receive user inputs via the user interface such as display 630. The user interface can include button(s) and/or dial(s). The user interface can comprise a touch screen.

Motor and Sensor Module

Any of the features of the respiratory system described herein, including but not limited to the humidification chamber, the flow generator, the user interface, the controller, and the patient breathing conduit configured to couple the gases flow outlet of the respiratory system to the patient interface, can be combined with any of the sensor modules described herein.

Figure 20:
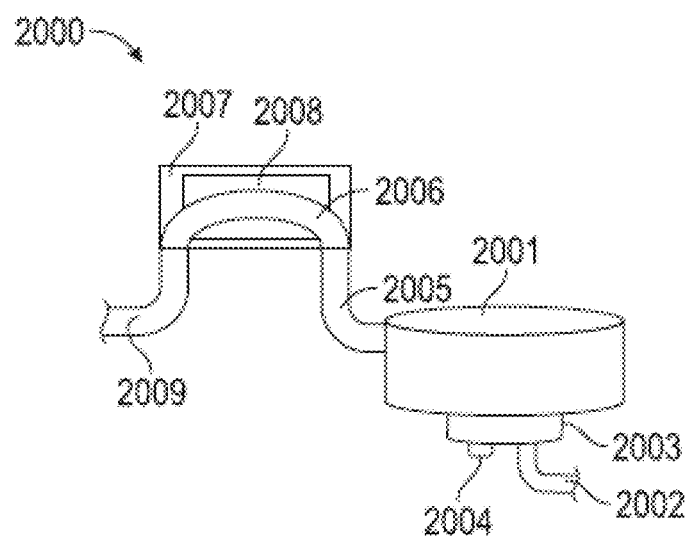
FIG. 20 illustrates a block diagram of a motor and sensor module.

FIG. 20 illustrates a block diagram of the motor and sensor module 2000, which can be received by the recess 250 in the respiratory device (shown in FIGS. 17 and 18). The motor and sensor module can include a blower 2001, which entrains room air to deliver to a patient. The blower 2001 can be a centrifugal blower.

One or more sensors (for example, Hall-effect sensors) may be used to measure a motor speed of the blower motor. The blower motor may comprise a brushless DC motor, from which motor speed can be measured without the use of separate sensors. For example, during operation of a brushless DC motor, back-EMF can be measured from the non-energized windings of the motor, from which a motor position can be determined, which can in turn be used to calculate a motor speed. In addition, a motor driver may be used to measure motor current, which can be used with the measured motor speed to calculate a motor torque. The blower motor may comprise a low inertia motor.

Room air can enter a room air inlet 2002, which enters the blower 2001 through an inlet port 2003. The inlet port 2003 can include a valve 2004 through which a pressurized gas may enter the blower 2001. The valve 2004 can control a flow of oxygen into the blower 2001. The valve 2004 can be any type of valve, including a proportional valve or a binary valve. In some embodiments, the inlet port does not include a valve.

The blower 2001 can operate at a motor speed of greater than 1,000 RPM and less than 30,000 RPM, greater than 2,000 RPM and less than 21,000 RPM, or between any of the foregoing values. Operation of the blower 2001 mixes the gases entering the blower 2001 through the inlet port 2003. Using the blower 2001 as the mixer can decrease the pressure drop that would otherwise occur in a system with a separate mixer, such as a static mixer comprising baffles, because mixing requires energy.

The mixed air can exit the blower 2001 through a conduit 2005 and enters the flow path 2006 in the sensor chamber 2007. A sensing circuit board with sensors 2008 can positioned in the sensor chamber 2007 such that the sensing circuit board is at least partially immersed in the gases flow. At least some of the sensors 2008 on the sensing circuit board can be positioned within the gases flow to measure gases properties within the flow. After passing through the flow path 2006 in the sensor chamber 2007, the gases can exit 2009 to the humidification chamber.

Positioning sensors 2008 downstream of the combined blower and mixer 2001 can increase accuracy of measurements, such as the measurement of gases fraction concentration, including oxygen concentration, over systems that position the sensors upstream of the blower and/or the mixer. Such a positioning can give a repeatable flow profile. Further, positioning the sensors downstream of the combined blower and mixer avoids the pressure drop that would otherwise occur, as where sensing occurs prior to the blower, a separate mixer, such as a static mixer with baffles, is required between the inlet and the sensing system. The mixer can introduce a pressure drop across the mixer. Positioning the sensing after the blower can allow the blower to be a mixer, and while a static mixer would lower pressure, in contrast, a blower increases pressure. Also, immersing at least part of the sensing circuit board and sensors 2008 in the flow path can increase the accuracy of measurements because the sensors being immersed in the flow means they are more likely to be subject to the same conditions, such as temperature and pressure, as the gases flow and therefore provide a better representation of the gases flow characteristics.

Figure 21:
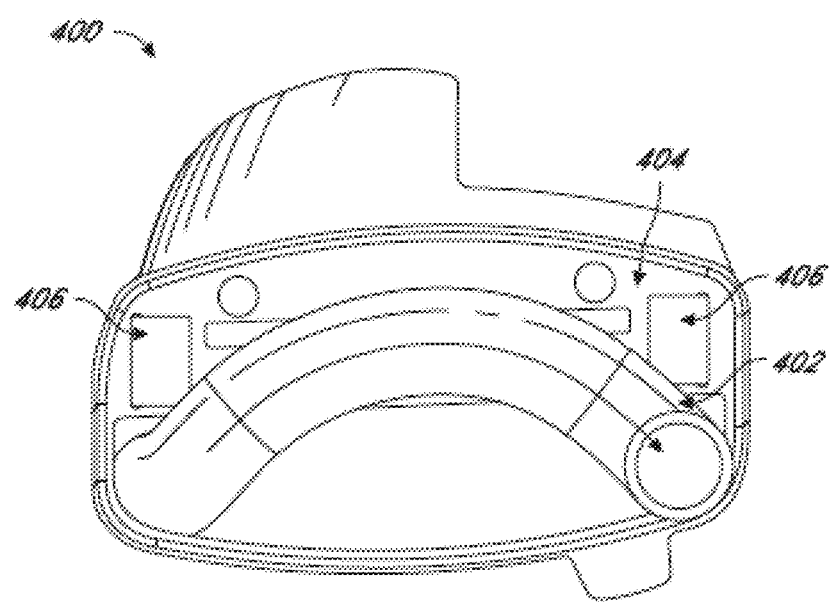
FIG. 21 illustrates a sensing chamber of an example motor and sensor module.

Turning to FIG. 21, the gases exiting the blower can enter a flow path 402 in a sensor chamber 400, which can be positioned within the motor and sensor module and can be the sensor chamber 2007 of FIG. 20. The flow path 402 can have a curved shape. The flow path 402 can be configured to have a curved shape with no sharp turns. The flow path 402 can have curved ends with a straighter section between the curved ends. A curved flow path shape can reduce pressure drop in a gases flow without reducing the sensitivity of flow measurements by partially coinciding a measuring region with the flow path to form a measurement portion of the flow path, which will be described below with reference to FIGS. 23A-23B.

A sensing circuit board 404 with sensors, such as acoustic transmitters and/or receivers, humidity sensor, temperature sensor, thermistor, and the like, can be positioned in the sensor chamber 400 such that the sensing circuit board 404 is at least partially immersed in the flow path 402. Immersing at least part of the sensing circuit board and sensors in the flow path can increase the accuracy of measurements because the sensors immersed in the flow are more likely to be subject to the same conditions, such as temperature and pressure, as the gases flow, and therefore provide a better representation of the characteristics of the gases flow. After passing through the flow path 402 in the sensor chamber 400, the gases can exit to the humidification chamber.

The gases flow rate may be measured using at least two different types of sensors. The first type of sensor can comprise a thermistor, which can determine a flow rate by monitoring heat transfer between the gases flow and the thermistor. The thermistor flow sensor can run the thermistor at a constant target temperature within the flow when the gases flow around and past the thermistor. The sensor can measure an amount of power required to maintain the thermistor at the target temperature. The target temperature can be configured to be higher than a temperature of the gases flow, such that more power is required to maintain the thermistor at the target temperature at a higher flow rate.

The thermistor flow rate sensor can also maintain a plurality of (for example, two, three, or more) constant temperatures on a thermistor to avoid the difference between the target temperature and the gases flow temperature from being too small or too large. The plurality of different target temperatures can allow the thermistor flow rate sensor to be accurate across a large temperature range of the gases. For example, the thermistor circuit can be configured to be able to switch between two different target temperatures, such that the temperature of the gases flow will always fall within a certain range relative to one of the two target temperatures (for example, not too close but not too far). The thermistor circuit can be configured to operate at a first target temperature of about 50° C. to about 70° C., or about 66° C. The first target temperature can be associated with a desirable flow temperature range of between about 0° C. to about 60° C., or about 0° C. and about 40° C. The thermistor circuit can be configured to operate at a second target temperature of about 90° C. to about 110° C., or about 100° C. The second target temperature can be associated with a desirable flow temperature range of between about 20° C. to about 100° C., or about 30° C. and about 70° C.

The controller can be configured to adjust the thermistor circuit to change between at least the first and second target temperature modes by connecting or bypassing a resistor within the thermistor circuit. The thermistor circuit can be arranged as a Wheatstone bridge configuration comprising a first voltage divider arm and a second voltage divider arm. The thermistor can be located on one of the voltage divider arms. More details of a thermistor flow rate sensor are described in PCT Application No. PCT/NZ2017/050119, filed Sep. 3, 2017, which is incorporated by reference herein in its entirety.

The second type of sensor can comprise an acoustic sensor assembly. Acoustic sensors including acoustic transmitters and/or receivers can be used to measure a time of flight of acoustic signals to determine gases velocity and/or composition, which can be used in flow therapy apparatuses.

In one ultrasonic sensing (including ultrasonic transmitters and/or receivers) topology, a driver causes a first sensor, such as an ultrasonic transducer, to produce an ultrasonic pulse in a first direction. A second sensor, such as a second ultrasonic transducer, receives this pulse and provides a measurement of the time of flight of the pulse between the first and second ultrasonic transducers. Using this time of flight measurement, the speed of sound of the gases flow between the ultrasonic transducers can be calculated by a processor or controller of the respiratory system. The second sensor can transmit and the first sensor can receive a pulse in a second direction opposite the first direction to provide a second measurement of the time of flight, allowing characteristics of the gases flow, such as a flow rate or velocity, to be determined. In another acoustic sensing topology, acoustic pulses transmitted by an acoustic transmitter, such as an ultrasonic transducer, can be received by acoustic receivers, such as microphones. More details of an acoustic flow rate sensor are described in PCT application PCT/NZ2016/050193, filed Dec. 2, 2016, which is incorporated by reference herein in its entirety.

Readings from both the first and second types of sensors can be combined to determine a more accurate flow measurement. For example, a previously determined flow rate and one or more outputs from one of the types of sensor can be used to determine a predicted current flow rate. The predicted current flow rate can then be updated using one or more outputs from the other one of the first and second types of sensor, in order to calculate a final flow rate.

Example Patient Detection Processes

As discussed above, when a patient is breathing through his or her nose into the patient interface of the respiratory system, a breathing signal is detected in the flow rate or other flow parameters due to the flow resistance variation caused by inhalation and exhalation. The patient can be detached from the breathing system such that there is no breathing signal in the gases flow parameter.

It can be advantageous for the respiratory system to be able to determine whether the patient is attached or detached, such as using the patient attachment determination to help the controller determine if a dominant frequency of a frequency analysis of the gases flow parameter is the respiratory rate. Detection of patient detachment can also have other applications, which will be described below in greater detail. In addition to determining whether the patient is attached or detached to the respiratory system, it can also be helpful to know whether the patient is previously attached and in the process of detaching from the respiratory device, or previously detached from the respiratory device and in the process of attaching to the respiratory device.

The processes disclosed herein assess a time domain feature of flow parameter data in order to determine whether the patient is attached or detached. Additionally, the processes can classify the patient attachment status into one of the four categories: detached, attaching, attached, or detaching.

The flow rate or other gases flow parameter signal can be fed through a pre-processing step. This step may allow the controller to decide whether the gases flow parameter is suitable for use in determining patient attachment, and/or to remove certain features from the flow parameters, such that the flow parameter signal that is fed into the patient attachment detection process can be more representative of any effects the patient's respiration is having on the gases flow parameter (such as the flow rate, pressure, or otherwise). Details of the pre-processing step are described below in greater detail with reference to FIGS. 23A-23D.

Determining Instantaneous and Filtered Feature

Figure 22:
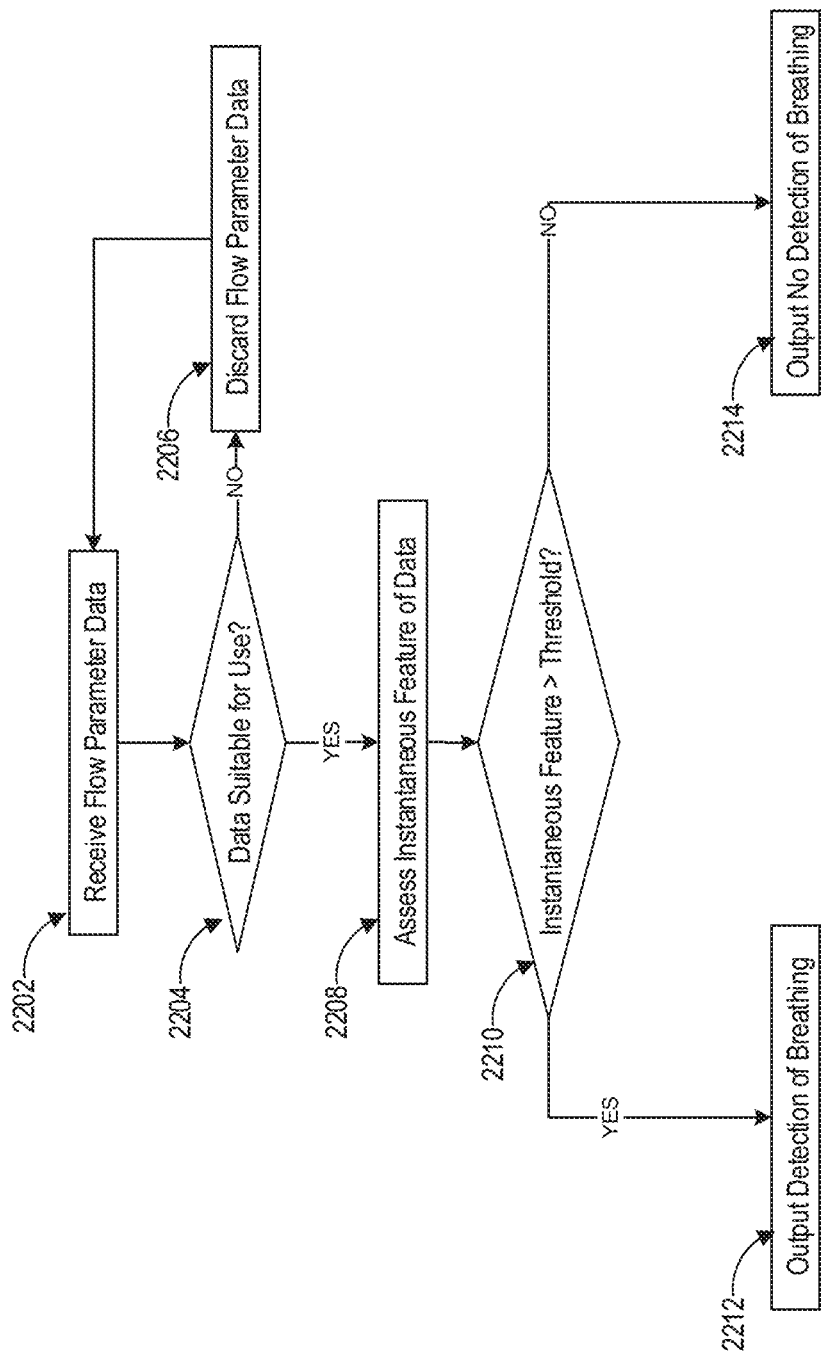
FIG. 22 illustrates an example flow chart of assessing instantaneous features for patient breathing detection.

As described above, it is assumed that fluctuations in pre-processed flow rate or other flow parameter data are made up of random uncorrelated noise and a correlated breathing signal generated by the patient, if the patient is attached to the respiratory system and breathing through the patient interface. As shown in FIG. 22, the process can start with the controller receiving the flow parameter data (such as unprocessed data) at step 2202. At decision step 2204, the controller can perform the pre-processing step, for example, by determining if the flow parameter data is good or suitable for use. If the data is not suitable for use, the controller can discard the data at step 2206 and return to step 2202.

Figures 23A, 23B, 23C:
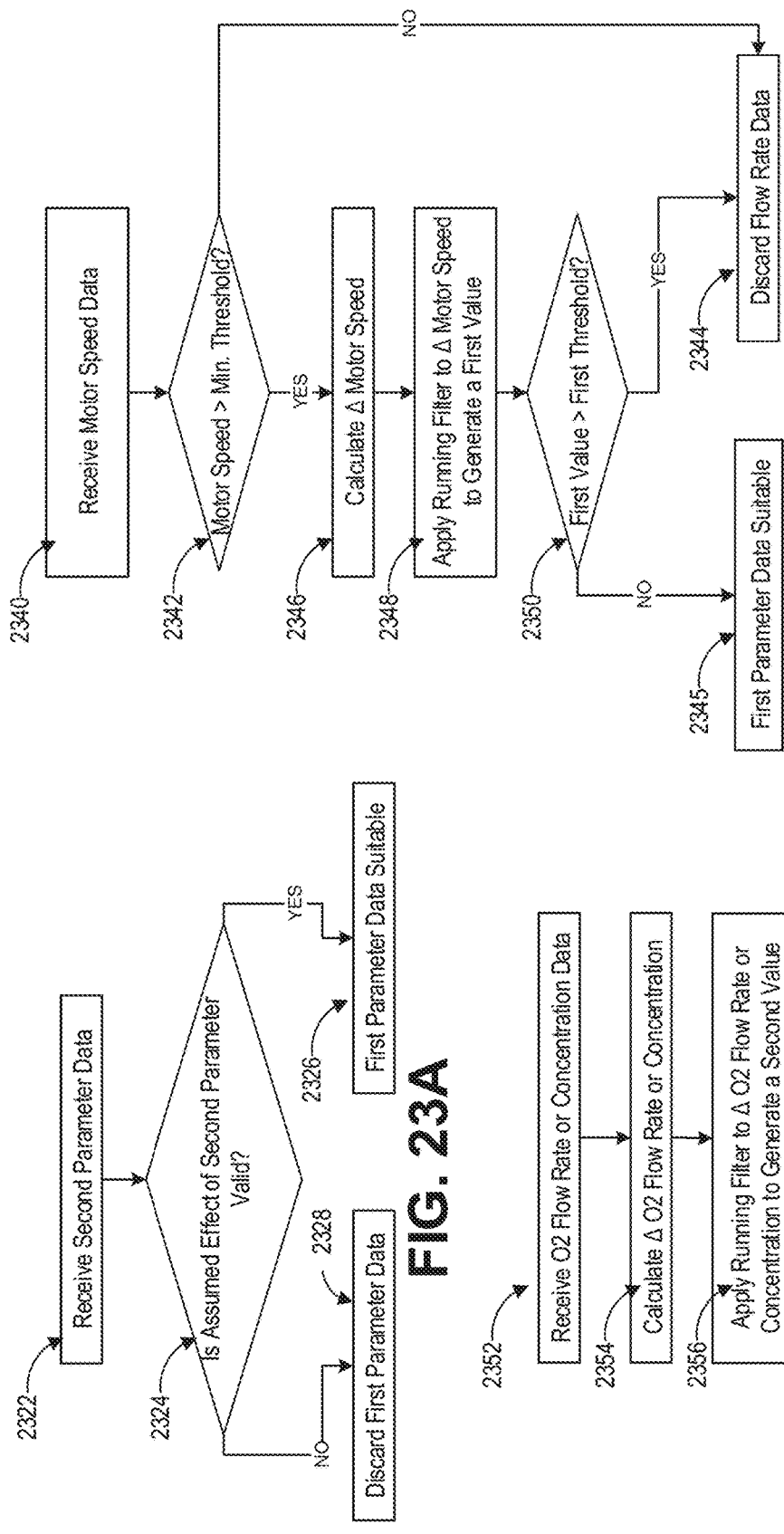
FIGS. 23A-23C illustrate examples of determining whether flow parameter data is suitable for use in determining patient attachment and/or breathing.

FIGS. 23A-23C illustrate example processes for determining the suitability of the data. The flow parameter can be flow rate. The flow parameter can also be pressure or other types of parameters disclosed herein. The flow parameter data can be the absolute value of the gases flow parameter. Alternatively, the flow parameter data can be a variation of the gases flow parameter. The variation can be determined by subtracting a target value of the gases flow parameter from the measured value of the gases flow parameter. The variation can also be determined by subtracting the estimated effect of a second gases flow parameter from the measured value of the first gases flow parameter. The variation can be calculated after determining that the flow parameter data is suitable for use. In a configuration, the variation can also be calculated before determining the flow parameter data is suitable for use.

As shown in FIG. 23A, at step 2322, the controller can receive the second flow parameter data that is of a different type than a first flow parameter data, such as the flow parameter data received at step 2202 of FIG. 22. The second parameter is assumed to have effects on the first parameter. For example, the motor speed, pressure, and/or oxygen flow rate or concentration can have an effect on the gases flow rate that is separate from the effect of the patient's respiration on the gases flow rate. At decision step 2324, the controller can determine whether the assumed effect is valid. For example, the assumed effect can be valid if the assumed effect is greater than a minimum threshold. If the assumed effect is not valid, such as by being lower than the minimum threshold, it can be difficult to predict accurately the effect of the second parameter on the first parameter. Accordingly, at step 2328, the controller can determine that first parameter data, which can be the flow parameter data received at step 2202 of FIG. 22, is not suitable for use and may discard the first parameter data. If the assumed effect is valid, such as by being greater than the minimum threshold, at step 2326 the controller can determine that the first parameter data is suitable for use.

In the process of FIGS. 23B and 23C, the first parameter can include the flow rate data and the second parameter(s) can include the motor speed, the oxygen flow rate, and/or the oxygen concentration. In some configurations, the processes of FIGS. 23B and 23C can both be performed to determine whether the flow parameter data is suitable for use. At step 2340 of FIG. 23B, the controller can receive the motor speed data. In order to identify the patient's respiration in the flow rate data, the motor needs to be operating at a sufficient speed. If the motor speed is too low, the effect of the motor speed on the flow data (such as the flow rate) may not be accurately predicted. Therefore, at step 2342, the controller can compare the motor speed to a minimum motor speed threshold. If the motor speed is below the threshold, at step 2344, the controller can deem the flow parameter data as unsuitable, and can discard a portion or all of the flow parameter data. If the motor speed is above the threshold, at step 2346, the controller can calculate the recent changes in the motor speed. A change in motor speed can result in a change in the flow parameter, which makes it more difficult to identify the patient's respiration in the flow parameter data. While the effect of the motor speed can be removed from the flow parameter data to some degree, larger changes in motor speed may make the data too unreliable for identifying the patient's respiration. Therefore, at step 2348, the controller can apply a running filter to the relative changes in motor speed in order to generate a first value representing the recent relative changes in motor speed. At decision step 2350, the controller can compare the first value with a first threshold. If the first value is above the first threshold, the controller can deem the flow parameter data to be unsuitable, and the flow data point can be discarded at step 2344. If the first value is below the first threshold, the controller can deem the flow parameter data to be suitable at step 2345.

The flow parameter (such as the flow rate) can also be affected by the flow rate or concentration of a supplementary gas from a supplementary gas source, such oxygen from a supplementary oxygen source. Although FIG. 23C is illustrated using oxygen as an example, the steps performed relating the flow rate or concentration of oxygen can also be performed on the flow rate or concentration of any other supplementary gas mixed with ambient air. At step 2352, the controller can receive an oxygen flow rate data or an oxygen concentration data. At step 2354, the controller can calculate the recent changes in the oxygen flow rate or the oxygen concentration. If the flow rate or concentration of oxygen changes, the resulting change in the total flow rate can make it more difficult to identify the patient's respiration in the flow rate signal or other flow parameter signal. Therefore, at step 2356, the controller can apply a running filter to the changes in oxygen concentration of the gases or the oxygen flow rate in order to generate a second value representing the recent changes in oxygen concentration or flow rate. At decision step 2358, the controller can compare the second value with a second threshold. If the second value is above the second threshold, the controller can determine the flow parameter data is unsuitable, and the flow parameter data point can be discarded at step 2344. If the second value is below the threshold, at step 2360, the controller can deem the flow parameter data to be suitable.

For the above determination, either oxygen (or other supplementary gas) concentration data or oxygen (or other supplementary gas) flow rate data can be used. Oxygen concentration data can be determined using one or more sensors in the respiratory device, such as ultrasonic sensors. Oxygen flow rate from the oxygen source can be determined by an oxygen flow rate sensor located downstream of the oxygen source.

As described above, if the controller deems the data to be suitable, the flow date (or any other flow parameter data) can also be modified to remove the effect of the motor (or other factors, such as the oxygen concentration or flow rate). Modifying the gases flow parameter can involve removing the assumed effect of other variables from the gases flow parameter (such as the motor speed). This assumed effect is only valid if the gases flow parameter data meets certain criteria. As described above, if these criteria are not met, the data may be discarded.

Figure 23D:
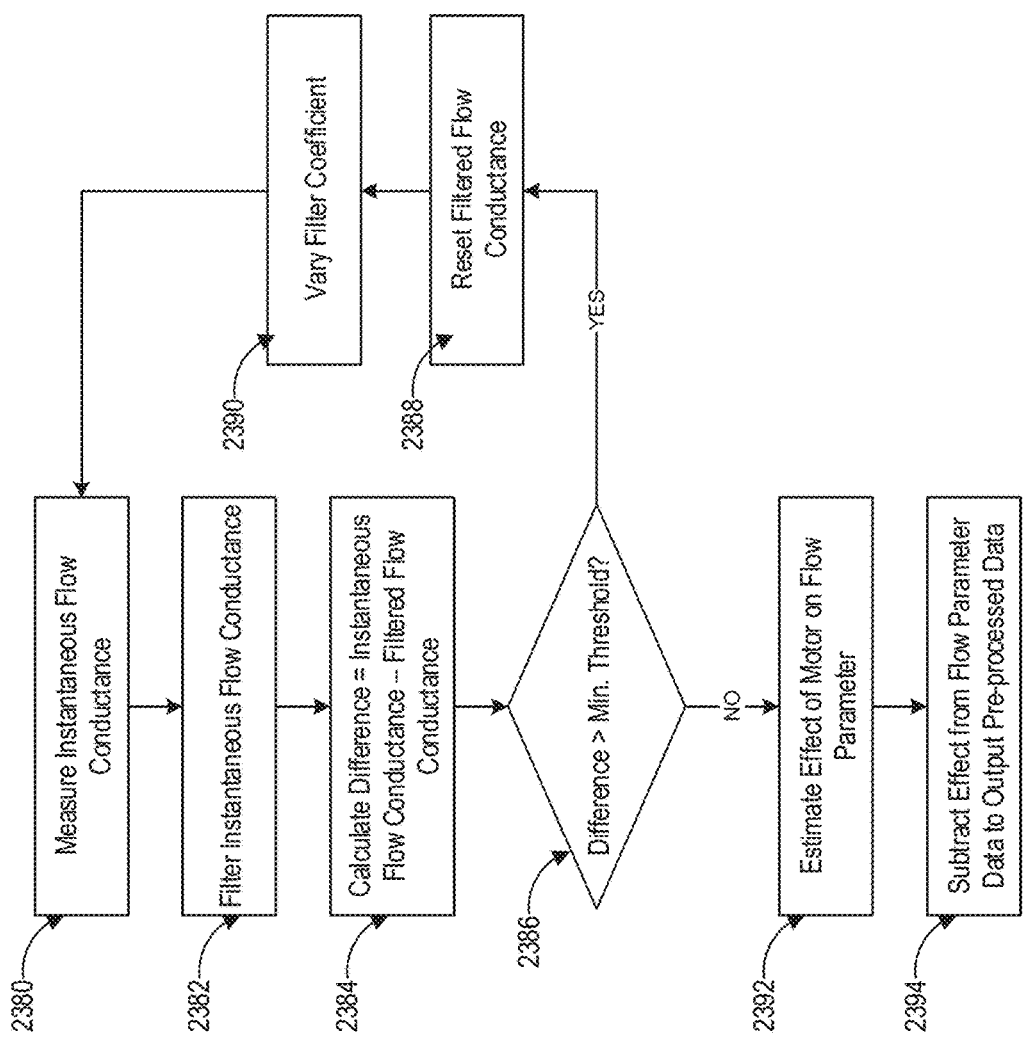
FIG. 23D illustrates an example flow chart of modifying flow rate data to remove assumed effects of motor speed.

FIG. 23D illustrates an example process of modifying the flow rate data to remove the effect of motor speed. The effect of the motor can be estimated using the motor speed and the flow conductance. At step 2380, the controller can measure an instantaneous flow conductance. The flow conductance is approximately constant with time, and can therefore be estimated using a low pass filter. The controller measures the instantaneous flow conductance at each iteration using the current motor speed and the measured flow rate. At step 2382, the controller filters the instantaneous flow conductance in order to determine the filtered flow conductance.

At decision step 2384, the controller can compare the instantaneous flow conductance with the filtered flow conductance to see if the difference is significantly different. If the difference is significant, it is likely that something has changed the physical system, such as the cannula being attached or detached. The instantaneous flow conductance can be compared with the filtered flow conductance by taking the difference of the two variables and comparing it with a minimum threshold at decision step 2386. If the difference exceeds the threshold, the difference is considered to be significant, and the controller can reset the filtered flow conductance at step 2388. The reset can allow the device to quickly adjust its estimate of the flow conductance when the cannula has been attached and detached from the patient.

At step 2390, the controller can also vary the filter coefficient of the filtered flow conductance calculation based on the difference between the instantaneous flow conductance and the filtered flow conductance. This allows the filtered flow conductance to change more quickly when the variance of the flow conductance is high, such as when the cannula has first been attached. The controller can then return to step 2380 to start a new iteration of the process.

If the difference does not exceed the threshold, the difference is considered to be not significant, and the controller can estimate the effect of the motor on the flow rate at step 2392. The controller can output a value of the effect using the filtered flow conductance and the motor speed. At step 2394, the value can be subtracted or otherwise removed from the flow rate data to arrive at the pre-processed flow rate data. The pre-processed flow rate data can be more indicative of the patient's respiratory flow (although the pre-processed flow rate data can still include signal noise).

The controller can also track the recent changes in the flow conductance. The changes can be tracked by adding the difference between the last two instantaneous flow conductance values to a running total, which is then decayed over time. The decayed running total is filtered to obtain the filtered recent changes in flow conductivity. The filtered recent changes in flow conductivity can be used in further parts of the frequency analysis algorithm along with the pre-processed flow rate data.

Returning to FIG. 22, if the flow parameter data is suitable for use, at step 2208, the controller can assess an instantaneous feature of the recent data, which can be done by analyzing whether there is a trend in the recent data. The time scale of the recent data can be fixed, for example, to less than a minimum expected or typical respiratory period, preferably between a minimum expected or typical respiratory period and a quarter of a minimum expected or typical respiratory period, or between a half of a minimum expected or typical respiratory period and a quarter of a minimum expected or typical respiratory period, or preferably less than a half of a minimum expected or typical respiratory period, or more preferably less than a quarter of a minimum expected or typical respiratory period. The assessing can be done by using two vectors, with the instantaneous feature being a measure of how well the recent data points correlate to one or a combination of the two vectors. The assessing can also be done by using a single vector or more than two vectors.

If no patient is breathing through the patient interface, the random fluctuations in the pre-processed flow data may have lower correlation with one or both of the two vectors than when the patient is breathing through the patient interface. Additionally, data of higher frequencies can have lower correlation than data of lower frequencies, as the time period for the data that is assessed would have multiple oscillations of said higher frequencies. The signals that can result in a high correlation (and therefore a large instantaneous feature) are signals with a low frequency, such as the patient's breathing signal.

Figure 24:
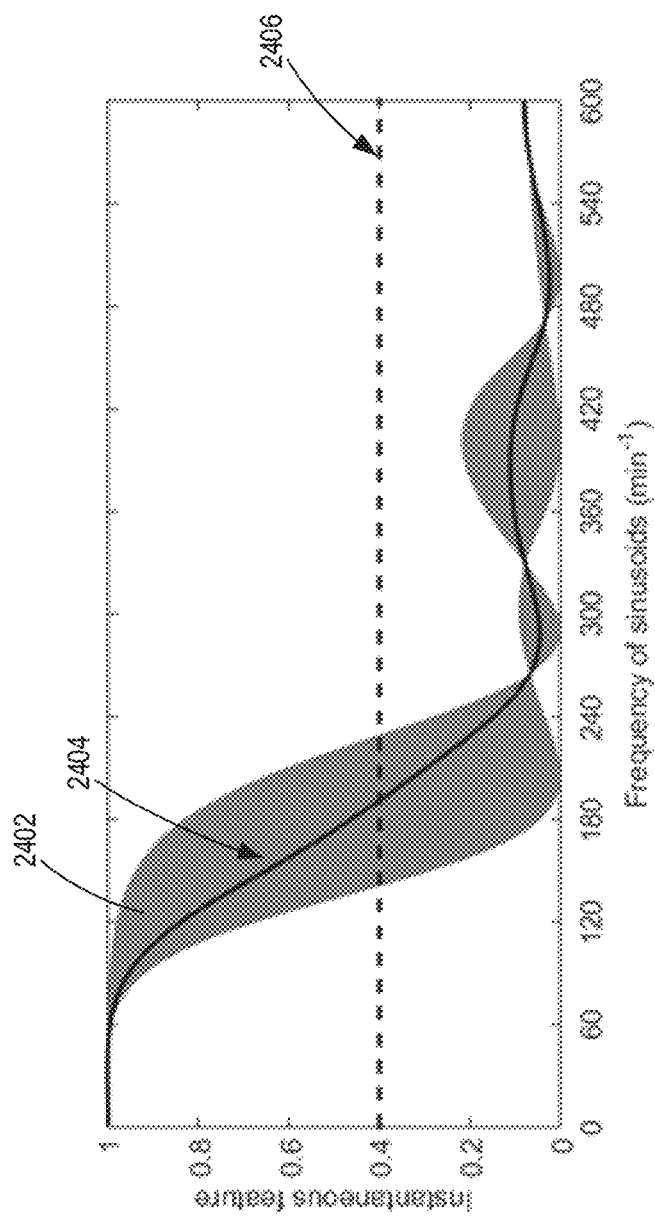
FIG. 24 illustrates an example instantaneous feature when various frequencies are assessed (with no signal noise).

FIG. 24 shows an example of the instantaneous feature when various frequencies of the data (which can include sinusoids) are assessed (with no signal noise). The shaded area 2402 represents possible values of the instantaneous feature (due to the different phases of the sinusoid). The solid line 2404 presents the average of the instantaneous feature for that frequency. With continued reference to FIG. 22, at decision step 2210, the controller determines whether the instantaneous feature is above a certain instantaneous feature threshold. In a configuration, such as shown in FIG. 24, the threshold is illustrated as a dotted line 2406.

In a configuration, sinusoids with a frequency of less than 60 $min^{-1}$ can have an instantaneous feature that is close to 1. This frequency can correlate most with the typical breathing frequencies of a patient, such as an adult patient. A breathing signal can be decomposed into the fundamental (breathing) frequency and the harmonics. The harmonics typically get smaller with the harmonic order (for example, the first harmonic has a smaller frequency amplitude than the fundamental and the second harmonic has a smaller frequency amplitude than the first harmonic). All of these harmonics contribute to the instantaneous feature with the highest amplitude, that is, the fundamental frequency amplitude, having the most effect. In some configurations, the threshold can be lower than 1 (such as about 0.4 in FIG. 24) so that frequencies between 60 and 120 $min^{-1}$ can also exceed that threshold. These frequencies may still be caused by the patient's breathing, particularly in the case of infants. Higher frequencies described above do not typically generate an instantaneous feature above the threshold.

Returning to FIG. 22, if the instantaneous feature is above the threshold, at step 2212, the controller can output that breathing is detected or that the patient is attached. If the instantaneous feature is not above the threshold, at step 2214, the controller can output that no breathing is detected or that the patient is detached.

The instantaneous feature being above the instantaneous feature threshold can be indicative of a breathing patient being attached to the patient interface (such as by being attached to a cannula). In addition, to reduce signal noise resulting in fluctuations in the instantaneous feature, the instantaneous feature can also be filtered before using those features for determining a patient attachment status of the respiratory system.

Figure 25A:
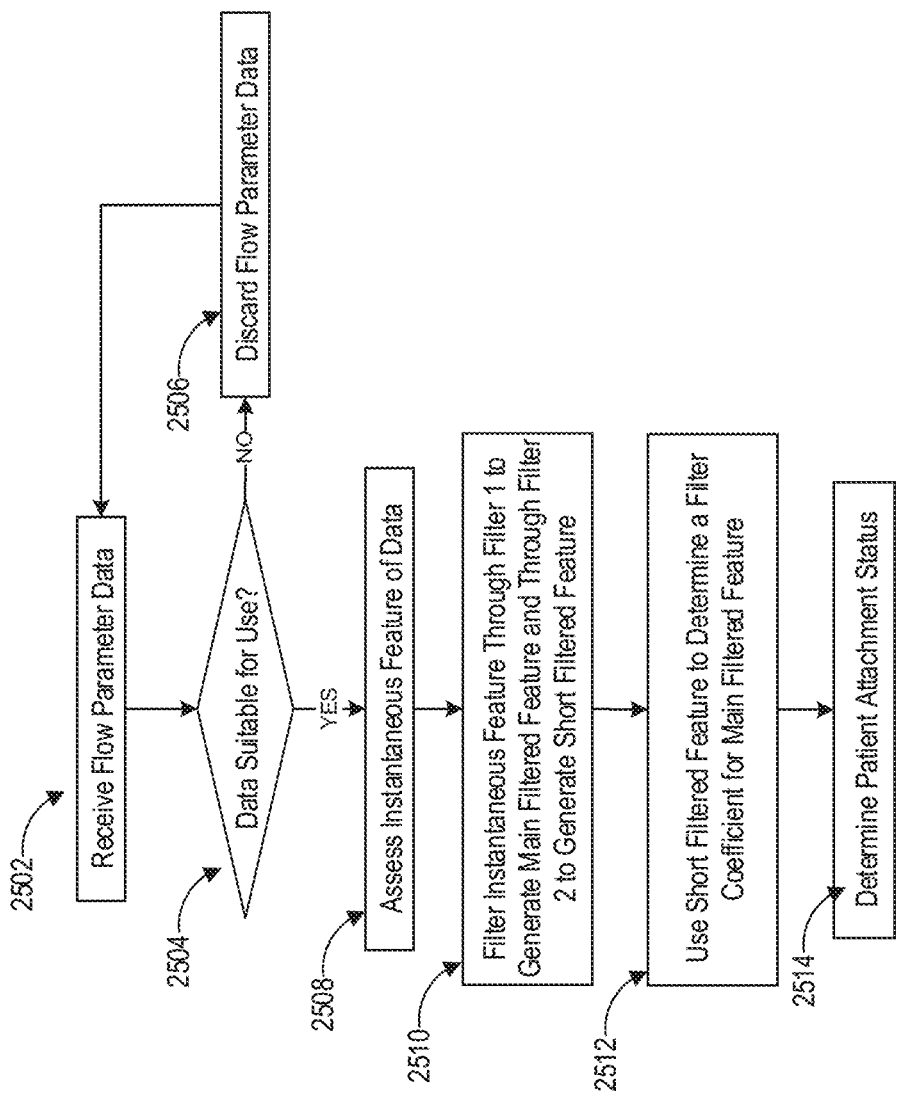
FIG. 25A illustrates an example flow chart of determining filtered features for patient attachment determination.

As shown in FIG. 25A, two filters can be applied to the instantaneous features in a process to obtain filtered features. The process can start with the controller receiving the flow parameter data (such as unprocessed data) at step 2502. At decision step 2504, the controller can perform the pre-processing step, such as by determining if the flow parameter data is good or suitable for use. If the data is not suitable for use, the controller can discard the data at step 2506 and return to step 2502. If the data is suitable for use, at step 2508, the controller can assess an instantaneous feature of the data.

Figure 25B:
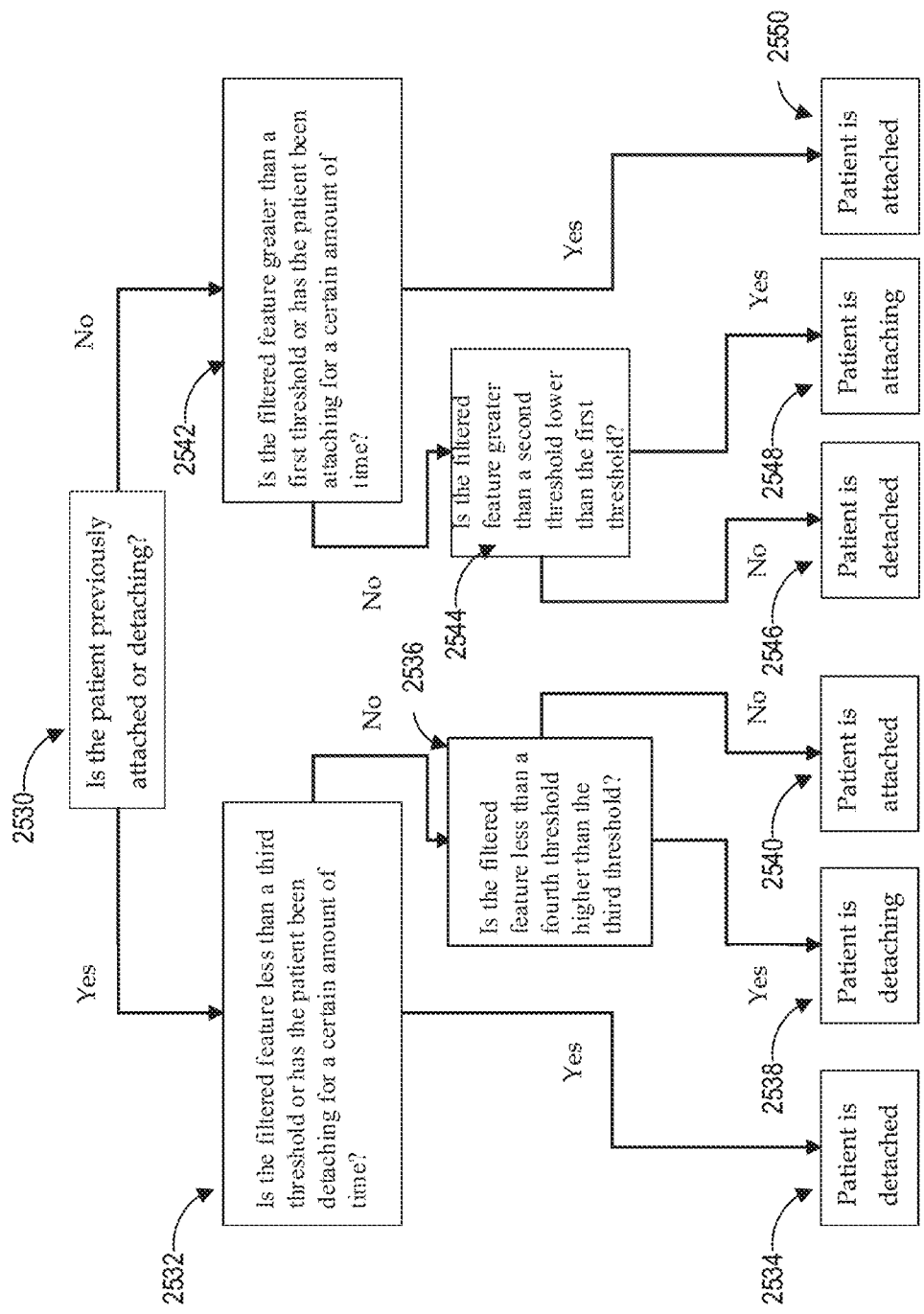
FIG. 25B illustrates an example flow chart for determining patient attachment statuses using the filtered features.

At step 2510, the controller can apply two different filters on the instantaneous feature to generate a main filtered feature and a short filtered feature respectively. At step 2512, the controller can use the short filtered feature to determine the filter coefficient for the main filtered feature. At step 2514, the filtered features can be used to determine a patient attachment status, such as shown in FIG. 25B. The application of two filters allow the main filtered feature to change more quickly when the instantaneous feature is closer to 1, thereby allowing a patient attachment determination to be made more quickly when there is a strong breathing signal. In addition, when a patient is not breathing on the patient interface (such as the cannula), the instantaneous feature will drop closer to 0, thereby increasing the filter coefficient for the main filtered feature and making the main filtered feature change less quickly, which in turn allows the patient attachment determination to be made less quickly. The controller can take a comparatively longer time (than when the patient is attached and breathing via the patient interface) to determine that a patient is detached, but can take a comparatively shorter time to determine that a patient is attached.

It is more preferable to err on the side of determining that a patient is attached when a patient is not attached to the respiratory system than to err on the side of determining that a patient is detached when a patient is still attached to the system. This is in part because a number of algorithms for controlling the flow rate and/or motor speed of the respiratory device rely on a patient being attached in order to function. Incorrectly determining that a patient is detached may prevent these algorithms from functioning when needed. This may prevent the device from synchronizing the delivery of gases with the patient's breathing and/or reduce the effect of the respiratory therapy. Further, incorrectly determining that a patient is detached may result in discomfort due to incorrect flow rate and/or motor speed to the patient who is still attached to the patient interface.

Figure 26:
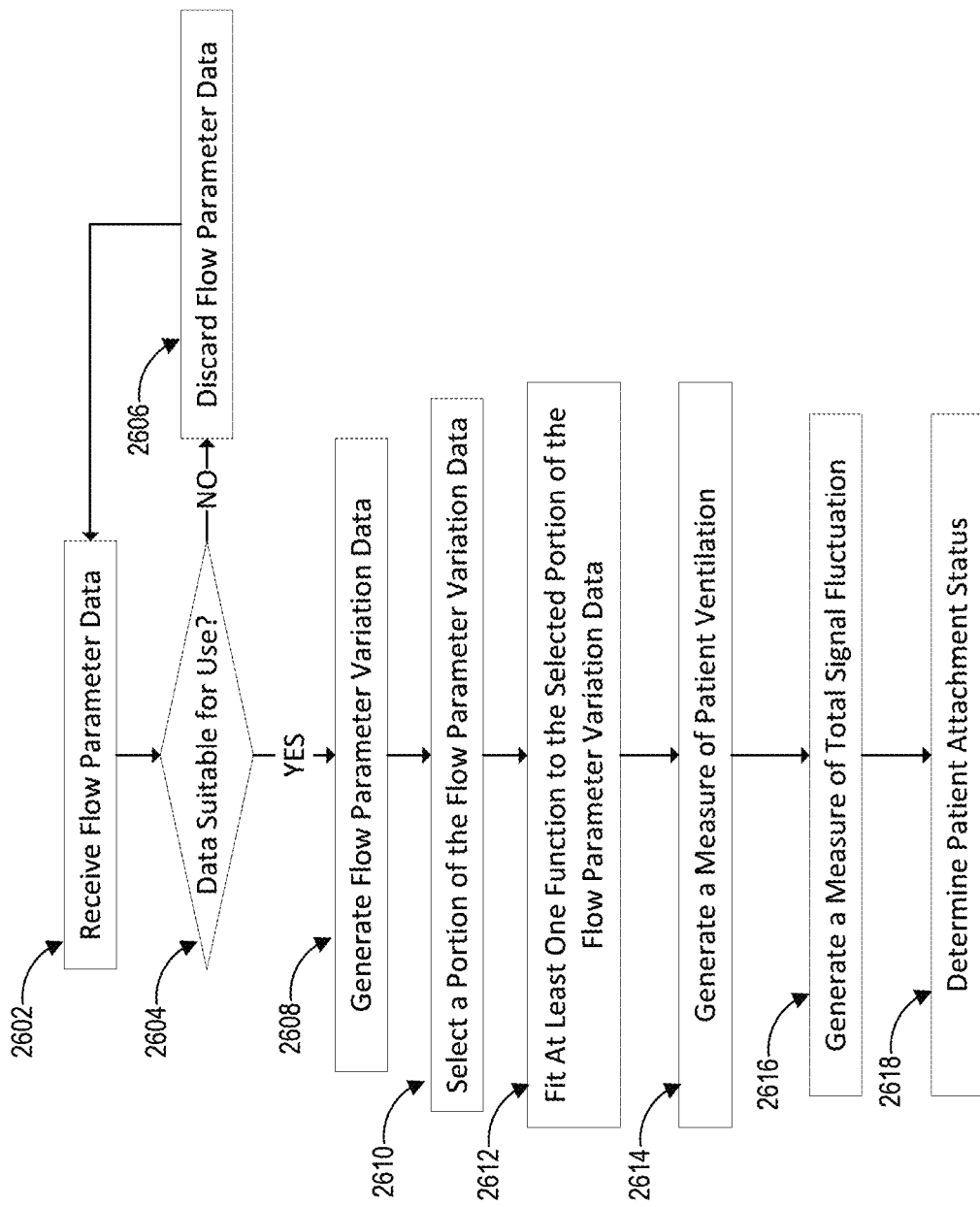
FIG. 26 illustrates an example flow chart for generating measures to determine patient attachment to a respiratory system.

As shown in FIG. 26, a process can be applied to flow parameter data to obtain a measure of patient ventilation and a measure of total signal fluctuation. Similar to other processes described herein, the process can start with the controller receiving the data of a flow parameter (which can include unprocessed data of a first parameter or second parameter) at step 2602. The flow parameter can be flow rate or a parameter indicative of flow rate. In a configuration, the flow rate can refer to a total flow rate, including respiratory flow rate, supplemental gases flow rate, or others. In a configuration, the flow parameter can be a direct measure of gases flow. The flow parameter can be pressure, motor speed, or other types of parameters disclosed herein. The flow parameter can be a measure of or parameter indicative of pressure, motor speed, or other types of parameters disclosed herein. The flow parameter can be representative of performance of a component of the device. At decision step 2604, the controller can perform the pre-processing step, such as by determining if the flow parameter data is good or suitable for use. If the data is not suitable for use, the controller can discard the data at step 2606 and return to step 2602.

If the data is suitable for use, at step 2608, the controller can generate flow parameter variation data. The flow parameter variation data can be determined by subtracting a target value of the flow parameter data from the measured value of the flow parameter data. The flow parameter variation data can be determined by subtracting an estimated effect of a second parameter from a measured value of a first parameter. In a configuration, the first flow parameter or first parameter is a gases flow rate or a parameter indicative of a gases flow rate. In a configuration, the second flow parameter or second parameter is a measure of, or a parameter indicative of pressure, motor speed, or another flow. The estimated effect of the second parameter on the first parameter can be a change in flow rate that can be expected based on the current value of the second parameter, such as the current motor speed. This estimated effect can assume no noise or patient interaction. The estimated effect can be calculated using the current value of the second parameter, such as the current motor speed, as well as a running average of a relationship between the motor speed and flow rate, which can be used to characterize the relationship between the first flow parameter and the second flow parameter. In a configuration, the flow parameter variation data can be determined by subtracting a first average value of the flow parameter data from a second average value of the flow parameter data. The first average value can be later in time than the second average value. The first average value can also be based on a longer window of data than the second average value. In a configuration, the second average value can be based on a longer window of data than the first average value. The windows of data can be mutually exclusive in time or overlapping in time. The windows of data can relate to the same length of time or different lengths of time. The first average value of the flow parameter data can be determined by applying a filter or ongoing filter to the flow parameter data. The first average value of the flow parameter data can be constantly or continuously updated. The second average value can be based on measured values. The flow parameter variation data can be calculated after determining that the flow parameter data is suitable for use. In a configuration, the flow parameter variation data can be calculated before determining the flow parameter data is suitable for use.

At step 2610, the controller selects a portion of the flow parameter variation data to analyze. The portion of the flow parameter variation data selected can be the last measured flow parameter variation data, or flow parameter variation data measured contemporaneously or close in time with the analysis. The portion of the flow parameter variation data can relate to a time period within a predefined time period. The portion can be selected to obtain a data set representing or relating to a specific length of time. Selecting a portion of the processed flow parameter data relating to a longer period of time can result in more noise reliably being filtered out of the processed flow parameter data compared to selecting a portion of the processed flow parameter data relating to a shorter period of time. However, selecting a portion of the processed flow parameter data relating to a longer period of time can result in filtering out breathing signals with higher frequencies compared to selecting a portion of the processed flow parameter data relating to a shorter period of time. Accordingly, there can be a tradeoff between filtering noise and detecting or capturing instantaneous changes when selecting a portion of the processed flow parameter data representing a length of time. In a configuration, it can be advantageous to select a portion of the processed flow parameter data representing a length of time that is less than a breathing period. In a configuration, selecting a portion of the processed flow parameter data representing in the range of 0.5-2 seconds can provide reliability in detecting patient interaction or attachment for the majority of expected breathing frequencies (as well as talking, coughing, etc.), while being a length that makes it less likely to generate a false determination of patient attachment or interaction due to random noise. In a configuration, the selected portion of the processed flow parameter data can be less than 0.5, 0.5-1, 1-1.5, 1.5-2, 2-2.5, 2.5-3, 3-3.5, 3.5-4, 4-4.5, 4.5-5, 5-5.5, 5.5-6, or more than 6 seconds.

In a configuration, the controller selects a portion of the processed flow parameter data before generating the flow parameter variation data at step 2608. In a configuration, the controller selects a portion (or window) of the processed flow parameter data relating to a specific length of time such that the signal noise is filtered out of the measure of instantaneous patient ventilation, described hereafter. In a configuration, the controller selects a portion of the processed flow parameter data relating to a specific length of time such that expected breathing frequencies, which can include all expected breathing frequencies, result in an increased measure of instantaneous patient ventilation.

At step 2612, the controller fits one or more functions to the selected portion of the flow parameter variation data. The one or more functions can be algebraic, such as polynomial (for example, constant, linear, non-linear, quadratic, cubic, etc.), rational, root, and/or others. The one or more functions can be transcendental, such as exponential, hyperbolic, logarithmic, power, periodic (for example, trigonometric, etc.), and/or others. The controller can perform a variety of line and/or curve fitting techniques to fit the one or more functions to the selected portion of the flow parameter variation data, which can include the non-limiting example techniques of regression analysis, interpolation, extrapolation, linear least squares, non-linear least squares, total least squares, simple linear regressions, robust simple linear regression, polynomial regression, orthogonal regression, Deming regression, linear segmented regression, regression dilution, and/or others. The one or more functions, which includes at least those above, can generate a curve. The curve can be a line. The lines or curves described herein can include a plurality of curves, vertices, and/or other features. The lines described herein can be straight, angled, and/or horizontal. The lines described herein can be a line of best fit.

In a configuration, the controller can perform a least squares fit of a line, which can include fitting a linear function such as a straight line, to the selected portion of flow parameter variation data. For example, a straight line can be represented by $\hat{u}_{fin}=m+s*t$ where m is the mean value of the line, s is the slope, and t is a linearly increasing normalized time parameter. In a configuration, t can be a linearly increasing normalized time parameter that is equal to minus one at the oldest data point used and equal to one at the most recent data points used. In a configuration, the controller can fit a horizontal line to the selected portion of flow parameter variation data. The horizontal line can be the average of the flow parameter variation data representing or relating to the selected portion. For example, the horizontal line can be represented by $\hat{u}_{fin}=m$ where m is the mean value.

At step 2614, the controller generates a measure of patient ventilation. The measure of patient ventilation can mainly relate to patient ventilation but may include some noise. The controller can generate a measure of instantaneous patient ventilation, also referred to as a flow volume parameter or volume measurement, by determining an area under the function fit to the selected portion of the flow parameter variation data at step 2612. In a configuration, the controller can generate a measure of instantaneous patient ventilation by determining the area under a curve generated by the function fit to the flow parameter variation data at step 2612. In a configuration, the controller can generate a measure of instantaneous patient ventilation by determining the area under the absolute value of the one or more functions or curve generated by the one or more functions at step 2612. This can be determined by taking the integral of the absolute value of the one or more functions or curve generated by the one or more functions at step 2612. In one non-limiting example, this is represented in the equation illustrated below.

$$V_O = \int |\hat{u}_{fin}| dt$$

The measure of instantaneous patient ventilation ($V_o$) can be multiplied by one minute to be representative of minute patient ventilation. The measure of instantaneous patient ventilation can be filtered over time to generate the measure of patient ventilation which can be used to determine patient attachment. The measure of patient ventilation can be a measure of volume. The measure of patient ventilation can be represented by $\hat{V}_O$. A filter coefficient can be set such that data relating to approximately one minute is used. A longer filter coefficient can be used to make the determination of patient attachment more reliable but that configuration may be slower to react to the attachments and detachments of a patient.

At step 2616, the controller generates a measure of total signal fluctuation. The measure of total signal fluctuation can include noise resulting from electronics of the respiratory system, signal noise, the environment, patient respiration, patient ventilation, patient movement, and/or other noise originating from or not originating from the patient. The controller can generate a measure of instantaneous total signal fluctuation from the flow parameter variation data generated at step 2608. The controller can generate the measure of instantaneous total signal fluctuation, which can also be described as fluctuations or average fluctuations, by taking the absolute value of the flow parameter variation data. In one non-limiting example, this is represented in the equation below.

$$V_{short} = |\hat{u}|$$

In a configuration, each data point for the offset can instead be made positive by taking the square of the flow parameter variation data. Taking the square of the flow parameter variation data, however, can result in erroneous patient attachment determinations due to random outliers in the flow parameter variation data. Utilizing the absolute value can be more tolerant to outlier values in the flow parameter variation data which can result from coughing, yawning, etc. The measure of instantaneous total signal fluctuation ($V_{short}$) can be multiplied by one minute, similar to $V_o$. The measure of instantaneous total signal fluctuation can be considered to be representative of the total fluctuations in the flow parameter variation data resulting from both the patient signal and random noise.

Figure 27:
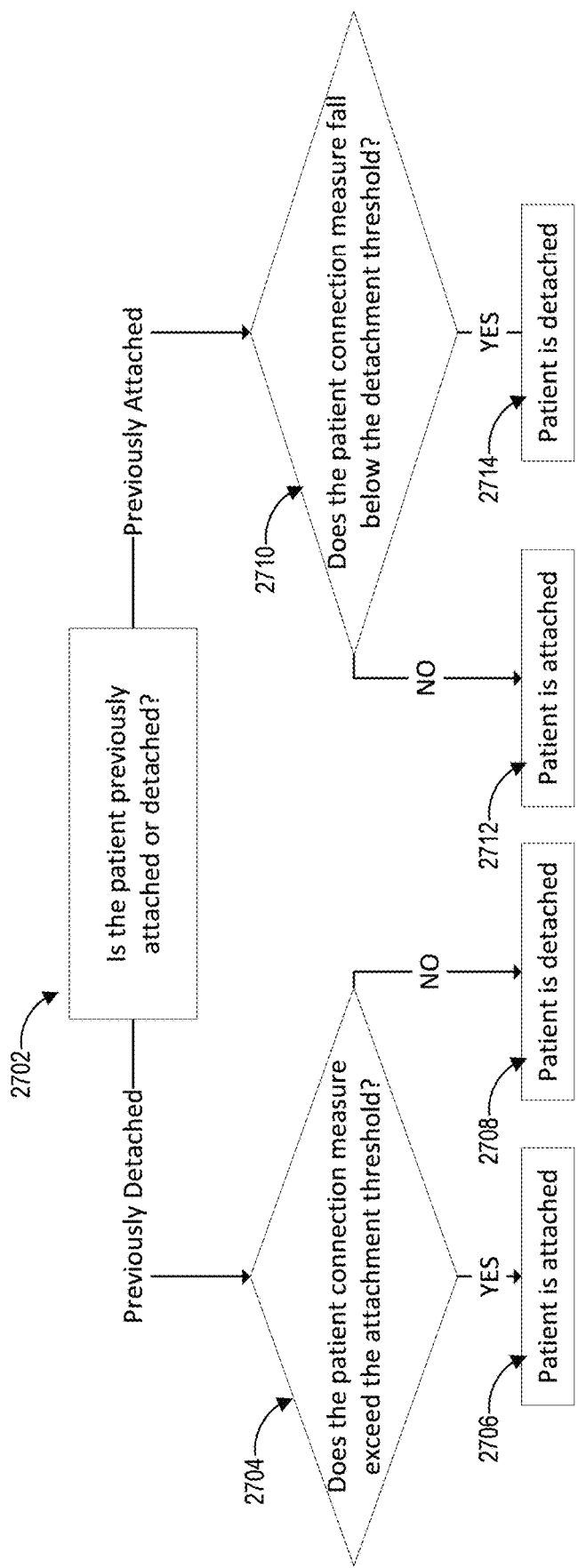
FIG. 27 illustrates an example flow chart for determining patient attachment using a patient connection measure.
Figure 28:
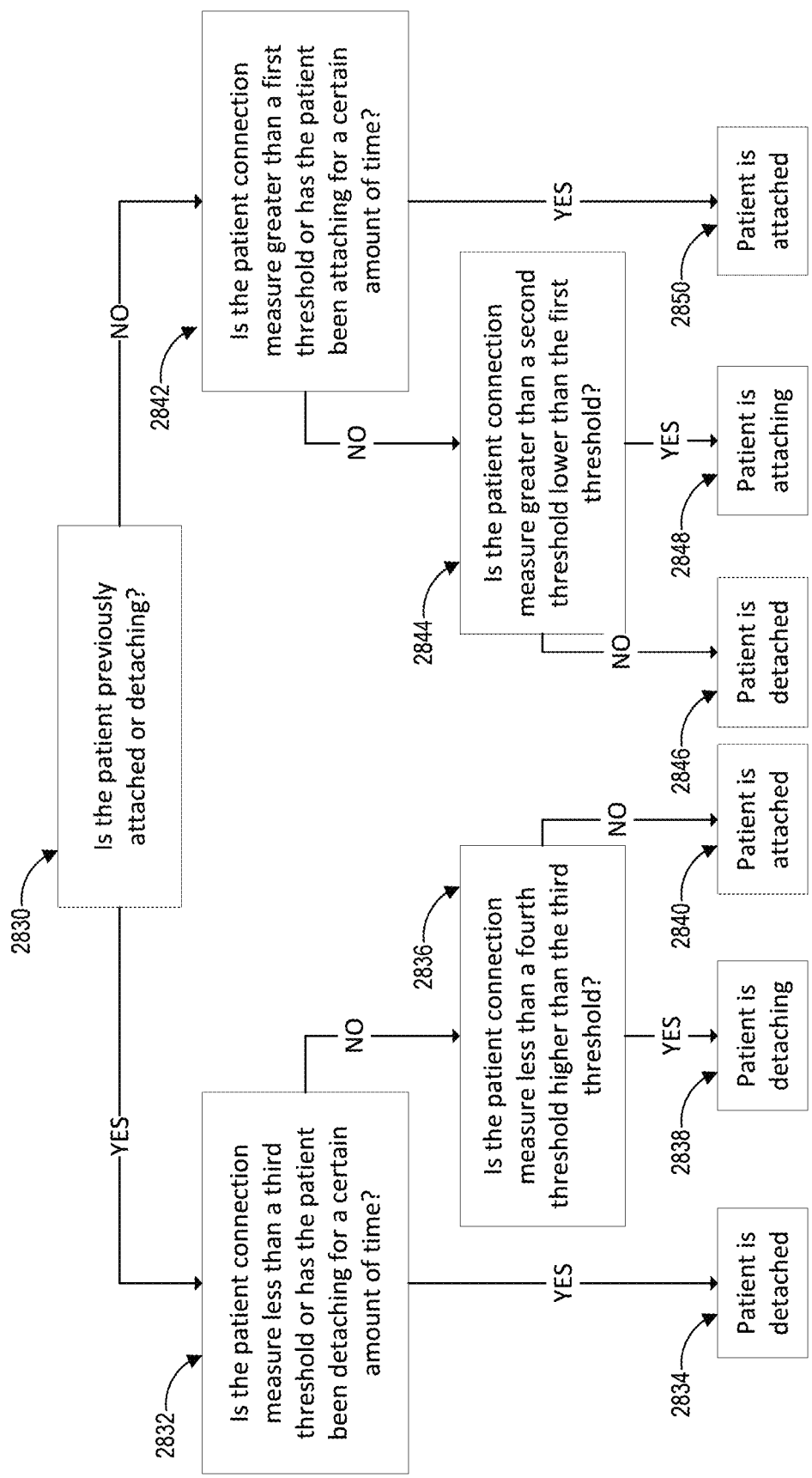
FIG. 28 illustrates another example flow chart for determining patient attachment status using a patient connection measure.

Similar to $V_o$, the measure of instantaneous total signal fluctuation ($V_{short}$) can be filtered over time to generate a measure of total signal fluctuation to facilitate determining patient attachment. The measure of total signal fluctuation can be represented by $\hat{V}_{short}$. A filter coefficient can be set such that data relating to approximately one minute is used. A longer filter coefficient could be used to make the determination of patient attachment more reliable but that configuration could be slower to react to the attachments and detachments of a patient. In a configuration, the measure of patient ventilation ($\hat{V}_O$) can be greater than or equal to the measure of total signal fluctuation ($\hat{V}_{short}$), which can be greater than or equal to 0. Because the measure of patient ventilation ($\hat{V}_O$) can be mainly related to a patient's minute ventilation and the measure of total signal fluctuation ($\hat{V}_{short}$) can be related to both a patient's minute ventilation and random noise, the controller can determine patient attachment, at step 2618, by comparing the two values as shown in FIGS. 27 and 28.

Determining Attachment Status

As shown in FIG. 25B, the controller can determine four categories of the patient attachment status, that is, whether the patient is detached, attaching, attached, or detaching from the respiratory system, using the filtered features described above. This assessment can be made by comparing the main filtered feature with one or more feature thresholds (such as a threshold close to 1 or slightly below 1 as described above). In order to arrive at a determination that the patient is attached or detached, the main filtered feature must be above or below a threshold. The threshold can be determined by further analyzing the recent variation in the main filtered feature, the previously calculated sum of recent changes in the flow conductance, and/or the value of the feature if the signal includes pure noise, that is, the known value of the feature when no patient is attached.

At decision step 2530, the controller can determine whether the patient is previously attached to or in the process of detaching (that is, still attached to) the respiratory system. If the patient is not previously attached or detaching, that is, if the patient is detached or attaching, at step 2542, the controller can determine whether the main filtered feature is greater than a first threshold, or has the patient been attaching for a predetermined amount of time. If the main filtered feature is greater than the first threshold, or if the patient has been attaching to the respiratory system for at least the predetermined amount of time, at step 2550, the controller can determine that the patient is attached to the respiratory system.

If the main filtered feature is not greater than the first threshold, and/or if the patient has not been attaching to the respiratory device for at least the predetermined amount of time, at step 2544, the controller can determine whether the main filtered feature is greater than a second threshold that is lower than the first threshold. If the main filtered feature is less than the second threshold, at step 2546, the controller can determine that the patient is detached. If the main filtered feature is greater than the second threshold, but is not greater than the first threshold (that is, between the first and second thresholds), at step 2548, the controller can determine that the patient is attaching to the respiratory system.

If the patient is previously attached or detaching, at step 2532, the controller can determine whether the main filtered feature is less than a third threshold, or has the patient been in the process of detaching for a predetermined amount of time. If the main filtered feature is lower than the third threshold, or if the patient has been detaching for a predetermined amount of time, at step 2534, the controller can determine that the patient is detached.

If the main filtered feature is not lower than the third threshold, and/or if the patient has not been detaching for a predetermined amount of time, at step 2536, the controller can determine whether the main filtered feature is lower than a fourth threshold that is higher than the third threshold. If the main filtered feature is lower than the fourth threshold but not lower than the third threshold (that is, between the third and fourth threshold), at step 2538, the controller can determine the patient is detaching from the respiratory system. If the main filtered feature is not lower (or higher) than the fourth threshold, at step 2540, the controller can determine that the patient is attached.

The first and fourth thresholds can be the same or different (for example, the fourth threshold can be lower than the first threshold). The second and fourth thresholds can be the same or different (for example, the fourth threshold can be lower than the second threshold). The absolute value of the difference between the first and second thresholds and the difference between the third and fourth thresholds can be the same or different.

The process illustrated in FIG. 25B ensures that the controller does not make a determination that is the patient is attached or detached based on the main filtered feature briefly crossing a threshold by a small amount, for example, by determining that the patient is still in the process of attaching or detaching from the respiratory system. If the main filtered feature crosses the threshold, but not by a significant amount, the patient is determined to be attaching or detaching. Further, if the patient is determined to be attaching or detaching for a certain amount of time, the determination can switch to attached or detached, without needing the main filtered feature to be significantly above or below the feature threshold.

As shown in FIG. 27, the controller can determine the patient attachment status, for example whether the patient is attached or detached from the respiratory system, using the generated measure of patient ventilation ($\hat{V}_0$) and measure of total signal fluctuation ($\hat{V}_{short}$) described above in reference to FIG. 26. This determination can be made by comparing the measure of patient ventilation ($\hat{V}_0$) and measure of total signal fluctuation ($\hat{V}_{short}$). If the measure of patient ventilation ($\hat{V}_0$) and measure of total signal fluctuation ($\hat{V}_{short}$) are similar, the controller can determine that the majority of the signal variation is caused by the patient, and consequently, the patient is attached or connected. If the measure of patient ventilation ($\hat{V}_0$) and measure of total signal fluctuation ($\hat{V}_{short}$) are significantly dissimilar (for example, $\hat{V}_{short} \gg \hat{V}_0$), the controller can determine that the majority of signal variation is caused by random noise, and therefore, a patient is not attached or connected.

In a configuration, if the measure of instantaneous patient ventilation ($V_0$) and measure of total signal fluctuation ($V_{short}$) are similar, the controller can determine that the majority of the signal variation is caused by the patient, and consequently, the patient is attached or connected. In a configuration, if the measure of instantaneous patient ventilation ($V_0$) and measure of instantaneous total signal fluctuation ($V_{short}$) are significantly dissimilar (for example, $V_{short} \gg V_0$), the controller can determine that the majority of signal variation is caused by random noise, and therefore, a patient is not attached or connected. The relationship between the measure of patient ventilation ($\hat{V}_0$) and measure of total signal fluctuation ($\hat{V}_{short}$) can be represented by a patient connection measure ($\sigma$), which can be determined by (or including in part) the ratio between $\hat{V}_0$ and $\hat{V}_{short}$. In one non-limiting example, the equation below can be used to calculate the patient connection measure ($\sigma$).

$$\sigma \times \frac{\hat{V}_0}{\hat{V}_{short}}$$

The patient connection measure ($\sigma$) can be determined in part by using a correction factor. The correction factor can be determined by comparing two or more measures of instantaneous patient ventilation ($V_0$) with each being calculated by a different method. The correction factor can be determined by comparing two or more measures of patient ventilation ($\hat{V}_0$) with each being calculated by a different method. In a configuration, the correction factor can be used as an indication of the smoothness of the respiratory flow of the patient. The patient connection measure (σ) can be related to the signal noise ratio (SNR). In one non-limiting example, the relationship can be represented by the equation below.

$$\sigma \cong \frac{SNR^2}{1+SNR^2}$$

The patient connection measure (σ) can be zero when the signal noise ratio (SNR) is zero. The patient connection measure (σ) can approach zero as the signal noise ratio (SNR) approaches zero. The patient connection measure (σ) can be one when the signal noise ratio (SNR) is infinite. The patient connection measure (σ) can approach one as the signal noise ratio (SNR) approaches infinity. The patient connection measure (σ) can be used to determine patient attachment by comparing the patient connection measure (σ) with one or more thresholds. The controller can also alternatively determine whether the patient is attached to the respiratory system by comparing any one of the patient connection measure, the correction factor, any measures of patient minute ventilation, or any combinations thereof, against specific thresholds. The combinations can be based on an average value or any weighted average value. The correction factor and/or the measures of minute ventilation tend towards 0 when a patient is detached, and as such should exceed a certain threshold if a patient is attached to the respiratory system.

As shown in FIG. 27, the controller can, at decision step 2702, determine whether the patient is previously attached or detached to the respiratory system. If the patient is previously detached, at step 2704, the controller can determine whether the patient connection measure (σ), which can be, for example, the ratio between the measure of patient ventilation ($\hat{V}_0$) and measure of total signal fluctuation ($\hat{V}_{short}$), exceeds an attachment threshold. If the patient connection measure (σ) exceeds the attachment threshold, the controller determines at step 2706 that the patient is attached. If the patient connection measure (σ) does not exceed the attachment threshold, the controller determines at step 2708 that the patient is detached. The attachment threshold can be set to a value that corresponds to a signal to noise ratio above which it can be reliably assumed that the fluctuations are not entirely generated by random noise.

In a configuration, the attachment threshold can be set to a value that corresponds to a 33% signal to noise ratio. In a configuration, the attachment threshold can be set to a value that corresponds to a signal to noise ratio that is below or above 33%. In a configuration, at step 2704, the controller can determine whether the patient connection measure (σ) exceeds the attachment threshold or another threshold continuously for a set time period. The time period can be such that a short time period of data, such as a few seconds, will have been decayed away, such as a decay of about 80%, by the end of the time period. This can advantageously prevent a few seconds of erroneous data from resulting in an incorrect determination of patient attachment.

If the patient is previously attached, at step 2710, the controller can determine whether the patient connection measure (σ) falls below a detachment threshold. If the patient connection measure (σ) falls below the detachment threshold, the controller determines at step 2714 that the patient is detached. If the patient connection measure (σ) does not fall below the detachment threshold, the controller determines at step 2712 that the patient is attached. The detachment threshold is below the attachment threshold. The detachment threshold can be set at a value at which the variations can be reliably assumed to be solely caused by random noise. In a configuration, at step 2710, the controller can determine whether the patient connection measure (σ) falls below the detachment threshold continuously for a set time period. The time period can be such that a short time period of data, such as a few seconds, will have been decayed away by the end of the time period. This can advantageously prevent a few seconds of erroneous data from resulting in an incorrect determination of patient attachment.

As shown in FIG. 28, the controller can determine four categories of the patient attachment status, that is, whether the patient is detached, attaching, attached, or detaching from the respiratory system, using the patient connection measure (σ) described above. This assessment can be made by comparing the patient connection measure (σ), also described as a ratio, with one or more thresholds. In order to arrive at a determination that the patient is attached or detached, the patient connection measure (σ) must be above or below a threshold.

At decision step 2830, the controller can determine whether the patient is previously attached to or in the process of detaching (that is, still attached to) the respiratory system. If the patient is not previously attached or detaching, that is, if the patient is detached or attaching, at step 2842, the controller can determine whether patient connection measure (σ) is greater than a first threshold, or has the patient been attaching for a predetermined amount of time. If the patient connection measure (σ) is greater than the first threshold, or if the patient has been attaching to the respiratory system for at least the predetermined amount of time, at step 2850, the controller can determine that the patient is attached to the respiratory system.

If the patient connection measure (σ) is not greater than the first threshold, and/or if the patient has not been attaching to the respiratory device for at least the predetermined amount of time, at step 2844, the controller can determine whether the patient connection measure (σ) is greater than a second threshold that is lower than the first threshold. If the main filtered feature is less than the second threshold, at step 2846, the controller can determine that the patient is detached. If the patient connection measure (σ) is greater than the second threshold, but is not greater than the first threshold (that is, between the first and second thresholds), at step 2848, the controller can determine that the patient is attaching to the respiratory system.

If the patient is previously attached or detaching, at step 2832, the controller can determine whether the patient connection measure (σ) is less than a third threshold, or has the patient been in the process of detaching for a predetermined amount of time. If the patient connection measure (σ) is lower than the third threshold, or if the patient has been detaching for a predetermined amount of time, at step 2834, the controller can determine that the patient is detached.

If the patient connection measure (σ) is not lower than the third threshold, and/or if the patient has not been detaching for a predetermined amount of time, at step 2836, the controller can determine whether the patient connection measure (σ) is lower than a fourth threshold that is higher than the third threshold. If the patient connection measure (σ) is lower than the fourth threshold but not lower than the third threshold (that is, between the third and fourth thresholds), at step 2838, the controller can determine the patient is detaching from the respiratory system. If the patient connection measure (σ) is not lower (or higher) than the fourth threshold, at step 2840, the controller can determine that the patient is attached.

The first and fourth thresholds can be the same or different (for example, the fourth threshold can be lower than the first threshold). The second and fourth thresholds can be the same or different (for example, the fourth threshold can be lower than the second threshold). The absolute value of the difference between the first and second thresholds and the difference between the third and fourth thresholds can be the same or different.

The process illustrated in FIG. 28 ensures that the controller does not make a determination that the patient is attached or detached based on the patient connection measure (σ) briefly crossing a threshold by a small amount, for example, by determining that the patient is still in the process of attaching or detaching from the respiratory system. If the patient connection measure (σ) crosses the threshold, but not by a significant amount, the patient is determined to be attaching or detaching. Further, if the patient is determined to be attaching or detaching for a certain amount of time, the determination can switch to attached or detached, without needing the patient connection measure (σ) to be significantly above or below the feature threshold.

The systems and methods described in reference to FIGS. 27 and 28 can be more reliable in determining patient attachment than the systems and methods described in reference to FIGS. 25A and 25B.

Generating a Proxy Measure of Patient Ventilation

The controller can generate a proxy measure of patient ventilation (V) based on the measure of patient ventilation ($\tilde{V}_0$). Alternatively, the controller can generate the proxy measure of patient ventilation (V) based on the patient connection measure (σ) and measure of total signal fluctuation ($\tilde{V}_{short}$), as represented in the function below. The patient's minute ventilation can be estimated using the absolute value of variations in the processed flow by taking into account the estimated proportion of these variations that was caused by the patient themselves.

$$V = f(\sigma, \tilde{V}_{short})$$

The function used can be generated through machine learning by utilizing measures detailed herein in conjunction with actual measures of patient ventilation.

The proxy measure of patient ventilation (V) can be related to the actual minute patient ventilation as well as other factors such as the profile of a flow path and/or a flow restriction in the respiratory system, such as between a cannula and a patient's nose. In a configuration, the actual patient minute ventilation cannot be calculated from the proxy measure of patient ventilation (V) alone but requires factor measures. In a configuration, the proxy measure of patient ventilation (V) can be converted to or close to the actual minute patient ventilation with other factors such as the profile of a flow path, flow restriction in the respiratory system, and/or other factors. A change in the proxy measure of patient ventilation (V) can correlate to an actual change in actual patient minute ventilation for the same patient with the same nasal cannula. Accordingly, a trend in the proxy measure of patient ventilation (V) can be used to indicate a similar trend in a patient's actual minute ventilation. Further, analyzing a trend in minute ventilation can incorporate the determination of patient attachment so that the trend in minute ventilation is only evaluated using the proxy measure of patient ventilation (V) that corresponds to time periods during which the patient was determined to be attached. The proxy measure of patient ventilation (V) can have further uses that assist in the effective use of a respiratory system.

Example Applications of Breathing Detection Processes

Determining whether or not the patient is attached to the patient interface can inform on the accuracy of a respiratory rate determination, and/or for other purposes. One of the other purposes is for the process of adherence tracking. Adherence tracking is an important factor for measuring patient compliance, particularly for the purpose of insurance reimbursement. Adherence tracking informs a user, clinician, insurance provider, or others, whether or not the patient is attached, and is a part of compliance measurement, which informs whether or not the patient is using the prescribed therapy as intended. In order to err on the side of patient compliance, that is, it is more preferable to overestimate patient compliance than to underestimate it, any time at which the patient is detected as being attached to the patient interface can be logged in the electronic memory of the respiratory device as a minute in which the therapy was adhered to.

The respiratory device can keep a log of the total amount of time the patient spent attached to the device, and/or a log of how long the device was turned, on, with the adherence being a percentage of the duration when the device was turned on. The device can log the duration of each of the patient attachment status categories. The data relating to adherence can also be optionally accessible through a higher level settings menu. The menu can be password encrypted to prevent the patient from accessing it and/or otherwise protected. The compliance data can also optionally be logged for transmission to a server and/or be available for downloading by connecting the respiratory device to a second device (such as a computer or USB).

The respiratory device can generate an alarm when the patient becomes detached. The alarm can be generated instantly or after a preset time of determining that the patient has become detached. The preset time can be between about 10 seconds and about 10 minutes, or between about 30 seconds to 5 minutes, or between about 1 minute and about 2 minutes. The alarm can additionally be outputted to a nurse call port. After the alarm is generated, the device can provide an option for the user, for example, via the user interface of the respiratory device, to confirm whether the patient has been detached from the device. If the patient is still attached to the device, the user can use the option to manually override the controller's determination that the patient has been detached. The override option can reduce false positive detections, for example, in cases where the patient may be attached to the device but breathing shallowly. The controller of the device can use the patient attachment determination to determine whether to display certain parameters. For example, the controller can receive an estimate of the patient's respiratory rate, and can display the respiratory rate estimation if the patient is determined to be attached. The controller can also cause determination of whether the patient is attached to be displayed. For example, the device can display the respiratory rate estimate if the patient is determined to be attached and display a symbol and/or notification that patient attachment cannot be confirmed if the patient is not determined to be attached. This can improve the reliability of the respiratory rate estimate that is displayed.

The device can also attempt to synchronize the delivery of gases with the patient's respiration if the patient is determined to be attached. Breath synchronization can include adjusting a flow source (such as the flow generator) to have a phase matching that of the patient's breath cycle, such as by increasing a flow rate when the patient is inhaling and/or decreasing a flow rate when the patient is exhaling. A patient breath cycle may be determined using one or more measured parameters, such as a flow rate, a blower motor speed, and/or a system pressure. Additional details of breath synchronization can be found in International Patent Publication No. WO 2017/200394, filed May 17, 2017, the entirety of which is incorporated herein by reference.

The device can be configured such that it suspends the recording of certain patient parameters only when the patient is detached. The patient parameters can include oxygen efficiency, which can be calculated based on the patient's measured blood oxygen saturation (SpO2) and the measured fraction of oxygen delivered to the patient (FdO2) values. The oxygen efficiency can be determined based on the patient's measured SpO2 divided by the measured FdO2. The oxygen efficiency can also be determined based on a non-linear relationship between the patient's measured SpO2 and the measured FdO2. The device can implement one or more closed loop control systems using the oxygen efficiencies to control the flow of gases. The patient detachment detection can also be fed into an oxygen delivery control, such as a closed loop control. If the patient temporarily takes off the patient interface, the patient's oxygen saturation can decrease and the controller of the respiratory device can begin to increase the oxygen concentration in the mixture of gases to be delivered to the patient. The device can automatically adjust the FdO2 in order to achieve a targeted SpO2 value for the patient. When the patient interface is reattached to the patient, the oxygen concentration in the gases flow can be high, which can result in a spike in the patient's oxygen saturation and be harmful to the patient. The patient detachment detection can be factored into the oxygen delivery control of the device so that the controller does not begin increasing the oxygen delivery or the controller switches to a specific value when the patient is determined to be detached from the device. The device can also be configured to close the valve to stop delivery of oxygen or other breathable gas to be mixed with air upon determining that the patient is detached. Closing the valve to the inlet of oxygen or other breathable gas can reduce the cost of providing the therapy and/or improve user safety.

Additionally or alternatively, the device can be configured to reduce the flow rate, reduce or turn off power to the heating element of the humidification chamber, and/or reduce or turn off power to the heating element of the patient breathing conduit, upon determining that the patient is detached. The reduction in flow rate can reduce noise. The reduction in flow rate and/or the reduction of or turning off power to the heating element(s) of the humidification chamber and/or the patient breathing conduit can reduce power consumption of the device, thereby prolonging the battery life and/or the life of another power source of the device. Additionally, or alternatively, the device can be configured to increase the flow rate for an initial period of time when the patient is determined to be detached. An increased flow rate can improve the reliability of the patient detection processes. The initial period of time of flow rate increase can be used to confirm that the patient has actually been detached from the device, that is, to reduce false positives. If the controller determines that the patient is detached at the higher flow rate, the device can take other actions as described above (for example, deactivating certain control algorithms, outputting an alarm, reducing the flow rate, reducing or turning off power to the heating elements of the humidification chamber and/or the patient breathing conduit, and/or the like). The initial period of time can be, for example, between about 10 seconds and about 10 minutes, or between about 30 seconds to 5 minutes, or between about 1 minute and about 2 minutes. The device can resume normal operation, for example, increasing the flow rate and/or turning on power to the heating elements of the humidification chamber and/or the patient breathing conduit, etc., upon detecting that the patient is re-attached to the device.

Terminology

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount.

The scope of the present disclosure is not intended to be limited by the specific disclosures of embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A respiratory system configured to deliver a respiratory therapy to a patient, the system also configured to provide information related to a patient's breathing, the system comprising:
    a respiratory device comprising a controller, wherein the controller is configured to:
        receive data of a first parameter of a flow of gases or representative of performance of a component of the device, the first parameter indicative of the patient's respiration,
        generate a flow parameter variation data based on the data of the first parameter;
        generate a measure of patient ventilation based on the flow parameter variation data;
        generate a measure of total signal fluctuation based on the flow parameter variation data; and
        determine a patient attachment status based on a comparison between the measure of patient ventilation and the measure of total signal fluctuation;
        use the patient attachment status to control the delivery of respiratory therapy.

2. The system of claim 1, wherein the first parameter is indicative of or is flow rate.

3. The system of claim 1, wherein the controller is further configured to receive data of a second parameter of the flow of gases or representative of performance of a second component of the device, and wherein the flow parameter variation data is generated by subtracting an estimated effect of the second parameter from a measured value of the first parameter.

4. The system of claim 3, wherein the second parameter is indicative of or is motor speed.

5. The system of claim 1, wherein the controller is further configured to generate a measure of instantaneous patient ventilation from the flow parameter variation data, and wherein the measure of patient ventilation is generated by filtering the measure of instantaneous patient ventilation.

6. The system of claim 5, wherein the controller is further configured to select a portion of the flow parameter variation data.

7. The system of claim 6, wherein the measure of instantaneous patient ventilation is generated by fitting one or more functions to the selected portion of the flow parameter variation data and determining an area under an absolute value of a curve generated by the one or more functions.

8. The system of claim 7, wherein the controller is configured to perform a least squares fit to fit the one or more functions to the selected portion of the flow parameter variation data.

9. The system of claim 7, wherein determining the area under the absolute value of the curve comprises finding an integral of the absolute value of the curve generated by the one or more functions.

10. The system of claim 1, wherein the controller is further configured to generate a measure of instantaneous total signal fluctuation from the flow parameter variation data, and wherein the measure of total signal fluctuation is generated by filtering the measure of instantaneous total signal fluctuation.

11. The system of claim 10, wherein the measure of instantaneous total signal fluctuation is determined by taking the absolute value of the flow parameter variation data.

12. The system of claim 1, wherein comparing the measure of patient ventilation and the measure of total signal fluctuation comprises taking the ratio between the measure of patient ventilation and the measure of total signal fluctuation.

13. The system of claim 1, wherein the system is a non-sealed system.

14. The system of claim 13, wherein the system is configured to deliver a nasal high flow therapy.

15. The system of claim 1, further comprising a humidifier configured to humidify the gases flow to a patient.

16. The system of claim 1, wherein the patient attachment status is used to synchronize the delivery of gases.

17. The system of claim 1, wherein the controller is further configured to use the patient attachment status to interrupt an oxygen delivery control.

18. The system of claim 1, wherein the controller is further configured to use the patient attachment status to synchronize delivery of gases.

19. The system of claim 1, wherein the controller is further configured to use the patient attachment status to control a flow rate.

20. The system of claim 1, wherein the controller is further configured to use the patient attachment status to control power to a heating element.

* * * * *